US007067113B2

(12) United States Patent
Isfort et al.

(10) Patent No.: US 7,067,113 B2
(45) Date of Patent: Jun. 27, 2006

(54) METHODS FOR IDENTIFYING COMPOUNDS FOR REGULATING MUSCLE MASS OR FUNCTION USING DOPAMINE RECEPTORS

(75) Inventors: Robert Joseph Isfort, Fairfield, OH (US); Russell James Sheldon, Fairfield, OH (US)

(73) Assignee: The Procter & Gamble Company, Cincinnati, OH (US)

(*) Notice: Subject to any disclaimer, the term of this patent is extended or adjusted under 35 U.S.C. 154(b) by 411 days.

(21) Appl. No.: 10/299,642

(22) Filed: Nov. 18, 2002

(65) Prior Publication Data

US 2003/0170741 A1 Sep. 11, 2003

Related U.S. Application Data

(60) Provisional application No. 60/349,620, filed on Jan. 18, 2002.

(51) Int. Cl.
*A61K 49/00* (2006.01)
*G01N 33/53* (2006.01)
*G01N 33/567* (2006.01)

(52) U.S. Cl. ........................ 424/9.2; 424/9.1; 424/1.45; 435/7.2; 435/7.21; 435/336; 530/388.29

(58) Field of Classification Search ................. 435/7.2, 435/7.21; 424/9.1, 9.2; 514/1
See application file for complete search history.

(56) References Cited

U.S. PATENT DOCUMENTS

| | | | | |
|---|---|---|---|---|
| 5,427,942 | A | 6/1995 | Civelli et al. | |
| 5,508,384 | A | 4/1996 | Murphy et al. | |
| 5,610,282 | A | 3/1997 | Sibley et al. | |
| 5,686,573 | A | 11/1997 | Civelli et al. | |
| 2003/0049794 | A1* | 3/2003 | Weinshank et al. | ........ 435/69.1 |

FOREIGN PATENT DOCUMENTS

| | | | | |
|---|---|---|---|---|
| CA | 2024096 | A1 | | 8/1990 |
| WO | WO 91/18005 | A1 | | 11/1991 |
| WO | WO 91/00986 | A1 | | 1/1992 |
| WO | WO9200986 | A | * | 1/1992 |
| WO | WO 92/18533 | A1 | | 10/1992 |
| WO | WO 94/05695 | A1 | | 3/1994 |
| WO | WO 97/35881 | A2 | | 10/1997 |

OTHER PUBLICATIONS

P. Seeman, et al., "Dopamine receptor pharmacology", *TiPS*, vol. 15, pp. 264-270 (1994).

K. Kimura, et al., "Coupling of Human D-1 Dopamine Receptors to Different Guanine Nucleotide Binding Proteins", *The Journal of Biological Chemistry*, vol. 270, No. 24, pp. 14672-14678 (1995).

H. Y. Wang, et al., "Evidence for the Coupling of $G_q$ Protein to $D_1$ -Like Dopamine Sites in Rat Striatum: Possible Role in Dopamine-Mediated Inositol Phosphate Formation", *Molecular Pharmacology*, vol. 48, pp. 988-994 (1995).

A. Sidhu, et al., "$D_1$ Dopamine Receptors Can Interact with Both Stimulatory and Inhibitory Guanine Nucleotide Binding Proteins", *Journal of Neurochemistry*, vol. 57, No. 4, pp. 1445-1451 (1991).

B. F. O'Dowd, "Structures of Dopamine Receptors", *Journal of Neurochemistry*, vol. 60, No. 3, pp. 804-816 (1993).

C. Missale, et al., "Dopamine Receptors: From Structure to Function", *Physiological Reviews*, vol. 78, No. 1, pp. 189-225 (1998).

J. A. Gingrich, et al., "Recent Advances in the Molecular Biology of Dopamine Receptors", *Annu. Rev. Neurosci.*, vol. 16, pp. 299-321 (1993).

P. Sokoloff, et al., "Novel dopamine receptors half a decade later", *TiPS*, vol. 16, pp. 270-275 (1995).

D. M. Jackson, et al., "Dopamine Receptors: Molecular Biology, Biochemistry and Behavioral Aspects", *Pharmac. Ther.*, vol. 64, pp. 291-370 (1994).

O. Civelli, et al., "Molecular Diversity of the Dopamine Receptors", *Annu. Rev. Pramacol. Toxicol.*, vol. 32, pp. 281-307 (1993).

* cited by examiner

*Primary Examiner*—Lorraine Spector
*Assistant Examiner*—Steven Standley
(74) *Attorney, Agent, or Firm*—Naishadh N. Desai

(57) ABSTRACT

Screening methods for identifying compounds that bind to or activate ($D_1$ or $D_5$ dopamine receptors individually or in combination) or potentially regulate skeletal muscle mass or function in vivo. Also disclosed are screening methods for identifying compounds that prolong or augment the activation of $D_1$ or $D_5$ dopamine receptors or of $D_1$ or $D_5$ dopamine receptor signal transduction pathways and increase $D_1$ or $D_5$ dopamine receptor expression. Pharmaceutical compositions comprising $D_1$ or $D_5$ dopamine receptor agonists, antibodies to $D_1$ or $D_5$ dopamine receptors and methods for increasing skeletal muscle mass or function or for the treatment of skeletal muscle atrophy using $D_1$ or $D_5$ dopamine receptors as the target for intervention and methods for treatment of muscular dystrophies are described.

3 Claims, 4 Drawing Sheets

SEQUENCE LISTING

```
<160> NUMBER OF SEQ ID NOS: 32

<210> SEQ ID NO 1
<211> LENGTH: 2342
<212> TYPE: DNA
<213> ORGANISM: Homo sapiens
<220> FEATURE:
<221> NAME/KEY: CDS
<222> LOCATION: (277)..(1617)
<223> OTHER INFORMATION:
```

-continued

<400> SEQUENCE: 1

```
gaattcaggg gctttctggt gcccaagaca gtgacctgca gcaagggagt cagaagacag      60

atgtagaaat caagagtgac catccacggg attgacttgg attgccactc aagcggtcct     120

ctcatggaat gttggtgagg ccctctgcca gggaagcaat ctggctgtgc aaagtgctgc     180

ctggtgggga ggactcctgg aaatctgact gacccctatt ccctgcttag gaacttgagg     240

ggtgtcagag cccctgatgt gctttctctt aggaag atg agg act ctg aac acc       294
                                        Met Arg Thr Leu Asn Thr
                                        1               5

tct gcc atg gac ggg act ggg ctg gtg gtg gag agg gac ttc tct gtt       342
Ser Ala Met Asp Gly Thr Gly Leu Val Val Glu Arg Asp Phe Ser Val
            10                  15                  20

cgt atc ctc act gcc tgt ttc ctg tcg ctg ctc atc ctg tcc acg ctc       390
Arg Ile Leu Thr Ala Cys Phe Leu Ser Leu Leu Ile Leu Ser Thr Leu
        25                  30                  35

ctg ggg aac acg ctg gtc tgt gct gcc gtt atc agg ttc cga cac ctg       438
Leu Gly Asn Thr Leu Val Cys Ala Ala Val Ile Arg Phe Arg His Leu
    40                  45                  50

cgg tcc aag gtg acc aac ttc ttt gtc atc tcc ttg gct gtg tca gat       486
Arg Ser Lys Val Thr Asn Phe Phe Val Ile Ser Leu Ala Val Ser Asp
55                  60                  65                  70

ctc ttg gtg gcc gtc ctg gtc atg ccc tgg aag gca gtg gct gag att       534
Leu Leu Val Ala Val Leu Val Met Pro Trp Lys Ala Val Ala Glu Ile
                75                  80                  85

gct ggc ttc tgg ccc ttt ggg tcc ttc tgt aac atc tgg gtg gcc ttt       582
Ala Gly Phe Trp Pro Phe Gly Ser Phe Cys Asn Ile Trp Val Ala Phe
            90                  95                  100

gac atc atg tgc tcc act gca tcc atc ctc aac ctc tgt gtg atc agc       630
Asp Ile Met Cys Ser Thr Ala Ser Ile Leu Asn Leu Cys Val Ile Ser
        105                 110                 115

gtg gac agg tat tgg gct atc tcc agc cct ttc cgg tat gag aga aag       678
Val Asp Arg Tyr Trp Ala Ile Ser Ser Pro Phe Arg Tyr Glu Arg Lys
    120                 125                 130

atg acc ccc aag gca gcc ttc atc ctg atc agt gtg gca tgg acc ttg       726
Met Thr Pro Lys Ala Ala Phe Ile Leu Ile Ser Val Ala Trp Thr Leu
135                 140                 145                 150

tct gta ctc atc tcc ttc atc cca gtg cag ctc agc tgg cac aag gca       774
Ser Val Leu Ile Ser Phe Ile Pro Val Gln Leu Ser Trp His Lys Ala
                155                 160                 165

aaa ccc aca agc ccc tct gat gga aat gcc act tcc ctg gct gag acc       822
Lys Pro Thr Ser Pro Ser Asp Gly Asn Ala Thr Ser Leu Ala Glu Thr
            170                 175                 180

ata gac aac tgt gac tcc agc ctc agc agg aca tat gcc atc tca tcc       870
Ile Asp Asn Cys Asp Ser Ser Leu Ser Arg Thr Tyr Ala Ile Ser Ser
        185                 190                 195

tct gta ata agc ttt tac atc cct gtg gcc atc atg att gtc acc tac       918
Ser Val Ile Ser Phe Tyr Ile Pro Val Ala Ile Met Ile Val Thr Tyr
    200                 205                 210

acc agg atc tac agg att gct cag aaa caa ata cgg cgc att gcg gcc       966
Thr Arg Ile Tyr Arg Ile Ala Gln Lys Gln Ile Arg Arg Ile Ala Ala
215                 220                 225                 230

ttg gag agg gca gca gtc cac gcc aag aat tgc cag acc acc aca ggt      1014
Leu Glu Arg Ala Ala Val His Ala Lys Asn Cys Gln Thr Thr Thr Gly
                235                 240                 245

aat gga aag cct gtc gaa tgt tct caa ccg gaa agt tct ttt aag atg      1062
Asn Gly Lys Pro Val Glu Cys Ser Gln Pro Glu Ser Ser Phe Lys Met
            250                 255                 260

tcc ttc aaa aga gaa act aaa gtc ctg aag act ctg tcg gtg atc atg      1110
```

-continued

```
Ser Phe Lys Arg Glu Thr Lys Val Leu Lys Thr Leu Ser Val Ile Met
        265                 270                 275

ggt gtg ttt gtg tgc tgt tgg cta cct ttc ttc atc ttg aac tgc att     1158
Gly Val Phe Val Cys Cys Trp Leu Pro Phe Phe Ile Leu Asn Cys Ile
    280                 285                 290

ttg ccc ttc tgt ggg tct ggg gag acg cag ccc ttc tgc att gat tcc     1206
Leu Pro Phe Cys Gly Ser Gly Glu Thr Gln Pro Phe Cys Ile Asp Ser
295                 300                 305                 310

aac acc ttt gac gtg ttt gtg tgg ttt ggg tgg gct aat tca tcc ttg     1254
Asn Thr Phe Asp Val Phe Val Trp Phe Gly Trp Ala Asn Ser Ser Leu
                315                 320                 325

aac ccc atc att tat gcc ttt aat gct gat ttt cgg aag gca ttt tca     1302
Asn Pro Ile Ile Tyr Ala Phe Asn Ala Asp Phe Arg Lys Ala Phe Ser
            330                 335                 340

acc ctc tta gga tgc tac aga ctt tgc cct gcg acg aat aat gcc ata     1350
Thr Leu Leu Gly Cys Tyr Arg Leu Cys Pro Ala Thr Asn Asn Ala Ile
        345                 350                 355

gag acg gtg agt atc aat aac aat ggg gcc gcg atg ttt tcc agc cat     1398
Glu Thr Val Ser Ile Asn Asn Asn Gly Ala Ala Met Phe Ser Ser His
    360                 365                 370

cat gag cca cga ggc tcc atc tcc aag gag tgc aat ctg gtt tac ctg     1446
His Glu Pro Arg Gly Ser Ile Ser Lys Glu Cys Asn Leu Val Tyr Leu
375                 380                 385                 390

atc cca cat gct gtg ggc tcc tct gag gac ctg aaa aag gag gag gca     1494
Ile Pro His Ala Val Gly Ser Ser Glu Asp Leu Lys Lys Glu Glu Ala
                395                 400                 405

gct ggc atc gcc aga ccc ttg gag aag ctg tcc cca gcc cta tcg gtc     1542
Ala Gly Ile Ala Arg Pro Leu Glu Lys Leu Ser Pro Ala Leu Ser Val
            410                 415                 420

ata ttg gac tat gac act gac gtc tct ctg gag aag atc caa ccc atg     1590
Ile Leu Asp Tyr Asp Thr Asp Val Ser Leu Glu Lys Ile Gln Pro Met
        425                 430                 435

aca caa aac ggt cag cac cca acc tga actcgcagat gaatcctgcc           1637
Thr Gln Asn Gly Gln His Pro Thr
    440                 445

acacatgctc atcccaaaag ctagaggaga ttgctctggg gtttgctatt aagaaactaa   1697

ggtacggtga gactctgagg tgtcaggaga gccctctgct gctttccaac acacaattaa   1757

ctccgtttcc aaatacattc cagtgtattt tctgtgttgt tcatagtcaa tcaaacaggg   1817

acactacaaa catggggagc cataagggac atgtctttgg cttcagaatt gtttttagaa   1877

atttattctt atcttaggat ttaccaaata gggcaaagaa tcaacagtga acagcttcac   1937

ttaaaatcaa atttttctgg gaagaaaatg agatgggttg agtttgctgt atacaaacag   1997

gtgctaacac tgttcccagc aaagttttca gattgtaaag gtaggtgcat gccttcataa   2057

attatttcta aaacattaat tgaggcttac agtaggagtg agaaattttt ttccagaatt   2117

gagagatgtt ttgttgatat tggttctatt tatttattgt atatatggat atttttaatt   2177

tatgatataa taaatatata tttatcatat ttaataggat aaattaatga gttttatcca   2237

agaccttaca accacatttc tggccattta actagcactt tataagccaa tgaagcaaac   2297

acacagactc tgtgagattc taaatgttca tgtgtaactt ctaga                   2342


<210> SEQ ID NO 2
<211> LENGTH: 446
<212> TYPE: PRT
<213> ORGANISM: Homo sapiens

<400> SEQUENCE: 2
```

-continued

```
Met Arg Thr Leu Asn Thr Ser Ala Met Asp Gly Thr Gly Leu Val Val
1               5                   10                  15

Glu Arg Asp Phe Ser Val Arg Ile Leu Thr Ala Cys Phe Leu Ser Leu
            20                  25                  30

Leu Ile Leu Ser Thr Leu Leu Gly Asn Thr Leu Val Cys Ala Ala Val
        35                  40                  45

Ile Arg Phe Arg His Leu Arg Ser Lys Val Thr Asn Phe Phe Val Ile
    50                  55                  60

Ser Leu Ala Val Ser Asp Leu Leu Val Ala Val Leu Val Met Pro Trp
65                  70                  75                  80

Lys Ala Val Ala Glu Ile Ala Gly Phe Trp Pro Phe Gly Ser Phe Cys
                85                  90                  95

Asn Ile Trp Val Ala Phe Asp Ile Met Cys Ser Thr Ala Ser Ile Leu
            100                 105                 110

Asn Leu Cys Val Ile Ser Val Asp Arg Tyr Trp Ala Ile Ser Ser Pro
        115                 120                 125

Phe Arg Tyr Glu Arg Lys Met Thr Pro Lys Ala Ala Phe Ile Leu Ile
    130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Ala
                165                 170                 175

Thr Ser Leu Ala Glu Thr Ile Asp Asn Cys Asp Ser Ser Leu Ser Arg
            180                 185                 190

Thr Tyr Ala Ile Ser Ser Ser Val Ile Ser Phe Tyr Ile Pro Val Ala
        195                 200                 205

Ile Met Ile Val Thr Tyr Thr Arg Ile Tyr Arg Ile Ala Gln Lys Gln
    210                 215                 220

Ile Arg Arg Ile Ala Ala Leu Glu Arg Ala Ala Val His Ala Lys Asn
225                 230                 235                 240

Cys Gln Thr Thr Thr Gly Asn Gly Lys Pro Val Glu Cys Ser Gln Pro
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285

Phe Ile Leu Asn Cys Ile Leu Pro Phe Cys Gly Ser Gly Glu Thr Gln
    290                 295                 300

Pro Phe Cys Ile Asp Ser Asn Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Arg Lys Ala Phe Ser Thr Leu Leu Gly Cys Tyr Arg Leu Cys Pro
            340                 345                 350

Ala Thr Asn Asn Ala Ile Glu Thr Val Ser Ile Asn Asn Asn Gly Ala
        355                 360                 365

Ala Met Phe Ser Ser His His Glu Pro Arg Gly Ser Ile Ser Lys Glu
    370                 375                 380

Cys Asn Leu Val Tyr Leu Ile Pro His Ala Val Gly Ser Ser Glu Asp
385                 390                 395                 400

Leu Lys Lys Glu Glu Ala Ala Gly Ile Ala Arg Pro Leu Glu Lys Leu
                405                 410                 415

Ser Pro Ala Leu Ser Val Ile Leu Asp Tyr Asp Thr Asp Val Ser Leu
```

-continued

```
        420                 425                 430

Glu Lys Ile Gln Pro Met Thr Gln Asn Gly Gln His Pro Thr
        435                 440                 445


<210> SEQ ID NO 3
<211> LENGTH: 1705
<212> TYPE: DNA
<213> ORGANISM: Homo sapiens
<220> FEATURE:
<221> NAME/KEY: CDS
<222> LOCATION: (274)..(1614)
<223> OTHER INFORMATION:

<400> SEQUENCE: 3

ttcaggggct ttctggtgcc cttgacagtg acctgcagca agggagtcag aagacagatg      60

tagaaatcaa gagtgaccat ccacgggatt gacttggatt gccactcaag cggtcctctc     120

atggaatgtt ggtgaggccc tctgccaggg aagcaatctg gctgtgcaaa gtgctgcctg     180

gtggggagga ctcctggaaa tctgactgac ccctattccc tgcttgggaa cttgaggggt     240

gtcagagccc ctgatgtgct ttctcttagg aag atg agg act ctg aac acc tct      294
                                     Met Arg Thr Leu Asn Thr Ser
                                     1               5

gcc atg gac ggg act ggg ctg gtg gtg gag agg gac ttc tct gtt cgt      342
Ala Met Asp Gly Thr Gly Leu Val Val Glu Arg Asp Phe Ser Val Arg
        10                  15                  20

atc ctc act gcc tgt ttc ctg tcg ctg ctc atc ctg tcc acg ctc ctg      390
Ile Leu Thr Ala Cys Phe Leu Ser Leu Leu Ile Leu Ser Thr Leu Leu
    25                  30                  35

ggg aac acg ctg gtc tgt gct gcc gtt atc agg ttc cga cac ctg cgg      438
Gly Asn Thr Leu Val Cys Ala Ala Val Ile Arg Phe Arg His Leu Arg
40                  45                  50                  55

tcc aag gtg acc aac ttc ttt gtc atc tcc ttg gct gtg tca gat ctc      486
Ser Lys Val Thr Asn Phe Phe Val Ile Ser Leu Ala Val Ser Asp Leu
                60                  65                  70

ttg gtg gcc gtc ctg gtc atg ccc tgg aag gca gtg gct gag att gct      534
Leu Val Ala Val Leu Val Met Pro Trp Lys Ala Val Ala Glu Ile Ala
            75                  80                  85

ggc ttc tgg ccc ttt ggg tcc ttc tgt aac atc tgg gtg gcc ttt gac      582
Gly Phe Trp Pro Phe Gly Ser Phe Cys Asn Ile Trp Val Ala Phe Asp
        90                  95                  100

atc atg tgc tcc act gca tcc atc ctc aac ctc tgt gtg atc agc gtg      630
Ile Met Cys Ser Thr Ala Ser Ile Leu Asn Leu Cys Val Ile Ser Val
    105                 110                 115

gac agg tat tgg gct atc tcc agc cct ttc cgg tat gag aga aag atg      678
Asp Arg Tyr Trp Ala Ile Ser Ser Pro Phe Arg Tyr Glu Arg Lys Met
120                 125                 130                 135

acc ccc aag gca gcc ttc atc ctg atc agt gtg gca tgg acc ttg tct      726
Thr Pro Lys Ala Ala Phe Ile Leu Ile Ser Val Ala Trp Thr Leu Ser
                140                 145                 150

gta ctc atc tcc ttc atc cca gtg cag ctc agc tgg cac aag gca aaa      774
Val Leu Ile Ser Phe Ile Pro Val Gln Leu Ser Trp His Lys Ala Lys
            155                 160                 165

ccc aca agc ccc tct gat gga aat gcc act tcc ctg gct gag acc ata      822
Pro Thr Ser Pro Ser Asp Gly Asn Ala Thr Ser Leu Ala Glu Thr Ile
        170                 175                 180

gac aac tgt gac tcc agc ctc agc agg aca tat gcc atc tca tcc tct      870
Asp Asn Cys Asp Ser Ser Leu Ser Arg Thr Tyr Ala Ile Ser Ser Ser
    185                 190                 195

gta ata agc ttt tac atc cct gtg gcc atc atg att gtc acc tac acc      918
Val Ile Ser Phe Tyr Ile Pro Val Ala Ile Met Ile Val Thr Tyr Thr
```

-continued

```
200                 205                 210                 215

agg atc tac agg att gct cag aaa caa ata cgg cgc att gcg gcc ttg      966
Arg Ile Tyr Arg Ile Ala Gln Lys Gln Ile Arg Arg Ile Ala Ala Leu
                220                 225                 230

gag agg gca gca gtc cac gcc aag aat tgc cag acc acc aca ggt aat     1014
Glu Arg Ala Ala Val His Ala Lys Asn Cys Gln Thr Thr Thr Gly Asn
            235                 240                 245

gga aag cct gtc gaa tgt tct caa ccg gaa agt tct ttt aag atg tcc     1062
Gly Lys Pro Val Glu Cys Ser Gln Pro Glu Ser Ser Phe Lys Met Ser
        250                 255                 260

ttc aaa aga gaa act aaa gtc ctg aag act ctg tcg gtg atc atg ggt     1110
Phe Lys Arg Glu Thr Lys Val Leu Lys Thr Leu Ser Val Ile Met Gly
    265                 270                 275

gtg ttt gtg tgc tgt tgg cta cct ttc ttc atc ttg aac tgc att ttg     1158
Val Phe Val Cys Cys Trp Leu Pro Phe Phe Ile Leu Asn Cys Ile Leu
280                 285                 290                 295

ccc ttc tgt ggg tct ggg gag acg cag ccc ttc tgc att gat tcc aac     1206
Pro Phe Cys Gly Ser Gly Glu Thr Gln Pro Phe Cys Ile Asp Ser Asn
                300                 305                 310

acc ttt gac gtg ttt gtg tgg ttt ggg tgg gct aat tca tcc ttg aac     1254
Thr Phe Asp Val Phe Val Trp Phe Gly Trp Ala Asn Ser Ser Leu Asn
            315                 320                 325

ccc atc att tat gcc ttt aat gct gat ttt cgg aag gca ttt tca acc     1302
Pro Ile Ile Tyr Ala Phe Asn Ala Asp Phe Arg Lys Ala Phe Ser Thr
        330                 335                 340

ctc tta gga tgc tac aga ctt tgc cct gcg acg aat aat gcc ata gag     1350
Leu Leu Gly Cys Tyr Arg Leu Cys Pro Ala Thr Asn Asn Ala Ile Glu
    345                 350                 355

acg gtg agt atc aat aac aat ggg gcc gcg atg ttt tcc agc cat cat     1398
Thr Val Ser Ile Asn Asn Asn Gly Ala Ala Met Phe Ser Ser His His
360                 365                 370                 375

gag cca cga ggc tcc atc tcc aag gag tgc aat ctg gtt tac ctg atc     1446
Glu Pro Arg Gly Ser Ile Ser Lys Glu Cys Asn Leu Val Tyr Leu Ile
                380                 385                 390

cca cat gct gtg ggc tcc tct gag gac ctg aaa aag gag gag gca gct     1494
Pro His Ala Val Gly Ser Ser Glu Asp Leu Lys Lys Glu Glu Ala Ala
            395                 400                 405

ggc atc gcc aga ccc ttg gag aag ctg tcc cca gcc cta tcg gtc ata     1542
Gly Ile Ala Arg Pro Leu Glu Lys Leu Ser Pro Ala Leu Ser Val Ile
        410                 415                 420

ttg gac tat gac act gac gtc tct ctg gag aag atc caa ccc atc aca     1590
Leu Asp Tyr Asp Thr Asp Val Ser Leu Glu Lys Ile Gln Pro Ile Thr
    425                 430                 435

caa aac ggt cag cac cca acc tga actcgcagat gaatcctgcc acacatgctc    1644
Gln Asn Gly Gln His Pro Thr
440                 445

atcccaaaag ctagaggaga ttgctctggg gtttgctatt aagaaactaa ggtacggtga   1704

g                                                                   1705


<210> SEQ ID NO 4
<211> LENGTH: 446
<212> TYPE: PRT
<213> ORGANISM: Homo sapiens

<400> SEQUENCE: 4

Met Arg Thr Leu Asn Thr Ser Ala Met Asp Gly Thr Gly Leu Val Val
1               5                   10                  15

Glu Arg Asp Phe Ser Val Arg Ile Leu Thr Ala Cys Phe Leu Ser Leu
            20                  25                  30
```

-continued

```
Leu Ile Leu Ser Thr Leu Leu Gly Asn Thr Leu Val Cys Ala Ala Val
        35                  40                  45

Ile Arg Phe Arg His Leu Arg Ser Lys Val Thr Asn Phe Phe Val Ile
    50                  55                  60

Ser Leu Ala Val Ser Asp Leu Leu Val Ala Val Leu Val Met Pro Trp
65                  70                  75                  80

Lys Ala Val Ala Glu Ile Ala Gly Phe Trp Pro Phe Gly Ser Phe Cys
                85                  90                  95

Asn Ile Trp Val Ala Phe Asp Ile Met Cys Ser Thr Ala Ser Ile Leu
            100                 105                 110

Asn Leu Cys Val Ile Ser Val Asp Arg Tyr Trp Ala Ile Ser Ser Pro
        115                 120                 125

Phe Arg Tyr Glu Arg Lys Met Thr Pro Lys Ala Ala Phe Ile Leu Ile
    130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Ala
                165                 170                 175

Thr Ser Leu Ala Glu Thr Ile Asp Asn Cys Asp Ser Ser Leu Ser Arg
            180                 185                 190

Thr Tyr Ala Ile Ser Ser Ser Val Ile Ser Phe Tyr Ile Pro Val Ala
        195                 200                 205

Ile Met Ile Val Thr Tyr Thr Arg Ile Tyr Arg Ile Ala Gln Lys Gln
    210                 215                 220

Ile Arg Arg Ile Ala Ala Leu Glu Arg Ala Ala Val His Ala Lys Asn
225                 230                 235                 240

Cys Gln Thr Thr Thr Gly Asn Gly Lys Pro Val Glu Cys Ser Gln Pro
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285

Phe Ile Leu Asn Cys Ile Leu Pro Phe Cys Gly Ser Gly Glu Thr Gln
    290                 295                 300

Pro Phe Cys Ile Asp Ser Asn Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Arg Lys Ala Phe Ser Thr Leu Leu Gly Cys Tyr Arg Leu Cys Pro
            340                 345                 350

Ala Thr Asn Asn Ala Ile Glu Thr Val Ser Ile Asn Asn Asn Gly Ala
        355                 360                 365

Ala Met Phe Ser Ser His His Glu Pro Arg Gly Ser Ile Ser Lys Glu
    370                 375                 380

Cys Asn Leu Val Tyr Leu Ile Pro His Ala Val Gly Ser Ser Glu Asp
385                 390                 395                 400

Leu Lys Lys Glu Glu Ala Ala Gly Ile Ala Arg Pro Leu Glu Lys Leu
                405                 410                 415

Ser Pro Ala Leu Ser Val Ile Leu Asp Tyr Asp Thr Asp Val Ser Leu
            420                 425                 430

Glu Lys Ile Gln Pro Ile Thr Gln Asn Gly Gln His Pro Thr
        435                 440                 445
```

-continued

```
<210> SEQ ID NO 5
<211> LENGTH: 1689
<212> TYPE: DNA
<213> ORGANISM: Homo sapiens
<220> FEATURE:
<221> NAME/KEY: CDS
<222> LOCATION: (274)..(1614)
<223> OTHER INFORMATION:

<400> SEQUENCE: 5

ttcaggggct ttctggtgcc cttgacagtg acctgcagca agggagtcag aagacagatg      60

tagaaatcaa gagtgaccat ccacgggatt gacttggatt gccactcaag cggtcctctc     120

atggaatgtt ggtgaggccc tctgccaggg aagcaatctg gctgtgcaaa gtgctgcctg     180

gtggggagga ctcctggaaa tctgactgac ccctattccc tgcttaggaa cttgaggggt     240

gtcagagccc ctgatgtgct ttctcttagg aag atg agg act ctg aac acc tct       294
                                     Met Arg Thr Leu Asn Thr Ser
                                     1               5

gcc atg gac ggg act ggg ctg gtg gtg gag agg gac ttc tct gtt cgt        342
Ala Met Asp Gly Thr Gly Leu Val Val Glu Arg Asp Phe Ser Val Arg
        10                  15                  20

atc ctc act gcc tgt ttc cta tcg ctg ctc atc ctg tcc acg ctc ctg        390
Ile Leu Thr Ala Cys Phe Leu Ser Leu Leu Ile Leu Ser Thr Leu Leu
    25                  30                  35

ggg aac acg ctg gtc tgt gct gcc gtt atc agg ttc cga cac ctg cgg        438
Gly Asn Thr Leu Val Cys Ala Ala Val Ile Arg Phe Arg His Leu Arg
40                  45                  50                  55

tcc aag gtg acc aac ttc ttt gtc atc tcc ttg gct gtg tca gat ctc        486
Ser Lys Val Thr Asn Phe Phe Val Ile Ser Leu Ala Val Ser Asp Leu
                60                  65                  70

ttg gtg gca gtc ctg gtc atg ccc tgg aag gca gtg gct gag att gct        534
Leu Val Ala Val Leu Val Met Pro Trp Lys Ala Val Ala Glu Ile Ala
            75                  80                  85

ggc ttc tgg ccc ttt ggg tcc ttc tgt aac atc tgg gtg gcc ttt gac        582
Gly Phe Trp Pro Phe Gly Ser Phe Cys Asn Ile Trp Val Ala Phe Asp
        90                  95                  100

atc atg tgc tcc act gca tcc atc ctc aac ctc tgt gtg atc agc gtg        630
Ile Met Cys Ser Thr Ala Ser Ile Leu Asn Leu Cys Val Ile Ser Val
    105                 110                 115

gac agg tat tgg gct atc tcc agc cct ttc cgg tat gag aga aag atg        678
Asp Arg Tyr Trp Ala Ile Ser Ser Pro Phe Arg Tyr Glu Arg Lys Met
120                 125                 130                 135

acc ccc aag gca gcc ttc atc ctg atc agt gtg gca tgg acc ttg tct        726
Thr Pro Lys Ala Ala Phe Ile Leu Ile Ser Val Ala Trp Thr Leu Ser
                140                 145                 150

gta ctc atc tcc ttc atc cca gtg cag ctc agc tgg cac aag gca aaa        774
Val Leu Ile Ser Phe Ile Pro Val Gln Leu Ser Trp His Lys Ala Lys
            155                 160                 165

ccc aca agc ccc tct gat gga aat gcc act tcc ctg gct gag acc ata        822
Pro Thr Ser Pro Ser Asp Gly Asn Ala Thr Ser Leu Ala Glu Thr Ile
        170                 175                 180

gac aac tgt gac tcc agc ctc agc agg aca tat gcc atc tca tcc tct        870
Asp Asn Cys Asp Ser Ser Leu Ser Arg Thr Tyr Ala Ile Ser Ser Ser
    185                 190                 195

gta ata agc ttt tac atc cct gtg gcc atc atg att gtc acc tac acc        918
Val Ile Ser Phe Tyr Ile Pro Val Ala Ile Met Ile Val Thr Tyr Thr
200                 205                 210                 215

agg atc tac agg att gct cag aaa caa ata cgg cgc att gcg gcc ttg        966
Arg Ile Tyr Arg Ile Ala Gln Lys Gln Ile Arg Arg Ile Ala Ala Leu
                220                 225                 230
```

-continued gag agg gca gca gtc cac gcc aag aat tgc cag acc acc aca ggt aat 1014
Glu Arg Ala Ala Val His Ala Lys Asn Cys Gln Thr Thr Thr Gly Asn
235 240 245 gga aag cct gtc gaa tgt tct caa ccg gaa agt tct ttt aag atg tcc 1062
Gly Lys Pro Val Glu Cys Ser Gln Pro Glu Ser Ser Phe Lys Met Ser
250 255 260 ttc aaa aga gaa act aaa gtc ctg aag act ctg tcg gtg atc atg ggt 1110
Phe Lys Arg Glu Thr Lys Val Leu Lys Thr Leu Ser Val Ile Met Gly
265 270 275 gtg ttt gtg tgc tgt tgg cta cct ttc ttc atc ttg aac tgc att ttg 1158
Val Phe Val Cys Cys Trp Leu Pro Phe Phe Ile Leu Asn Cys Ile Leu
280 285 290 295 ccc ttc tgt ggg tct ggg gag acg cag ccc ttc tgc att gat tcc aac 1206
Pro Phe Cys Gly Ser Gly Glu Thr Gln Pro Phe Cys Ile Asp Ser Asn
300 305 310 acc ttt gac gtg ttt gtg tgg ttt ggg tgg gct aat tca tcc ttg aac 1254
Thr Phe Asp Val Phe Val Trp Phe Gly Trp Ala Asn Ser Ser Leu Asn
315 320 325 ccc atc att tat gcc ttt aat gct gat ttt cgg aag gca ttt tca acc 1302
Pro Ile Ile Tyr Ala Phe Asn Ala Asp Phe Arg Lys Ala Phe Ser Thr
330 335 340 ctc tta gga tgc tac aga ctt tgc cct gcg acg aat aat gcc ata gag 1350
Leu Leu Gly Cys Tyr Arg Leu Cys Pro Ala Thr Asn Asn Ala Ile Glu
345 350 355 acg gtg agt atc aat aac aat ggg gcc gcg atg ttt tcc agc cat cat 1398
Thr Val Ser Ile Asn Asn Asn Gly Ala Ala Met Phe Ser Ser His His
360 365 370 375 gag cca cga ggc tcc atc tcc aag gag tgc aat ctg gtt tac ctg atc 1446
Glu Pro Arg Gly Ser Ile Ser Lys Glu Cys Asn Leu Val Tyr Leu Ile
380 385 390 cca cat gct gtg ggc tcc tct gag gac ctg aaa aag gag gag gca gct 1494
Pro His Ala Val Gly Ser Ser Glu Asp Leu Lys Lys Glu Glu Ala Ala
395 400 405 ggc atc gcc aga ccc ttg gag aag ctg tcc cca gcc cta tcg gtc ata 1542
Gly Ile Ala Arg Pro Leu Glu Lys Leu Ser Pro Ala Leu Ser Val Ile
410 415 420 ttg gac tat gac act gac gtc tct ctg gag aag atc caa ccc atc aca 1590
Leu Asp Tyr Asp Thr Asp Val Ser Leu Glu Lys Ile Gln Pro Ile Thr
425 430 435 caa aac ggt cag cac cca acc tga actcgcagat gaatcctgcc acacatgctc 1644
Gln Asn Gly Gln His Pro Thr
440 445 atcccaaaag ctagaggaga ttgctctggg gtttgctatt aagaa 1689

<210> SEQ ID NO 6
<211> LENGTH: 446
<212> TYPE: PRT
<213> ORGANISM: Homo sapiens

<400> SEQUENCE: 6

Met Arg Thr Leu Asn Thr Ser Ala Met Asp Gly Thr Gly Leu Val Val
1 5 10 15

Glu Arg Asp Phe Ser Val Arg Ile Leu Thr Ala Cys Phe Leu Ser Leu
20 25 30

Leu Ile Leu Ser Thr Leu Leu Gly Asn Thr Leu Val Cys Ala Ala Val
35 40 45

Ile Arg Phe Arg His Leu Arg Ser Lys Val Thr Asn Phe Phe Val Ile
50 55 60

-continued

```
Ser Leu Ala Val Ser Asp Leu Leu Val Ala Val Leu Val Met Pro Trp
65                  70                  75                  80

Lys Ala Val Ala Glu Ile Ala Gly Phe Trp Pro Phe Gly Ser Phe Cys
                85                  90                  95

Asn Ile Trp Val Ala Phe Asp Ile Met Cys Ser Thr Ala Ser Ile Leu
            100                 105                 110

Asn Leu Cys Val Ile Ser Val Asp Arg Tyr Trp Ala Ile Ser Ser Pro
        115                 120                 125

Phe Arg Tyr Glu Arg Lys Met Thr Pro Lys Ala Ala Phe Ile Leu Ile
    130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Ala
                165                 170                 175

Thr Ser Leu Ala Glu Thr Ile Asp Asn Cys Asp Ser Ser Leu Ser Arg
            180                 185                 190

Thr Tyr Ala Ile Ser Ser Ser Val Ile Ser Phe Tyr Ile Pro Val Ala
        195                 200                 205

Ile Met Ile Val Thr Tyr Thr Arg Ile Tyr Arg Ile Ala Gln Lys Gln
    210                 215                 220

Ile Arg Arg Ile Ala Ala Leu Glu Arg Ala Ala Val His Ala Lys Asn
225                 230                 235                 240

Cys Gln Thr Thr Thr Gly Asn Gly Lys Pro Val Glu Cys Ser Gln Pro
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285

Phe Ile Leu Asn Cys Ile Leu Pro Phe Cys Gly Ser Gly Glu Thr Gln
    290                 295                 300

Pro Phe Cys Ile Asp Ser Asn Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Arg Lys Ala Phe Ser Thr Leu Leu Gly Cys Tyr Arg Leu Cys Pro
            340                 345                 350

Ala Thr Asn Asn Ala Ile Glu Thr Val Ser Ile Asn Asn Asn Gly Ala
        355                 360                 365

Ala Met Phe Ser Ser His His Glu Pro Arg Gly Ser Ile Ser Lys Glu
    370                 375                 380

Cys Asn Leu Val Tyr Leu Ile Pro His Ala Val Gly Ser Ser Glu Asp
385                 390                 395                 400

Leu Lys Lys Glu Glu Ala Ala Gly Ile Ala Arg Pro Leu Glu Lys Leu
                405                 410                 415

Ser Pro Ala Leu Ser Val Ile Leu Asp Tyr Asp Thr Asp Val Ser Leu
            420                 425                 430

Glu Lys Ile Gln Pro Ile Thr Gln Asn Gly Gln His Pro Thr
        435                 440                 445
```

<210> SEQ ID NO 7
<211> LENGTH: 1434
<212> TYPE: DNA
<213> ORGANISM: Homo sapiens
<220> FEATURE:
<221> NAME/KEY: CDS -continued

```
<222> LOCATION: (1)..(1434)
<223> OTHER INFORMATION:

<400> SEQUENCE: 7

atg ctg ccg cca ggc agc aac ggc acc gcg tac ccg ggg cag ttc gct       48
Met Leu Pro Pro Gly Ser Asn Gly Thr Ala Tyr Pro Gly Gln Phe Ala
1               5                   10                  15

cta tac cag cag ctg gcg cag ggg aac gcc gtg ggg ggc tcg gcg ggg       96
Leu Tyr Gln Gln Leu Ala Gln Gly Asn Ala Val Gly Gly Ser Ala Gly
            20                  25                  30

gca ccg cca ctg ggg ccc tca cag gtg gtc acc gcc tgc ctg ctg acc      144
Ala Pro Pro Leu Gly Pro Ser Gln Val Val Thr Ala Cys Leu Leu Thr
        35                  40                  45

cta ctc atc atc tgg acc ctg ctg ggc aac gtg ctg gtg tgc gca gcc      192
Leu Leu Ile Ile Trp Thr Leu Leu Gly Asn Val Leu Val Cys Ala Ala
    50                  55                  60

atc gtg cgg agc cgc cac ctg cgc gcc aac atg acc aac gtc ttc atc      240
Ile Val Arg Ser Arg His Leu Arg Ala Asn Met Thr Asn Val Phe Ile
65                  70                  75                  80

gtg tct ctg gcc gtg tca gac ctt ttc gtg gcg ctg ctg gtc atg ccc      288
Val Ser Leu Ala Val Ser Asp Leu Phe Val Ala Leu Leu Val Met Pro
                85                  90                  95

tgg aag gca gtc gcc gag gtg gcc ggt tac tgg ccc ttt gga gcg ttc      336
Trp Lys Ala Val Ala Glu Val Ala Gly Tyr Trp Pro Phe Gly Ala Phe
            100                 105                 110

tgc gac gtc tgg gtg gcc ttc gac atc atg tgc tcc act gcc tcc atc      384
Cys Asp Val Trp Val Ala Phe Asp Ile Met Cys Ser Thr Ala Ser Ile
        115                 120                 125

ctg aac ctg tgc gtc atc agc gtg gac cgc tac tgg gcc atc tcc agg      432
Leu Asn Leu Cys Val Ile Ser Val Asp Arg Tyr Trp Ala Ile Ser Arg
    130                 135                 140

ccc ttc cgc tac aag cgc aag atg act cag cgc atg gcc ttg gtc atg      480
Pro Phe Arg Tyr Lys Arg Lys Met Thr Gln Arg Met Ala Leu Val Met
145                 150                 155                 160

gtc ggc ctg gca tgg acc ttg tcc atc ctc atc tcc ttc att ccg gtc      528
Val Gly Leu Ala Trp Thr Leu Ser Ile Leu Ile Ser Phe Ile Pro Val
                165                 170                 175

cag ctc aac tgg cac agg gac cag gcg gcc tct tgg ggc ggg ctg gac      576
Gln Leu Asn Trp His Arg Asp Gln Ala Ala Ser Trp Gly Gly Leu Asp
            180                 185                 190

ctg cca aac aac ctg gcc aac tgg acg ccc tgg gag gag gac ttt tgg      624
Leu Pro Asn Asn Leu Ala Asn Trp Thr Pro Trp Glu Glu Asp Phe Trp
        195                 200                 205

gag ccc gac gtg aat gca gag aac tgt gac tcc agc ctg aat cga acc      672
Glu Pro Asp Val Asn Ala Glu Asn Cys Asp Ser Ser Leu Asn Arg Thr
    210                 215                 220

tac gcc atc tct tcc tcg ctc atc agc ttc tac atc ccc gtt gcc atc      720
Tyr Ala Ile Ser Ser Ser Leu Ile Ser Phe Tyr Ile Pro Val Ala Ile
225                 230                 235                 240

atg atc gtg acc tac acg cgc atc tac cgc atc gcc cag gtg cag atc      768
Met Ile Val Thr Tyr Thr Arg Ile Tyr Arg Ile Ala Gln Val Gln Ile
                245                 250                 255

cgc agg att tcc tcc ctg gag agg gcc gca gag cac gcg cag agc tgc      816
Arg Arg Ile Ser Ser Leu Glu Arg Ala Ala Glu His Ala Gln Ser Cys
            260                 265                 270

cgg agc agc gca gcc tgc gcg ccc gac acc agc ctg cgc gct tcc atc      864
Arg Ser Ser Ala Ala Cys Ala Pro Asp Thr Ser Leu Arg Ala Ser Ile
        275                 280                 285

aag aag gag acc aag gtt ctc aag acc ctg tcg gtg atc atg ggg gtc      912
Lys Lys Glu Thr Lys Val Leu Lys Thr Leu Ser Val Ile Met Gly Val
```

-continued

```
    290                 295                 300

ttc gtg tgt tgc tgg ctg ccc ttc ttc atc ctt aac tgc atg gtc cct      960
Phe Val Cys Cys Trp Leu Pro Phe Phe Ile Leu Asn Cys Met Val Pro
305                 310                 315                 320

ttc tgc agt gga cac ccc gaa ggc cct ccg gcc ggc ttc ccc tgc gtc     1008
Phe Cys Ser Gly His Pro Glu Gly Pro Pro Ala Gly Phe Pro Cys Val
                325                 330                 335

agt gag acc acc ttc gac gtc ttc gtc tgg ttc ggc tgg gct aac tcc     1056
Ser Glu Thr Thr Phe Asp Val Phe Val Trp Phe Gly Trp Ala Asn Ser
            340                 345                 350

tca ctc aac ccc gtc atc tat gcc ttc aac gcc gac ttt cag aag gtg     1104
Ser Leu Asn Pro Val Ile Tyr Ala Phe Asn Ala Asp Phe Gln Lys Val
        355                 360                 365

ttt gcc cag ctg ctg ggg tgc agc cac ttc tgc tcc cgc acg ccg gtg     1152
Phe Ala Gln Leu Leu Gly Cys Ser His Phe Cys Ser Arg Thr Pro Val
    370                 375                 380

gag acg gtg aac atc agc aat gag ctc atc tcc tac aac caa gac atc     1200
Glu Thr Val Asn Ile Ser Asn Glu Leu Ile Ser Tyr Asn Gln Asp Ile
385                 390                 395                 400

gtc ttc cac aag gaa atc gca gct gcc tac atc cac atg atg ccc aac     1248
Val Phe His Lys Glu Ile Ala Ala Ala Tyr Ile His Met Met Pro Asn
                405                 410                 415

gcc gtt acc ccc ggc aac cgg gag gtg gac aac gac gag gag gag ggt     1296
Ala Val Thr Pro Gly Asn Arg Glu Val Asp Asn Asp Glu Glu Glu Gly
            420                 425                 430

cct ttc gat cgc atg ttc cag atc tat cag acg tcc cca gat ggt gac     1344
Pro Phe Asp Arg Met Phe Gln Ile Tyr Gln Thr Ser Pro Asp Gly Asp
        435                 440                 445

cct gtt gct gag tct gtc tgg gag ctg gac tgc gag ggg gag att tct     1392
Pro Val Ala Glu Ser Val Trp Glu Leu Asp Cys Glu Gly Glu Ile Ser
    450                 455                 460

tta gac aaa ata aca cct ttc acc ccg aat gga ttc cat taa             1434
Leu Asp Lys Ile Thr Pro Phe Thr Pro Asn Gly Phe His
465                 470                 475
```

```
<210> SEQ ID NO 8
<211> LENGTH: 477
<212> TYPE: PRT
<213> ORGANISM: Homo sapiens

<400> SEQUENCE: 8

Met Leu Pro Pro Gly Ser Asn Gly Thr Ala Tyr Pro Gly Gln Phe Ala
1               5                   10                  15

Leu Tyr Gln Gln Leu Ala Gln Gly Asn Ala Val Gly Gly Ser Ala Gly
            20                  25                  30

Ala Pro Pro Leu Gly Pro Ser Gln Val Val Thr Ala Cys Leu Leu Thr
        35                  40                  45

Leu Leu Ile Ile Trp Thr Leu Leu Gly Asn Val Leu Val Cys Ala Ala
    50                  55                  60

Ile Val Arg Ser Arg His Leu Arg Ala Asn Met Thr Asn Val Phe Ile
65                  70                  75                  80

Val Ser Leu Ala Val Ser Asp Leu Phe Val Ala Leu Leu Val Met Pro
                85                  90                  95

Trp Lys Ala Val Ala Glu Val Ala Gly Tyr Trp Pro Phe Gly Ala Phe
            100                 105                 110

Cys Asp Val Trp Val Ala Phe Asp Ile Met Cys Ser Thr Ala Ser Ile
        115                 120                 125

Leu Asn Leu Cys Val Ile Ser Val Asp Arg Tyr Trp Ala Ile Ser Arg
```

-continued

```
    130                 135                 140

Pro Phe Arg Tyr Lys Arg Lys Met Thr Gln Arg Met Ala Leu Val Met
145                 150                 155                 160

Val Gly Leu Ala Trp Thr Leu Ser Ile Leu Ile Ser Phe Ile Pro Val
                165                 170                 175

Gln Leu Asn Trp His Arg Asp Gln Ala Ala Ser Trp Gly Gly Leu Asp
            180                 185                 190

Leu Pro Asn Asn Leu Ala Asn Trp Thr Pro Trp Glu Glu Asp Phe Trp
        195                 200                 205

Glu Pro Asp Val Asn Ala Glu Asn Cys Asp Ser Ser Leu Asn Arg Thr
    210                 215                 220

Tyr Ala Ile Ser Ser Ser Leu Ile Ser Phe Tyr Ile Pro Val Ala Ile
225                 230                 235                 240

Met Ile Val Thr Tyr Thr Arg Ile Tyr Arg Ile Ala Gln Val Gln Ile
                245                 250                 255

Arg Arg Ile Ser Ser Leu Glu Arg Ala Ala Glu His Ala Gln Ser Cys
            260                 265                 270

Arg Ser Ser Ala Ala Cys Ala Pro Asp Thr Ser Leu Arg Ala Ser Ile
        275                 280                 285

Lys Lys Glu Thr Lys Val Leu Lys Thr Leu Ser Val Ile Met Gly Val
    290                 295                 300

Phe Val Cys Cys Trp Leu Pro Phe Phe Ile Leu Asn Cys Met Val Pro
305                 310                 315                 320

Phe Cys Ser Gly His Pro Glu Gly Pro Pro Ala Gly Phe Pro Cys Val
                325                 330                 335

Ser Glu Thr Thr Phe Asp Val Phe Val Trp Phe Gly Trp Ala Asn Ser
            340                 345                 350

Ser Leu Asn Pro Val Ile Tyr Ala Phe Asn Ala Asp Phe Gln Lys Val
        355                 360                 365

Phe Ala Gln Leu Leu Gly Cys Ser His Phe Cys Ser Arg Thr Pro Val
    370                 375                 380

Glu Thr Val Asn Ile Ser Asn Glu Leu Ile Ser Tyr Asn Gln Asp Ile
385                 390                 395                 400

Val Phe His Lys Glu Ile Ala Ala Ala Tyr Ile His Met Met Pro Asn
                405                 410                 415

Ala Val Thr Pro Gly Asn Arg Glu Val Asp Asn Asp Glu Glu Glu Gly
            420                 425                 430

Pro Phe Asp Arg Met Phe Gln Ile Tyr Gln Thr Ser Pro Asp Gly Asp
        435                 440                 445

Pro Val Ala Glu Ser Val Trp Glu Leu Asp Cys Glu Gly Glu Ile Ser
    450                 455                 460

Leu Asp Lys Ile Thr Pro Phe Thr Pro Asn Gly Phe His
465                 470                 475


<210> SEQ ID NO 9
<211> LENGTH: 1673
<212> TYPE: DNA
<213> ORGANISM: Homo sapiens
<220> FEATURE:
<221> NAME/KEY: CDS
<222> LOCATION: (148)..(1581)
<223> OTHER INFORMATION:

<400> SEQUENCE: 9

cccggcgcag ctcatggtga gcgcctctgg ggctcgaggg tcccttggct gagggggcgc     60
```

-continued

```
atcctcgggg tgcccgatgg ggctgcctgg gggtcgcagg gctgaagttg ggatcgcgca    120

caaaccgacc ctgcagtcca gcccgaa atg ctg ccg cca ggc agc aac ggc acc    174
                              Met Leu Pro Pro Gly Ser Asn Gly Thr
                              1               5

gcg tac ccg ggg cag ttc gct cta tac cag cag ctg gcg cag ggg aac      222
Ala Tyr Pro Gly Gln Phe Ala Leu Tyr Gln Gln Leu Ala Gln Gly Asn
10                  15                  20                  25

gcc gtg ggg ggc tcg gcg ggg gca ccg cca ctg ggg ccc tca cag gtg      270
Ala Val Gly Gly Ser Ala Gly Ala Pro Pro Leu Gly Pro Ser Gln Val
                30                  35                  40

gtc acc gcc tgc ctg ctg acc cta ctc atc atc tgg acc ctg ctg ggc      318
Val Thr Ala Cys Leu Leu Thr Leu Leu Ile Ile Trp Thr Leu Leu Gly
            45                  50                  55

aac gtg ctg gtg tgc gca gcc atc gtg cgg agc cgc cac ctg cgc gcc      366
Asn Val Leu Val Cys Ala Ala Ile Val Arg Ser Arg His Leu Arg Ala
        60                  65                  70

aac atg acc aac gtc ttc atc gtg tct ctg gcc gtg tct gac ctt ttc      414
Asn Met Thr Asn Val Phe Ile Val Ser Leu Ala Val Ser Asp Leu Phe
    75                  80                  85

gtg gcg ctg ctg gtc atg ccc tgg aag gca gtc gcc gag gtg gcc ggt      462
Val Ala Leu Leu Val Met Pro Trp Lys Ala Val Ala Glu Val Ala Gly
90                  95                  100                 105

tac tgg ccc ttt gga gcg ttc tgc gac gtc tgg gtg gcc ttc gac atc      510
Tyr Trp Pro Phe Gly Ala Phe Cys Asp Val Trp Val Ala Phe Asp Ile
                110                 115                 120

atg tgc tcc act gcc tcc atc ctg aac ctg tgc gtc atc agc gtg gac      558
Met Cys Ser Thr Ala Ser Ile Leu Asn Leu Cys Val Ile Ser Val Asp
            125                 130                 135

cgc tac tgg gcc atc tcc agg ccc ttc cgc tac aag cgc aag atg act      606
Arg Tyr Trp Ala Ile Ser Arg Pro Phe Arg Tyr Lys Arg Lys Met Thr
        140                 145                 150

cag cgc atg gcc ttg gtc atg gtc ggc ctg gca tgg acc ttg tcc atc      654
Gln Arg Met Ala Leu Val Met Val Gly Leu Ala Trp Thr Leu Ser Ile
    155                 160                 165

ctc atc tcc ttc att ccg gtc cag ctc aac tgg cac agg gac cag gcg      702
Leu Ile Ser Phe Ile Pro Val Gln Leu Asn Trp His Arg Asp Gln Ala
170                 175                 180                 185

gcc tct tgg ggc ggg ctg gac ctg cca aac aac ctg gcc aac tgg acg      750
Ala Ser Trp Gly Gly Leu Asp Leu Pro Asn Asn Leu Ala Asn Trp Thr
                190                 195                 200

ccc tgg gag gag gac ttt tgg gag ccc gac gtg aat gca gag aac tgt      798
Pro Trp Glu Glu Asp Phe Trp Glu Pro Asp Val Asn Ala Glu Asn Cys
            205                 210                 215

gac tcc agc ctg aat cga acc tac gcc atc tct tcc tcg ctc atc agc      846
Asp Ser Ser Leu Asn Arg Thr Tyr Ala Ile Ser Ser Ser Leu Ile Ser
        220                 225                 230

ttc tac atc ccc gtt gcc atc atg atc gtg acc tac acg cgc atc tac      894
Phe Tyr Ile Pro Val Ala Ile Met Ile Val Thr Tyr Thr Arg Ile Tyr
    235                 240                 245

cgc atc gcc cag gtg cag atc cgc agg att tcc tcc ctg gag agg gcc      942
Arg Ile Ala Gln Val Gln Ile Arg Arg Ile Ser Ser Leu Glu Arg Ala
250                 255                 260                 265

gca gag cac gcg cag agc tgc cgg agc agc gca gcc tgc gcg ccc gac      990
Ala Glu His Ala Gln Ser Cys Arg Ser Ser Ala Ala Cys Ala Pro Asp
                270                 275                 280

acc agc ctg cgc gct tcc atc aag aag gag acc aag gtt ctc aag acc     1038
Thr Ser Leu Arg Ala Ser Ile Lys Lys Glu Thr Lys Val Leu Lys Thr
            285                 290                 295

ctg tcg gtg atc atg ggg gtc ttc gtg tgt tgc tgg ctg ccc ttc ttc     1086
```

-continued

```
Leu Ser Val Ile Met Gly Val Phe Val Cys Cys Trp Leu Pro Phe Phe
        300                 305                 310

atc ctt aac tgc atg gtc cct ttc tgc agt gga cac cct gaa ggc cct      1134
Ile Leu Asn Cys Met Val Pro Phe Cys Ser Gly His Pro Glu Gly Pro
    315                 320                 325

ccg gcc ggc ttc ccc tgc gtc agt gag acc acc ttc gac gtc ttc gtc      1182
Pro Ala Gly Phe Pro Cys Val Ser Glu Thr Thr Phe Asp Val Phe Val
330                 335                 340                 345

tgg ttc ggc tgg gct aac tcc tca ctc aac ccc gtc atc tat gcc ttc      1230
Trp Phe Gly Trp Ala Asn Ser Ser Leu Asn Pro Val Ile Tyr Ala Phe
                350                 355                 360

aac gcc gac ttt cag aag gtg ttt gcc cag ctg ctg ggg tgc agc cac      1278
Asn Ala Asp Phe Gln Lys Val Phe Ala Gln Leu Leu Gly Cys Ser His
            365                 370                 375

ttc tgc tcc cgc acg ccg gtg gag acg gtg aac atc agc aat gag ctc      1326
Phe Cys Ser Arg Thr Pro Val Glu Thr Val Asn Ile Ser Asn Glu Leu
        380                 385                 390

atc tcc tac aac caa gac atc gtc ttc cac aag gaa atc gca gct gcc      1374
Ile Ser Tyr Asn Gln Asp Ile Val Phe His Lys Glu Ile Ala Ala Ala
    395                 400                 405

tac atc cac atg atg ccc aac gcc gtt acc ccc ggc aac cgg gag gtg      1422
Tyr Ile His Met Met Pro Asn Ala Val Thr Pro Gly Asn Arg Glu Val
410                 415                 420                 425

gac aac gac gag gag gag ggt cct ttc gat cgc atg ttc cag atc tat      1470
Asp Asn Asp Glu Glu Glu Gly Pro Phe Asp Arg Met Phe Gln Ile Tyr
                430                 435                 440

cag acg tcc cca gat ggt gac cct gtt gct gag tct gtc tgg gag ctg      1518
Gln Thr Ser Pro Asp Gly Asp Pro Val Ala Glu Ser Val Trp Glu Leu
            445                 450                 455

gac tgc gag ggg gag att tct tta gac aaa ata aca cct ttc acc ccg      1566
Asp Cys Glu Gly Glu Ile Ser Leu Asp Lys Ile Thr Pro Phe Thr Pro
        460                 465                 470

aat gga ttc cat taa actgcattaa gaaacccccct catggatctg cataaccgca      1621
Asn Gly Phe His
    475

cagacactga caagcacgca cacacacgca aatacatgcc tttccagtac tg            1673


<210> SEQ ID NO 10
<211> LENGTH: 477
<212> TYPE: PRT
<213> ORGANISM: Homo sapiens

<400> SEQUENCE: 10

Met Leu Pro Pro Gly Ser Asn Gly Thr Ala Tyr Pro Gly Gln Phe Ala
1               5                   10                  15

Leu Tyr Gln Gln Leu Ala Gln Gly Asn Ala Val Gly Gly Ser Ala Gly
            20                  25                  30

Ala Pro Pro Leu Gly Pro Ser Gln Val Val Thr Ala Cys Leu Leu Thr
        35                  40                  45

Leu Leu Ile Ile Trp Thr Leu Leu Gly Asn Val Leu Val Cys Ala Ala
    50                  55                  60

Ile Val Arg Ser Arg His Leu Arg Ala Asn Met Thr Asn Val Phe Ile
65                  70                  75                  80

Val Ser Leu Ala Val Ser Asp Leu Phe Val Ala Leu Leu Val Met Pro
                85                  90                  95

Trp Lys Ala Val Ala Glu Val Ala Gly Tyr Trp Pro Phe Gly Ala Phe
            100                 105                 110

Cys Asp Val Trp Val Ala Phe Asp Ile Met Cys Ser Thr Ala Ser Ile
```

-continued

```
        115                 120                 125

Leu Asn Leu Cys Val Ile Ser Val Asp Arg Tyr Trp Ala Ile Ser Arg
    130                 135                 140

Pro Phe Arg Tyr Lys Arg Lys Met Thr Gln Arg Met Ala Leu Val Met
145                 150                 155                 160

Val Gly Leu Ala Trp Thr Leu Ser Ile Leu Ile Ser Phe Ile Pro Val
                165                 170                 175

Gln Leu Asn Trp His Arg Asp Gln Ala Ala Ser Trp Gly Gly Leu Asp
            180                 185                 190

Leu Pro Asn Asn Leu Ala Asn Trp Thr Pro Trp Glu Glu Asp Phe Trp
        195                 200                 205

Glu Pro Asp Val Asn Ala Glu Asn Cys Asp Ser Ser Leu Asn Arg Thr
    210                 215                 220

Tyr Ala Ile Ser Ser Ser Leu Ile Ser Phe Tyr Ile Pro Val Ala Ile
225                 230                 235                 240

Met Ile Val Thr Tyr Thr Arg Ile Tyr Arg Ile Ala Gln Val Gln Ile
                245                 250                 255

Arg Arg Ile Ser Ser Leu Glu Arg Ala Ala Glu His Ala Gln Ser Cys
            260                 265                 270

Arg Ser Ser Ala Ala Cys Ala Pro Asp Thr Ser Leu Arg Ala Ser Ile
        275                 280                 285

Lys Lys Glu Thr Lys Val Leu Lys Thr Leu Ser Val Ile Met Gly Val
    290                 295                 300

Phe Val Cys Cys Trp Leu Pro Phe Phe Ile Leu Asn Cys Met Val Pro
305                 310                 315                 320

Phe Cys Ser Gly His Pro Glu Gly Pro Pro Ala Gly Phe Pro Cys Val
                325                 330                 335

Ser Glu Thr Thr Phe Asp Val Phe Val Trp Phe Gly Trp Ala Asn Ser
            340                 345                 350

Ser Leu Asn Pro Val Ile Tyr Ala Phe Asn Ala Asp Phe Gln Lys Val
        355                 360                 365

Phe Ala Gln Leu Leu Gly Cys Ser His Phe Cys Ser Arg Thr Pro Val
    370                 375                 380

Glu Thr Val Asn Ile Ser Asn Glu Leu Ile Ser Tyr Asn Gln Asp Ile
385                 390                 395                 400

Val Phe His Lys Glu Ile Ala Ala Ala Tyr Ile His Met Met Pro Asn
                405                 410                 415

Ala Val Thr Pro Gly Asn Arg Glu Val Asp Asn Asp Glu Glu Glu Gly
            420                 425                 430

Pro Phe Asp Arg Met Phe Gln Ile Tyr Gln Thr Ser Pro Asp Gly Asp
        435                 440                 445

Pro Val Ala Glu Ser Val Trp Glu Leu Asp Cys Glu Gly Glu Ile Ser
    450                 455                 460

Leu Asp Lys Ile Thr Pro Phe Thr Pro Asn Gly Phe His
465                 470                 475
```

<210> SEQ ID NO 11
<211> LENGTH: 1673
<212> TYPE: DNA
<213> ORGANISM: Homo sapiens
<220> FEATURE:
<221> NAME/KEY: CDS
<222> LOCATION: (148)..(546)
<223> OTHER INFORMATION:

<400> SEQUENCE: 11

-continued

```
cccggcgcag ctcatggtga gcgcctctgg ggctcgaggg tcccttggct gagggggcgc     60

atcctcgggg tgcccgatgg ggctgcctgg gggtcgcagg gctgaagttg ggatcgcgca    120

caaaccgacc ctgcagtcca gcccgaa atg ctg ccg cca ggc agc aac ggc acc    174
                              Met Leu Pro Pro Gly Ser Asn Gly Thr
                              1               5

gcg tac ccg ggg cag ttc gct cta tac cag cag ctg gcg cag ggg aac      222
Ala Tyr Pro Gly Gln Phe Ala Leu Tyr Gln Gln Leu Ala Gln Gly Asn
10                  15                  20                  25

gcc gtg ggg ggc tcg gcg ggg gca ccg cca ctg ggg ccc tca cag gtg      270
Ala Val Gly Gly Ser Ala Gly Ala Pro Pro Leu Gly Pro Ser Gln Val
                30                  35                  40

gtc acc gcc tgc ctg ctg acc cta ctc atc atc tgg acc ctg ctg ggc      318
Val Thr Ala Cys Leu Leu Thr Leu Leu Ile Ile Trp Thr Leu Leu Gly
            45                  50                  55

aac gtg ctg gtg tgc gca gcc atc gtg cgg agc cgc cac ctg cgc gcc      366
Asn Val Leu Val Cys Ala Ala Ile Val Arg Ser Arg His Leu Arg Ala
        60                  65                  70

aac atg acc aac gtc ttc atc gtg tct ctg gcc gtg tct gac ctt ttc      414
Asn Met Thr Asn Val Phe Ile Val Ser Leu Ala Val Ser Asp Leu Phe
    75                  80                  85

gtg gcg ctg ctg gtc atg ccc tgg aag gca gtc gcc gag gtg gcc ggt      462
Val Ala Leu Leu Val Met Pro Trp Lys Ala Val Ala Glu Val Ala Gly
90                  95                  100                 105

tac tgg ccc ttt gga gcg ttc tgc gac gtc tgg gtg gcc ttc gac atc      510
Tyr Trp Pro Phe Gly Ala Phe Cys Asp Val Trp Val Ala Phe Asp Ile
                110                 115                 120

atg tgc tcc act gcc tcc atc ctg aac ctg tgc gtc atcagcgtgg           556
Met Cys Ser Thr Ala Ser Ile Leu Asn Leu Cys Val
            125                 130

accgctactg ggccatctcc aggcccttcc gctacaagcg caagatgact cagcgcatgg    616

ccttggtcat ggtcggcctg gcatggacct tgtccatcct catctccttc attccggtcc    676

agctcaactg gcacagggac caggcggcct cttggggcgg gctggacctg ccaaacaacc    736

tggccaactg gacgccctgg gaggaggact tttgggagcc cgacgtgaat gcagagaact    796

gtgactccag cctgaatcga acctacgcca tctcttcctc gctcatcagc ttctacatcc    856

ccgttgccat catgatcgtg acctacacgc gcatctaccg catcgcccag gtgcagatcc    916

gcaggatttc ctccctggag agggccgcag agcacgcgca gagctgccgg agcagcgcag    976

cctgcgcgcc cgacaccagc ctgcgcgctt ccatcaagaa ggagaccaag gttctcaaga   1036

ccctgtcggt gatcatgggg gtcttcgtgt gttgctggct gcccttcttc atccttaact   1096

gcatggtccc tttctgcagt ggacaccctg aaggccctcc ggccggcttc ccctgcgtca   1156

gtgagaccac cttcgacgtc ttcgtctggt tcggctgggc taactcctca ctcaaccccg   1216

tcatctatgc cttcaacgcc gactttcaga aggtgtttgc ccagctgctg ggtcgagcc    1276

acttctgctc ccgcacgccg gtggagacgg tgaacatcag caatgagctc atctcctaca   1336

accaagacat cgtcttccac aaggaaatcg cagctgccta catccacatg atgcccaacg   1396

ccgttacccc cggcaaccgg gaggtggaca acgacgagga ggagggtcct ttcgatcgca   1456

tgttccagat ctatcagacg tccccagatg gtgaccctgt tgctgagtct gtctgggagc   1516

tggactgcga gggggagatt tctttagaca aaataacacc tttcaccccg aatggattcc   1576

attaaactgc attaagaaac cccctcatgg atctgcataa ccgcacagac actgacaagc   1636

acgcacacac acgcaaatac atgcctttcc agtactg                            1673
```

-continued

<210> SEQ ID NO 12
<211> LENGTH: 133
<212> TYPE: PRT
<213> ORGANISM: Homo sapiens

<400> SEQUENCE: 12

```
Met Leu Pro Pro Gly Ser Asn Gly Thr Ala Tyr Pro Gly Gln Phe Ala
1               5                   10                  15

Leu Tyr Gln Gln Leu Ala Gln Gly Asn Ala Val Gly Gly Ser Ala Gly
            20                  25                  30

Ala Pro Pro Leu Gly Pro Ser Gln Val Val Thr Ala Cys Leu Leu Thr
        35                  40                  45

Leu Leu Ile Ile Trp Thr Leu Leu Gly Asn Val Leu Val Cys Ala Ala
    50                  55                  60

Ile Val Arg Ser Arg His Leu Arg Ala Asn Met Thr Asn Val Phe Ile
65                  70                  75                  80

Val Ser Leu Ala Val Ser Asp Leu Phe Val Ala Leu Leu Val Met Pro
                85                  90                  95

Trp Lys Ala Val Ala Glu Val Ala Gly Tyr Trp Pro Phe Gly Ala Phe
            100                 105                 110

Cys Asp Val Trp Val Ala Phe Asp Ile Met Cys Ser Thr Ala Ser Ile
        115                 120                 125

Leu Asn Leu Cys Val
    130
```

<210> SEQ ID NO 13
<211> LENGTH: 1439
<212> TYPE: DNA
<213> ORGANISM: Homo sapiens
<220> FEATURE:
<221> NAME/KEY: CDS
<222> LOCATION: (1)..(465)
<223> OTHER INFORMATION:

<400> SEQUENCE: 13

```
atg ctg ccg cca agg agc aac ggc acc gcg tac ccg ggg cag tta gcg       48
Met Leu Pro Pro Arg Ser Asn Gly Thr Ala Tyr Pro Gly Gln Leu Ala
1               5                   10                  15

ctg tac cag cag ctg gcg cag ggg aat gcc gtg ggg ggc tcg gcg ggg       96
Leu Tyr Gln Gln Leu Ala Gln Gly Asn Ala Val Gly Gly Ser Ala Gly
            20                  25                  30

gca ccg cca ctg ggg ccc gtg cag gtg gtc acc gcc tgc ctg ctg acc      144
Ala Pro Pro Leu Gly Pro Val Gln Val Val Thr Ala Cys Leu Leu Thr
        35                  40                  45

cta ctc atc atc tgg acc ttg ctg ggc aac gtg ctg gtg tcc gca gcc      192
Leu Leu Ile Ile Trp Thr Leu Leu Gly Asn Val Leu Val Ser Ala Ala
    50                  55                  60

atc gtg cgg agc cgc cac ctg cgc gcc aag atg acc aac gtc ttc atc      240
Ile Val Arg Ser Arg His Leu Arg Ala Lys Met Thr Asn Val Phe Ile
65                  70                  75                  80

gtg tct cta cct gtg tca gac ctc ttc gtg gcg ctg ctg gtc atg tcc      288
Val Ser Leu Pro Val Ser Asp Leu Phe Val Ala Leu Leu Val Met Ser
                85                  90                  95

tgg aag gca gtc gcc gag gtg gcc ggt tac tgg ccc ttt gaa gcg ttc      336
Trp Lys Ala Val Ala Glu Val Ala Gly Tyr Trp Pro Phe Glu Ala Phe
            100                 105                 110

tgc gac gtc tgg gtg gcc ttc gac atc atg tgc tcc acc gcc tcc atc      384
Cys Asp Val Trp Val Ala Phe Asp Ile Met Cys Ser Thr Ala Ser Ile
        115                 120                 125
```

-continued

```
ctg aac ctg tgc gtc agc agg tca tca gcg tgg ccc gct act ggg cca      432
Leu Asn Leu Cys Val Ser Arg Ser Ser Ala Trp Pro Ala Thr Gly Pro
    130                 135                 140

tct cca ggc cct tcc gct acg agc gca aga tga cccagcgcat ggccttggtc    485
Ser Pro Gly Pro Ser Ala Thr Ser Ala Arg
145                 150

atggtccgcc cggcctggac cttgtccagc ctcatctcct tcattccggt ccagctcaac    545

tggcacaggg accaggcggt ctcttgaggt gggctggacc tgccaaacaa cctggccaac    605

tggacgccct gggaggaggc cgtttgggag cccgacgtga gggcagagaa ctgtgactcc    665

agcctgaatc gaacctacgc catctcttcc tcgctcatca gcttctacat ccccatggcc    725

atcatgatcg tgacctacac gcgcatctac cgcatcgccc aggtgcagat ccgcaggatt    785

tcctccctgg agagggccgc agagcacgtg cagagctgcc ggagcagcgc aggctgcgcg    845

cccgacacca gcctgcggtt ttccatcaag aaggagaccg aggttctcaa gaccctgtcg    905

gtgatcatgg gggtcttcgt gtgttgctgg ctgcccttct tcatccttaa ctgcatggtc    965

cctttctgca gtggacaccc caaagcctcc ggccggcttc ccctgcgtca gtgagaccac   1025

attcgacgtc ttcatctggt tctgctgggc caactcctca ctcaacccag tcactatgcc   1085

ttcaacgccg acttccggaa ggtgtttgcc cagctgctgg ggtgcagcca cgtctgctcc   1145

cgcacgccgg tggagacggt gaacatcagc aatgagctca tctcctacaa ccaagacacg   1205

gtcttccaca aggaaatcgc agctgcctac atccacatga tgcccaacgc cgttaccccc   1265

ggggaccggg aggtggacaa cgatgaggag gaggagagtc ctttcgatcg catgtcccag   1325

atctatcaga catccccaga tggtgaccct gttgcagagt ctgtctgaga gctggacggc   1385

gagggggaga tttctttaga caaaataaca cctttcaccc caaatggatt ccat         1439


<210> SEQ ID NO 14
<211> LENGTH: 154
<212> TYPE: PRT
<213> ORGANISM: Homo sapiens

<400> SEQUENCE: 14

Met Leu Pro Pro Arg Ser Asn Gly Thr Ala Tyr Pro Gly Gln Leu Ala
1               5                   10                  15

Leu Tyr Gln Gln Leu Ala Gln Gly Asn Ala Val Gly Gly Ser Ala Gly
            20                  25                  30

Ala Pro Pro Leu Gly Pro Val Gln Val Val Thr Ala Cys Leu Leu Thr
        35                  40                  45

Leu Leu Ile Ile Trp Thr Leu Leu Gly Asn Val Leu Val Ser Ala Ala
    50                  55                  60

Ile Val Arg Ser Arg His Leu Arg Ala Lys Met Thr Asn Val Phe Ile
65                  70                  75                  80

Val Ser Leu Pro Val Ser Asp Leu Phe Val Ala Leu Leu Val Met Ser
                85                  90                  95

Trp Lys Ala Val Ala Glu Val Ala Gly Tyr Trp Pro Phe Glu Ala Phe
            100                 105                 110

Cys Asp Val Trp Val Ala Phe Asp Ile Met Cys Ser Thr Ala Ser Ile
        115                 120                 125

Leu Asn Leu Cys Val Ser Arg Ser Ser Ala Trp Pro Ala Thr Gly Pro
    130                 135                 140

Ser Pro Gly Pro Ser Ala Thr Ser Ala Arg
145                 150
```

-continued

```
<210> SEQ ID NO 15
<211> LENGTH: 1409
<212> TYPE: DNA
<213> ORGANISM: Rhesus macaque
<220> FEATURE:
<221> NAME/KEY: CDS
<222> LOCATION: (51)..(1391)
<223> OTHER INFORMATION:

<400> SEQUENCE: 15

ttaggaactt gaggggtgtc agagcccctg atgtgctttc ccttaggaag atg agg        56
                                                      Met Arg
                                                      1

act ctg aac acc tct gcc atg gac ggg act ggg ctg gtg gtg gag agg      104
Thr Leu Asn Thr Ser Ala Met Asp Gly Thr Gly Leu Val Val Glu Arg
        5                   10                  15

gac ttc tct gtt cgt atc ctc act gcc tgt ttc ctg tcg ctg ctc atc      152
Asp Phe Ser Val Arg Ile Leu Thr Ala Cys Phe Leu Ser Leu Leu Ile
    20                  25                  30

ctg tcc acg ctc ctg ggg aac acg ctg gtc tgt gct gcc gtt atc agg      200
Leu Ser Thr Leu Leu Gly Asn Thr Leu Val Cys Ala Ala Val Ile Arg
35                  40                  45                  50

ttc cga cac ctg cgg tcc aag gtt acc aac ttc ttt gtc atc tcc ttg      248
Phe Arg His Leu Arg Ser Lys Val Thr Asn Phe Phe Val Ile Ser Leu
                55                  60                  65

gcc gtg tca gat ctc ttg gtg gcc gtc ttg gtc atg ccc tgg aaa gca      296
Ala Val Ser Asp Leu Leu Val Ala Val Leu Val Met Pro Trp Lys Ala
            70                  75                  80

gtg gct gag att gct ggc ttc tgg ccc ttt ggg tcc ttc tgt aac atc      344
Val Ala Glu Ile Ala Gly Phe Trp Pro Phe Gly Ser Phe Cys Asn Ile
        85                  90                  95

tgg gtg gcc ttt gac atc atg tgc tcc acc gcg tcc atc ctc aac ctc      392
Trp Val Ala Phe Asp Ile Met Cys Ser Thr Ala Ser Ile Leu Asn Leu
    100                 105                 110

tgt gtg atc agc gtg gac agg tac tgg gct atc tcc agc cct ttc cgg      440
Cys Val Ile Ser Val Asp Arg Tyr Trp Ala Ile Ser Ser Pro Phe Arg
115                 120                 125                 130

tat gag aga aag atg acc ccc aag gca gcc ttc atc ctg atc agt gtg      488
Tyr Glu Arg Lys Met Thr Pro Lys Ala Ala Phe Ile Leu Ile Ser Val
                135                 140                 145

gca tgg acc ttg tct gta ctc atc tcc ttc atc cca gtg cag ctc agc      536
Ala Trp Thr Leu Ser Val Leu Ile Ser Phe Ile Pro Val Gln Leu Ser
            150                 155                 160

tgg cac aag gca aaa ccc acc agc ccc tct gat ggg aat gcc act tcc      584
Trp His Lys Ala Lys Pro Thr Ser Pro Ser Asp Gly Asn Ala Thr Ser
        165                 170                 175

ctg gct gag acc ata gac aac tgt gat tcc agc ctc agc agg aca tat      632
Leu Ala Glu Thr Ile Asp Asn Cys Asp Ser Ser Leu Ser Arg Thr Tyr
    180                 185                 190

gcc atc tca tcc tct gta ata agt ttt tac atc cct gtg gcc atc atg      680
Ala Ile Ser Ser Ser Val Ile Ser Phe Tyr Ile Pro Val Ala Ile Met
195                 200                 205                 210

att gtc acg tac acc agg atc tac agg att gct cag aaa caa ata cgg      728
Ile Val Thr Tyr Thr Arg Ile Tyr Arg Ile Ala Gln Lys Gln Ile Arg
                215                 220                 225

cgc att gcg gcc ttg gag agg gca gca gtc cat gcc aag aat tgc cag      776
Arg Ile Ala Ala Leu Glu Arg Ala Ala Val His Ala Lys Asn Cys Gln
            230                 235                 240

acc acc aca ggt aat gga aag cct gtc gaa tgt tct caa ccg gaa agt      824
Thr Thr Thr Gly Asn Gly Lys Pro Val Glu Cys Ser Gln Pro Glu Ser
        245                 250                 255
```

-continued

```
tct ttt aag atg tcc ttc aaa aga gaa act aaa gtc ctg aag act ctg      872
Ser Phe Lys Met Ser Phe Lys Arg Glu Thr Lys Val Leu Lys Thr Leu
    260                 265                 270

tca gtg atc atg ggc gtg ttt gtg tgc tgt tgg cta cct ttc ttc atc      920
Ser Val Ile Met Gly Val Phe Val Cys Cys Trp Leu Pro Phe Phe Ile
275                 280                 285                 290

ctg aac tgc att ttg ccg ttc tgc ggg tct ggg gag acg cag ccc ttc      968
Leu Asn Cys Ile Leu Pro Phe Cys Gly Ser Gly Glu Thr Gln Pro Phe
                295                 300                 305

tgc atc gat tcc atc acc ttt gac gtg ttt gtg tgg ttt ggg tgg gct     1016
Cys Ile Asp Ser Ile Thr Phe Asp Val Phe Val Trp Phe Gly Trp Ala
            310                 315                 320

aat tca tcc ttg aac ccc atc att tat gcc ttt aat gct gat ttt cgg     1064
Asn Ser Ser Leu Asn Pro Ile Ile Tyr Ala Phe Asn Ala Asp Phe Arg
        325                 330                 335

aag gca ttt tca acc ctc tta gga tgc tac aga ctt tgc ccg gcg aca     1112
Lys Ala Phe Ser Thr Leu Leu Gly Cys Tyr Arg Leu Cys Pro Ala Thr
    340                 345                 350

aat aat gcc ata gag acg gtg agt atc aat aac aat ggg gcc gcg atg     1160
Asn Asn Ala Ile Glu Thr Val Ser Ile Asn Asn Asn Gly Ala Ala Met
355                 360                 365                 370

ttt tcc agc cat cac gag cca cga ggt tct atc tcc aag gag tgc aat     1208
Phe Ser Ser His His Glu Pro Arg Gly Ser Ile Ser Lys Glu Cys Asn
                375                 380                 385

ctg gtt tac ctg atc cca cat gct gtg ggc tcc tct gag gac ctg aaa     1256
Leu Val Tyr Leu Ile Pro His Ala Val Gly Ser Ser Glu Asp Leu Lys
            390                 395                 400

aag gag gag gca gct gga atc gcc aga ccc ttg gag aag ctg tcc cca     1304
Lys Glu Glu Ala Ala Gly Ile Ala Arg Pro Leu Glu Lys Leu Ser Pro
        405                 410                 415

gcc cta tcg gtc ata ttg gac tat gac act gac gtc tct ctg gag aag     1352
Ala Leu Ser Val Ile Leu Asp Tyr Asp Thr Asp Val Ser Leu Glu Lys
    420                 425                 430

atc caa ccc atc aca caa aac gga cag cac cca act tga actcccagat      1401
Ile Gln Pro Ile Thr Gln Asn Gly Gln His Pro Thr
435                 440                 445

gaatcctg                                                            1409


<210> SEQ ID NO 16
<211> LENGTH: 446
<212> TYPE: PRT
<213> ORGANISM: Rhesus macaque

<400> SEQUENCE: 16

Met Arg Thr Leu Asn Thr Ser Ala Met Asp Gly Thr Gly Leu Val Val
1               5                   10                  15

Glu Arg Asp Phe Ser Val Arg Ile Leu Thr Ala Cys Phe Leu Ser Leu
            20                  25                  30

Leu Ile Leu Ser Thr Leu Leu Gly Asn Thr Leu Val Cys Ala Ala Val
        35                  40                  45

Ile Arg Phe Arg His Leu Arg Ser Lys Val Thr Asn Phe Phe Val Ile
    50                  55                  60

Ser Leu Ala Val Ser Asp Leu Leu Val Ala Val Leu Val Met Pro Trp
65                  70                  75                  80

Lys Ala Val Ala Glu Ile Ala Gly Phe Trp Pro Phe Gly Ser Phe Cys
                85                  90                  95

Asn Ile Trp Val Ala Phe Asp Ile Met Cys Ser Thr Ala Ser Ile Leu
            100                 105                 110
```

-continued

```
Asn Leu Cys Val Ile Ser Val Asp Arg Tyr Trp Ala Ile Ser Ser Pro
        115                 120                 125

Phe Arg Tyr Glu Arg Lys Met Thr Pro Lys Ala Ala Phe Ile Leu Ile
    130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Ala
                165                 170                 175

Thr Ser Leu Ala Glu Thr Ile Asp Asn Cys Asp Ser Ser Leu Ser Arg
            180                 185                 190

Thr Tyr Ala Ile Ser Ser Ser Val Ile Ser Phe Tyr Ile Pro Val Ala
        195                 200                 205

Ile Met Ile Val Thr Tyr Thr Arg Ile Tyr Arg Ile Ala Gln Lys Gln
    210                 215                 220

Ile Arg Arg Ile Ala Ala Leu Glu Arg Ala Ala Val His Ala Lys Asn
225                 230                 235                 240

Cys Gln Thr Thr Thr Gly Asn Gly Lys Pro Val Glu Cys Ser Gln Pro
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285

Phe Ile Leu Asn Cys Ile Leu Pro Phe Cys Gly Ser Gly Glu Thr Gln
    290                 295                 300

Pro Phe Cys Ile Asp Ser Ile Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Arg Lys Ala Phe Ser Thr Leu Leu Gly Cys Tyr Arg Leu Cys Pro
            340                 345                 350

Ala Thr Asn Asn Ala Ile Glu Thr Val Ser Ile Asn Asn Asn Gly Ala
        355                 360                 365

Ala Met Phe Ser Ser His His Glu Pro Arg Gly Ser Ile Ser Lys Glu
    370                 375                 380

Cys Asn Leu Val Tyr Leu Ile Pro His Ala Val Gly Ser Ser Glu Asp
385                 390                 395                 400

Leu Lys Lys Glu Glu Ala Ala Gly Ile Ala Arg Pro Leu Glu Lys Leu
                405                 410                 415

Ser Pro Ala Leu Ser Val Ile Leu Asp Tyr Asp Thr Asp Val Ser Leu
            420                 425                 430

Glu Lys Ile Gln Pro Ile Thr Gln Asn Gly Gln His Pro Thr
        435                 440                 445


<210> SEQ ID NO 17
<211> LENGTH: 1420
<212> TYPE: DNA
<213> ORGANISM: Gorilla gorilla
<220> FEATURE:
<221> NAME/KEY: CDS
<222> LOCATION: (2)..(313)
<223> OTHER INFORMATION:

<400> SEQUENCE: 17

g ctg ccg cca cga gac ggc acc gct tac ccg ggg cag tta gcg cta tac      49
  Leu Pro Pro Arg Asp Gly Thr Ala Tyr Pro Gly Gln Leu Ala Leu Tyr
  1               5                   10                  15
```

-continued

```
cag cag ctg gcg cag ggg aac gct gtg ggg ggc tcg gcg ggg gca ccg       97
Gln Gln Leu Ala Gln Gly Asn Ala Val Gly Gly Ser Ala Gly Ala Pro
            20                  25                  30

cca ctg ggg ccc gcg cag gtg gtc acc gcc tgc ctg ctg acc cta ctc      145
Pro Leu Gly Pro Ala Gln Val Val Thr Ala Cys Leu Leu Thr Leu Leu
        35                  40                  45

atc atc tgg acc ttg ctg ggc aac gtg ctg ttg tgc gca gcc atc gtg      193
Ile Ile Trp Thr Leu Leu Gly Asn Val Leu Leu Cys Ala Ala Ile Val
    50                  55                  60

cgg acg cgc cac ctg cgc gcc aag atg acc aac gtc ttc atc gtg tct      241
Arg Thr Arg His Leu Arg Ala Lys Met Thr Asn Val Phe Ile Val Ser
65                  70                  75                  80

ctg gct gtg tca gac ctc ttc gtg gcg ctg ctg gta ggc agt cgc cga      289
Leu Ala Val Ser Asp Leu Phe Val Ala Leu Leu Val Gly Ser Arg Arg
                85                  90                  95

ggt ggc cgg tta ctg gtc ctt tga agcgttctgc ggcatctggg tggccttgga     343
Gly Gly Arg Leu Leu Val Leu
            100

catcatgtgc tccaccgcct ccatcctgaa cctgtgcgtc agcaggtcat cagcgtggac    403

cgctactggg ccatctccag gcccttccgc tacgagcgca agatgaccca gcacatggcc    463

ttggtcatgg tcagcccggc ctggaccttg tccagcctca tctccttcat tccggtccag    523

ctcaactggc acagggacca ggcggtctct tggggcgggc tggacctgcc aaacaacctg    583

gccaactgga cgccctggga ggaggccatt tgggagcccg acgtgagggc agagaacggt    643

gactccagcc tgaatcgaac ctatgccatc tcttcctcgc tcatcagctt ctatatcccc    703

atggccatca tgatcgtgac ctacacgcgc atctaccgca tcgcccaggt gcagatccgc    763

aggatttcct ccctggagag ggccgcagag cacgggcaga gctgccggag cagcgcagcg    823

tgcgcacccg acaccagcct gcggttttcc atcaagaagg agaccgaggt tctcaagacc    883

ctgtcggtga tcatgggggt cttcgtgtgt tgctggctgc ccttcttcat ccttaactgc    943

atggtccctt tctgcagtgg acaccccaaa ggccctccgg ccggcttccc ctgcgtcagt   1003

gagaccacat tcgatgtctt cgtctggttc tgctgggcca actcctcact caacccagtc   1063

actatgcctt caacgccgac ttccggaagg tgtttgccca gctgctgggg tgcagccacg   1123

tctgctcccg cacgccggtg gagacggtga acatcagcaa tgagctcatc tcctacaacc   1183

aagacaccgt cttccacaag gaaatcgcag ctgcctacat ccacatgatg cccaacgcca   1243

ttcccaccgg cgaccgggag gtggacaacg atgaggagga gagtcctttc gatcgcatgt   1303

cccagatcta tcagatgtcc ccatatggtg accctgttgc agagtctgtc tgagagctgg   1363

actgcgaggg ggagatttct ttagacaaaa taacaccttt caccccgaat ggatttc      1420


<210> SEQ ID NO 18
<211> LENGTH: 103
<212> TYPE: PRT
<213> ORGANISM: Gorilla gorilla

<400> SEQUENCE: 18

Leu Pro Pro Arg Asp Gly Thr Ala Tyr Pro Gly Gln Leu Ala Leu Tyr
1               5                   10                  15

Gln Gln Leu Ala Gln Gly Asn Ala Val Gly Gly Ser Ala Gly Ala Pro
            20                  25                  30

Pro Leu Gly Pro Ala Gln Val Val Thr Ala Cys Leu Leu Thr Leu Leu
        35                  40                  45

Ile Ile Trp Thr Leu Leu Gly Asn Val Leu Leu Cys Ala Ala Ile Val
```

```
              50                  55                  60
Arg Thr Arg His Leu Arg Ala Lys Met Thr Asn Val Phe Ile Val Ser
 65                  70                  75                  80

Leu Ala Val Ser Asp Leu Phe Val Ala Leu Leu Val Gly Ser Arg Arg
                 85                  90                  95

Gly Gly Arg Leu Leu Val Leu
            100

<210> SEQ ID NO 19
<211> LENGTH: 6251
<212> TYPE: DNA
<213> ORGANISM: Rattus norvegicus
<220> FEATURE:
<221> NAME/KEY: CDS
<222> LOCATION: (3272)..(4612)
<223> OTHER INFORMATION:

<400> SEQUENCE: 19

gaattctttt gctggggact ggcactgcag gcaaagccat gccacctgag tcagccttcg      60

tatggctggc atcctacttt aaagagcagt ggccattgcc cagaggcttg gggacacctc     120

tccaaagcaa aagtcactag gggagtttca gtcctcaaat cgccctcacg gtcaccccca     180

ggttccgtgg ctacaatcct aagtgctact gtattgttgc ctcttttaat ttgtgtttgc     240

tggtgaaaaa tgaagaagta tggtgaaata aagctccaat cgcttagaga gcaactgcca     300

cactgtgtgt gtgtgtgtat gtgtgtgtat gtgtgtgtgt gtgtgtgtgt ggtgagaatc     360

ccctcaggtt ttacactgaa ctgactctaa agcagatgtt ctcaacttgt gaatcttgac     420

cctttggtgg ctgggggtg ggctcatatc agatagtccg tcacacattt acattataat     480

tcataacagt aacaaaatta gttatggggc agcaacaaaa taactttatg gttgggggtt     540

ctccgcctgt ggaactgtat taaagggtca cagcattggg gaagttgagg acctctgttc     600

ttaaggcatg ggttatatgt ctgatcacga gtctgtggaa ctttgtgtgt gacagcaagg     660

ctgtcagtgg gagggcagaa ctgggcgaac gggcggagga gcatctgtgt caatcatctg     720

actagtacac ccttttccga gatctgattt ctgctggcta attaggagag cttcttaggc     780

tatttagaga aaattcgagc attcagtgcg gtgtatggtt cgcatggaaa caaaactact     840

attttatttt ttattttaaa aactggtcct ggaagaaatt tctggccacc aagggctgac     900

tgagtccata tctggtgccc gagtcttaaa taaatatctc atttaattct tcttaagaag     960

ttcttatcag taagcacggg agtccaggca aagaggttca caagttccat cctcaagctc    1020

ttttcacagg gatgggaaga aggtgttgtg tctatgctct aaacgttccc gaggccacac    1080

attcctgtct ctactttacc cccgtggtaa ctgtttagat ggcgggctcc gttctagaca    1140

tggtcgtaca agcgacagtc agacagacag gtcaccatcc tcattagcta ctgtgttagc    1200

gttgagtaga tttttctgag catcattttc cactcagaga agtagagccg tgcaagcctg    1260

taaggaaggg ttttgcaaga tgtcgaaggt gtgtgtgtgt gtgtgtgtgt gtgtgtgtgt    1320

gtgtgtgtat gcgcgtgcgt gcgcgcttcg gggacacaga gcctgctgag tttatgccag    1380

gtctctgttc acttgcacag taagttgacc tgttgtcccc actgctgctc cagccttggc    1440

acacagggga cacaaaagga aaatcctggc ttaacgaata aaatgctagc caaagggact    1500

tcctactctt atgagttttt agaagtattt caagcgaggg agctcagaga gcggaagacc    1560

cgcctctaat catccagatt ctggcaagca gggacaggga aaaaacaggg tcgaggccct    1620

gtactttggg gtatacactc actggttgag gcttctgtga tctgaacctg caggggcgca    1680
```

-continued

```
gacggggagc aggaaaccac aggcaccagc agagggcgtc gggtacctgc tgagcgtgcg   1740

gcgccgtgtt tggggtgctt gtggggcgcg ggtcacgggc ttcactcgtg agttgaccgc   1800

agaagcgccc tggcgggcgg agtgcagagc gcagagcaag cggcctggga gctggcgcag   1860

ggttggcaga atccaggagc gtggcctccc agatcggtga ccactctcca gccggggctc   1920

cccgtacccc tgttgcgggg cactcagaga gagcgcagcg atgcgggcag tgtcttgggt   1980

tagcagggcg tgggcgtggg gagggtcggc tctgattccg agctttgggt ggaacttgag   2040

gttggcctga agagacgctg agttttggtt tacttgattt gagcatcagg atttgtccct   2100

cgggttctgt cttgtgctgg ggtcccctgg ggggctgagg tagccagaga gggcacggag   2160

atttggtagg cgtcccacac ccctgctcca gctgtgcctt cagtgaacca tcgtgtcgtg   2220

tcgcccgcca ctctgcctgt caagctcagc ccaccaccag ggccgggagg ggacgcggag   2280

gcggggtggg ctgtgccctg ctggaaccca gccggccggt gccctcgccc aagctgctgt   2340

gcttgcctgg agcgcctgcc actgctaaca gggagagggt ggcgccacgg ggaggctcag   2400

ggtcctgccc taagaacgag gaaccaaagt gggacccagc gctgggctcc ctcaaacagg   2460

acagaaagct gccccagtga ctagtcctgg aggttcctct ccccaggaag ctctgagaac   2520

cctccccggg agaggggaca gcaatctgta ggtgggcaag gtagcaggaa gggtaccgct   2580

tccctggatg cctggtctgg gattccttcc ccaaatccat cccagagatt tttctgcatc   2640

aggaggggaa cagttgctat gctgactggg ctgactatgg gagctccagg ggttctggga   2700

gaagtgaccc taaagcaagg taggtggtct tgatggactt gtccaggaga tgatgcgctg   2760

gggttgtgtg tatctaaata tgcggtgtgc acagagtctt ggtgaacgac gttgtctttc   2820

cctttgcttt ttagggcatt tggagagatg cgtgccaggg gcttggagga gaaatgcatg   2880

tattttaggc cgtgtctcag aaaaagaggc agcatccctg aaaagtgact agaattgacc   2940

tggaagaggc catggactca gagtgtgctt aaaagccaat gctctccttg gggaatgtag   3000

ggaccagccg atgtcacagg gacacactgt cacagggaca gtgacctgga gcaccaagcc   3060

cagaagacag atgggaagca ggagagtctt taccccggca tggcttggat tgctacgggg   3120

aagctcctga tggaacccta ccatccttta gtccaggcag caactggggc tgaacaagaa   3180

ggggctgggt ggtgagtggt tgggggaagt ctggctaagc ctggtcaaga acttgagggg   3240

caagtccccg gaagtgtgtt ccttctggaa g atg gct cct aac act tct acc      3292
                                   Met Ala Pro Asn Thr Ser Thr
                                   1               5

atg gat gag gcc ggg ctg cca gcg gag agg gat ttc tcc ttt cgc atc     3340
Met Asp Glu Ala Gly Leu Pro Ala Glu Arg Asp Phe Ser Phe Arg Ile
        10                  15                  20

ctc acg gcc tgt ttc ctg tca ctg ctc atc ctg tcc act ctc ctg ggc     3388
Leu Thr Ala Cys Phe Leu Ser Leu Leu Ile Leu Ser Thr Leu Leu Gly
    25                  30                  35

aat acc ctt gtc tgt gcg gcc gtc atc cgg ttt cga cac ctg agg tcc     3436
Asn Thr Leu Val Cys Ala Ala Val Ile Arg Phe Arg His Leu Arg Ser
40                  45                  50                  55

aag gtg acc aac ttc ttt gtc atc tct tta gct gtg tca gat ctc ttg     3484
Lys Val Thr Asn Phe Phe Val Ile Ser Leu Ala Val Ser Asp Leu Leu
                60                  65                  70

gtg gct gtc ctg gtc atg ccc tgg aaa gct gtg gcc gag att gct ggc     3532
Val Ala Val Leu Val Met Pro Trp Lys Ala Val Ala Glu Ile Ala Gly
            75                  80                  85

ttt tgg ccc ttt ggg tcc ttt tgt aac atc tgg gta gcc ttt gac atc     3580
Phe Trp Pro Phe Gly Ser Phe Cys Asn Ile Trp Val Ala Phe Asp Ile
        90                  95                  100
```

-continued atg tgc tct acg gcg tcc att ctg aac ctc tgc gtg atc agc gtg gac 3628
Met Cys Ser Thr Ala Ser Ile Leu Asn Leu Cys Val Ile Ser Val Asp
105 110 115 agg tac tgg gct atc tcc agc cct ttc cag tat gag agg aag atg acc 3676
Arg Tyr Trp Ala Ile Ser Ser Pro Phe Gln Tyr Glu Arg Lys Met Thr
120 125 130 135 ccc aaa gca gcc ttc atc ctg att agc gta gca tgg act ctg tct gtc 3724
Pro Lys Ala Ala Phe Ile Leu Ile Ser Val Ala Trp Thr Leu Ser Val
140 145 150 ctt ata tcc ttc atc cca gta cag cta agc tgg cac aag gca aag ccc 3772
Leu Ile Ser Phe Ile Pro Val Gln Leu Ser Trp His Lys Ala Lys Pro
155 160 165 aca tgg ccc ttg gat ggc aat ttt acc tcc ctg gag gac acc gag gat 3820
Thr Trp Pro Leu Asp Gly Asn Phe Thr Ser Leu Glu Asp Thr Glu Asp
170 175 180 gac aac tgt gac aca agg ttg agc agg acg tat gcc att tca tcg tcc 3868
Asp Asn Cys Asp Thr Arg Leu Ser Arg Thr Tyr Ala Ile Ser Ser Ser
185 190 195 ctc atc agc ttt tac atc ccc gta gcc att atg atc gtc acc tac acc 3916
Leu Ile Ser Phe Tyr Ile Pro Val Ala Ile Met Ile Val Thr Tyr Thr
200 205 210 215 agt atc tac agg att gcc cag aag caa atc cgg cgc atc tca gcc ttg 3964
Ser Ile Tyr Arg Ile Ala Gln Lys Gln Ile Arg Arg Ile Ser Ala Leu
220 225 230 gag agg gca gca gtc cat gcc aag aat tgc cag acc acc gca ggt aac 4012
Glu Arg Ala Ala Val His Ala Lys Asn Cys Gln Thr Thr Ala Gly Asn
235 240 245 ggg aac ccc gtc gaa tgc gcc cag tct gaa agt tcc ttt aag atg tcc 4060
Gly Asn Pro Val Glu Cys Ala Gln Ser Glu Ser Ser Phe Lys Met Ser
250 255 260 ttc aag agg gag acg aaa gtt cta aag acg ctg tct gtg atc atg ggg 4108
Phe Lys Arg Glu Thr Lys Val Leu Lys Thr Leu Ser Val Ile Met Gly
265 270 275 gtg ttt gtg tgc tgc tgg ctc cct ttc ttc atc tcg aac tgt atg gtg 4156
Val Phe Val Cys Cys Trp Leu Pro Phe Phe Ile Ser Asn Cys Met Val
280 285 290 295 ccc ttc tgt ggc tct gag gag acc cag cca ttc tgc atc gat tcc atc 4204
Pro Phe Cys Gly Ser Glu Glu Thr Gln Pro Phe Cys Ile Asp Ser Ile
300 305 310 acc ttc gat gtg ttt gtg tgg ttt ggg tgg gcg aat tct tcc ctg aac 4252
Thr Phe Asp Val Phe Val Trp Phe Gly Trp Ala Asn Ser Ser Leu Asn
315 320 325 ccc att att tat gct ttt aat gct gac ttc cag aag gcg ttc tca acc 4300
Pro Ile Ile Tyr Ala Phe Asn Ala Asp Phe Gln Lys Ala Phe Ser Thr
330 335 340 ctc tta gga tgc tac aga ctc tgc cct act acg aat aat gcc ata gag 4348
Leu Leu Gly Cys Tyr Arg Leu Cys Pro Thr Thr Asn Asn Ala Ile Glu
345 350 355 acg gtg agc att aac aac aat ggg gct gtg gtg ttt tcc agc cac cat 4396
Thr Val Ser Ile Asn Asn Asn Gly Ala Val Val Phe Ser Ser His His
360 365 370 375 gag ccc cga ggc tcc atc tcc aag gac tgt aat ctg gtt tac ctg atc 4444
Glu Pro Arg Gly Ser Ile Ser Lys Asp Cys Asn Leu Val Tyr Leu Ile
380 385 390 cct cat gcc gtg ggc tcc tct gag gac ctg aag aag gaa gag gct ggt 4492
Pro His Ala Val Gly Ser Ser Glu Asp Leu Lys Lys Glu Glu Ala Gly
395 400 405 gga ata gct aag cca ctg gag aag ctg tcc cca gcc tta tcg gtc ata 4540
Gly Ile Ala Lys Pro Leu Glu Lys Leu Ser Pro Ala Leu Ser Val Ile -continued

```
        410                 415                 420

ttg gac tat gac acc gat gtc tct cta gaa aag atc caa cct gtc aca     4588
Leu Asp Tyr Asp Thr Asp Val Ser Leu Glu Lys Ile Gln Pro Val Thr
    425                 430                 435

cac agt gga cag cat tcc act tga atattgggtc ctcatctctg aggccacgag    4642
His Ser Gly Gln His Ser Thr
440                 445

ttcccttggg cttgctgtta aggaattaac aggagatccc tctgctgctt ttggacaatt   4702

acgaagcttc tcaaactcac tgattccagt gtattctcta gcttcaaggg aaatgacttc   4762

ggctctgaaa tcagtttggg agtattatct taggacatta taaaacaaca acaaacaaac   4822

aaacaaacaa acaaataggc caagagtcaa ctgtaaacag cttcacttaa aaatcgaact   4882

ttccagaaag gaagggtagg agttgagttt gctgtccaaa caggtgctaa aactgtccga   4942

gcagttttca gattggaaag gtaggtgcat gcctttgtta attaacttct ccaataataa   5002

ttgagcctta cagcaggagt gggattcctt tttctcagaa ttgacagatg cattgttgat   5062

gacggtttta tttatttatt tattgtacta tatgaatatt ttaaatttat catagtgaat   5122

ctatatttaa catatttaac agagcaaacc aatgtgttat ctgagactga cctctccatt   5182

tgtactagca ctttatgagc caatgaaaca tacgcgtaga ctctgagatt ctgaattgtg   5242

agttacttct gggaacacag caaagactga tgtggtggct ccttaactcg acaaggacac   5302

aaagaaacgc aagaggagaa gtgactaatg ccaccaatgc tccccctaaa aagattttga   5362

aaagattagt tttttttttt ttttaaaaga agctactatt gtgttctgag tgttttaaat   5422

ggcagaggct ttccccgggg cgaatttgca cttctgtaaa tatctatgta agaaccagct   5482

caagaggaat acaactttat atttccgctt ttggatggcg aggaagagca tatgccactt   5542

tgtatttatg taaactaatt ggccctcctt gtcatttctc atttcatgct tgaaatagct   5602

ttctgaaaca aacaaatgac tgtccaggct ggagatctgc agggtggaga atgagttgta   5662

aattcacagg tcacagcagc ccctccgata gctgggctca tcattggtcc tttatctgcc   5722

caggtctaac caagtcggct gcttaagggg ctacttttgt agtgctttaa tccgaattta   5782

gtatcctctc ttttaaaaaa aaaagctctt taatgttagt ggtaaactag ctaatgaacg   5842

gtacctcatc gctgcataat acacttctgt tggtgggggc gtagacgagc ccttcccggt   5902

gcgagcacca caaagccatc tgcatagcta gtcacaaatg ctgtttttct ttctctgtgg   5962

gtttgaatct agtttccttg ttatcatagc ctggactgca aaaagatcca tccagtcccc   6022

tcttgtgggg gcattgcaac agtgtttctt tttgtttttg ttttgttttt gaaatgttta   6082

caaggtgttc tttggaagca gttgcaacac gtggatggaa ctgaagaaaa ggctgactgg   6142

cttgctaacg gtatctcctg caggggtttt gtactgcgga ctttgaatgt tttctcagct   6202

ctaaggcttg tatgctttct tacatacaat aaacttattt tgtgaattc               6251


<210> SEQ ID NO 20
<211> LENGTH: 446
<212> TYPE: PRT
<213> ORGANISM: Rattus norvegicus

<400> SEQUENCE: 20

Met Ala Pro Asn Thr Ser Thr Met Asp Glu Ala Gly Leu Pro Ala Glu
1               5                   10                  15

Arg Asp Phe Ser Phe Arg Ile Leu Thr Ala Cys Phe Leu Ser Leu Leu
            20                  25                  30

Ile Leu Ser Thr Leu Leu Gly Asn Thr Leu Val Cys Ala Ala Val Ile
```

-continued

```
        35                  40                  45

Arg Phe Arg His Leu Arg Ser Lys Val Thr Asn Phe Phe Val Ile Ser
    50                  55                  60

Leu Ala Val Ser Asp Leu Leu Val Ala Val Leu Val Met Pro Trp Lys
65                  70                  75                  80

Ala Val Ala Glu Ile Ala Gly Phe Trp Pro Phe Gly Ser Phe Cys Asn
                85                  90                  95

Ile Trp Val Ala Phe Asp Ile Met Cys Ser Thr Ala Ser Ile Leu Asn
            100                 105                 110

Leu Cys Val Ile Ser Val Asp Arg Tyr Trp Ala Ile Ser Ser Pro Phe
        115                 120                 125

Gln Tyr Glu Arg Lys Met Thr Pro Lys Ala Ala Phe Ile Leu Ile Ser
    130                 135                 140

Val Ala Trp Thr Leu Ser Val Leu Ile Ser Phe Ile Pro Val Gln Leu
145                 150                 155                 160

Ser Trp His Lys Ala Lys Pro Thr Trp Pro Leu Asp Gly Asn Phe Thr
                165                 170                 175

Ser Leu Glu Asp Thr Glu Asp Asp Asn Cys Asp Thr Arg Leu Ser Arg
            180                 185                 190

Thr Tyr Ala Ile Ser Ser Ser Leu Ile Ser Phe Tyr Ile Pro Val Ala
        195                 200                 205

Ile Met Ile Val Thr Tyr Thr Ser Ile Tyr Arg Ile Ala Gln Lys Gln
    210                 215                 220

Ile Arg Arg Ile Ser Ala Leu Glu Arg Ala Ala Val His Ala Lys Asn
225                 230                 235                 240

Cys Gln Thr Thr Ala Gly Asn Gly Asn Pro Val Glu Cys Ala Gln Ser
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285

Phe Ile Ser Asn Cys Met Val Pro Phe Cys Gly Ser Glu Glu Thr Gln
    290                 295                 300

Pro Phe Cys Ile Asp Ser Ile Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Gln Lys Ala Phe Ser Thr Leu Leu Gly Cys Tyr Arg Leu Cys Pro
            340                 345                 350

Thr Thr Asn Asn Ala Ile Glu Thr Val Ser Ile Asn Asn Asn Gly Ala
        355                 360                 365

Val Val Phe Ser Ser His His Glu Pro Arg Gly Ser Ile Ser Lys Asp
    370                 375                 380

Cys Asn Leu Val Tyr Leu Ile Pro His Ala Val Gly Ser Ser Glu Asp
385                 390                 395                 400

Leu Lys Lys Glu Glu Ala Gly Gly Ile Ala Lys Pro Leu Glu Lys Leu
                405                 410                 415

Ser Pro Ala Leu Ser Val Ile Leu Asp Tyr Asp Thr Asp Val Ser Leu
            420                 425                 430

Glu Lys Ile Gln Pro Val Thr His Ser Gly Gln His Ser Thr
        435                 440                 445
```

<210> SEQ ID NO 21

-continued

```
<211> LENGTH: 2236
<212> TYPE: DNA
<213> ORGANISM: Rattus norvegicus
<220> FEATURE:
<221> NAME/KEY: CDS
<222> LOCATION: (60)..(1400)
<223> OTHER INFORMATION:

<400> SEQUENCE: 21

ggctaagcct ggtcaagaac ttgaggggca agtccccgga agtgtgttcc ttctggaag      59

atg gct cct aac act tct acc atg gat gag gcc ggg ctg cca gcg gag      107
Met Ala Pro Asn Thr Ser Thr Met Asp Glu Ala Gly Leu Pro Ala Glu
1               5                   10                  15

agg gat ttc tcc ttt cgc atc ctc acg gcc tgt ttc ctg tca ctg ctc      155
Arg Asp Phe Ser Phe Arg Ile Leu Thr Ala Cys Phe Leu Ser Leu Leu
            20                  25                  30

atc ctg tcc act ctc ctg ggc aat acc ctt gtc tgt gcg gcc gtc atc      203
Ile Leu Ser Thr Leu Leu Gly Asn Thr Leu Val Cys Ala Ala Val Ile
        35                  40                  45

cgg ttt cga cac ctg agg tcc aag gtg acc aac ttc ttt gtc atc tct      251
Arg Phe Arg His Leu Arg Ser Lys Val Thr Asn Phe Phe Val Ile Ser
    50                  55                  60

tta gct gtg tca gat ctc ttg gtg gct gtc ctg gtc atg ccc tgg aaa      299
Leu Ala Val Ser Asp Leu Leu Val Ala Val Leu Val Met Pro Trp Lys
65                  70                  75                  80

gct gtg gcc gag att gct ggc ttt tgg cct ttg ggt ccc ttt tgt aac      347
Ala Val Ala Glu Ile Ala Gly Phe Trp Pro Leu Gly Pro Phe Cys Asn
                85                  90                  95

atc tgg gta gcc ttt gac atc atg tgc tct acg gcg tcc att ctg aac      395
Ile Trp Val Ala Phe Asp Ile Met Cys Ser Thr Ala Ser Ile Leu Asn
            100                 105                 110

ctc tgc gtg atc agc gtg gac agg tac tgg gct atc tcc agc cct ttc      443
Leu Cys Val Ile Ser Val Asp Arg Tyr Trp Ala Ile Ser Ser Pro Phe
        115                 120                 125

cag tat gag agg aag atg acc ccc aaa gca gcc ttc atc ctg att agc      491
Gln Tyr Glu Arg Lys Met Thr Pro Lys Ala Ala Phe Ile Leu Ile Ser
    130                 135                 140

gta gca tgg act ctg tct gtc ctt ata tcc ttc atc cca gta cag cta      539
Val Ala Trp Thr Leu Ser Val Leu Ile Ser Phe Ile Pro Val Gln Leu
145                 150                 155                 160

agc tgg cac aag gca aag ccc aca tgg ccc ttg gat ggc aat ttt acc      587
Ser Trp His Lys Ala Lys Pro Thr Trp Pro Leu Asp Gly Asn Phe Thr
                165                 170                 175

tcc ctg gag gac acc gag gat gac aac tgt gac aca agg ttg agc agg      635
Ser Leu Glu Asp Thr Glu Asp Asp Asn Cys Asp Thr Arg Leu Ser Arg
            180                 185                 190

acg tat gcc att tca tcg tcc ctc atc agc ttt tac atc ccc gta gcc      683
Thr Tyr Ala Ile Ser Ser Ser Leu Ile Ser Phe Tyr Ile Pro Val Ala
        195                 200                 205

att atg atc gtc acc tac acc agt atc tac agg att gcc cag aag caa      731
Ile Met Ile Val Thr Tyr Thr Ser Ile Tyr Arg Ile Ala Gln Lys Gln
    210                 215                 220

atc cgg cgc atc tca gcc ttg gag agg gca gca gtc cat gcc aag aat      779
Ile Arg Arg Ile Ser Ala Leu Glu Arg Ala Ala Val His Ala Lys Asn
225                 230                 235                 240

tgc cag acc acc gca ggt aac ggg aac ccc gtc gaa tgc gcc cag tct      827
Cys Gln Thr Thr Ala Gly Asn Gly Asn Pro Val Glu Cys Ala Gln Ser
                245                 250                 255

gaa agt tcc ttt aag atg tcc ttc aag agg gag acg aaa gtt cta aag      875
Glu Ser Ser Phe Lys Met Ser Phe Lys Arg Glu Thr Lys Val Leu Lys
            260                 265                 270
```

-continued

```
acg ctg tct gtg atc atg ggg gtg ttt gtg tgc tgc tgg ctc cct ttc      923
Thr Leu Ser Val Ile Met Gly Val Phe Val Cys Cys Trp Leu Pro Phe
        275                 280                 285

ttc atc tcg aac tgt atg gtg ccc ttc tgt ggc tct gag gag acc cag      971
Phe Ile Ser Asn Cys Met Val Pro Phe Cys Gly Ser Glu Glu Thr Gln
    290                 295                 300

cca ttc tgc atc gat tcc atc acc ttc gat gtg ttt gtg tgg ttt ggg     1019
Pro Phe Cys Ile Asp Ser Ile Thr Phe Asp Val Phe Val Trp Phe Gly
305                 310                 315                 320

tgg gcg aat tct tcc ctg aac ccc att att tat gct ttt aat gct gac     1067
Trp Ala Asn Ser Ser Leu Asn Pro Ile Ile Tyr Ala Phe Asn Ala Asp
                325                 330                 335

ttc cag aag gcg ttc tca acc ctc tta gga tgc tac aga ctc tgc cct     1115
Phe Gln Lys Ala Phe Ser Thr Leu Leu Gly Cys Tyr Arg Leu Cys Pro
            340                 345                 350

act acg aat aat gcc ata gag acg gtg agc att aac aac aat ggg gct     1163
Thr Thr Asn Asn Ala Ile Glu Thr Val Ser Ile Asn Asn Asn Gly Ala
        355                 360                 365

gtg gtg ttt tcc agc cac cat gag ccc cga ggc tcc atc tcc aag gac     1211
Val Val Phe Ser Ser His His Glu Pro Arg Gly Ser Ile Ser Lys Asp
    370                 375                 380

tgt aat ctg gtt tac ctg atc cct cat gcc gtg ggc tcc tct gag gac     1259
Cys Asn Leu Val Tyr Leu Ile Pro His Ala Val Gly Ser Ser Glu Asp
385                 390                 395                 400

ctg aag aag gaa gag gct ggt gga ata gct aag cca ctg gag aag ctg     1307
Leu Lys Lys Glu Glu Ala Gly Gly Ile Ala Lys Pro Leu Glu Lys Leu
                405                 410                 415

tcc cca gcc tta tcg gtc ata ttg gac tat gac acc gat gtc tct cta     1355
Ser Pro Ala Leu Ser Val Ile Leu Asp Tyr Asp Thr Asp Val Ser Leu
            420                 425                 430

gaa aag atc caa cct gtc aca cac agt gga cag cat tcc act tga         1400
Glu Lys Ile Gln Pro Val Thr His Ser Gly Gln His Ser Thr
        435                 440                 445

atattgggtc ctcatctctg aggccacgag ttcccttggg cttgctgtta aggaattaac   1460

aggagatccc tctgctgctt ttggacaatt acgaagcttc tcaaactcac tgattccagt   1520

gtattctcta gcttcaaggg aaatgacttc ggctctgaaa tcagtttggg agtattatct   1580

taggacatta taaaacaaca acaaacaaac aaacaaacaa acaaataggc caagagtcaa   1640

ctgtaaacag cttcacttaa aaatcgaact ttccagaaag gaagggtagg agttgagttt   1700

gctgtccaaa caggtgctaa aactgtccga gcagttttca gattggaaag gtaggtgcat   1760

gcctttgtta attaacttct ccaataataa ttgagcctta cagcaggagt gggattcctt   1820

tttctcagaa ttgacagatg cattgttgat gacggtttta tttatttatt tattgtacta   1880

tatgaatatt ttaaatttat catagtgaat ctatatttaa catatttaac agagcaaacc   1940

aatgtgttat ctgagactga cctctccatt tgtactagca ctttatgagc caatgaaaca   2000

tacgcgtaga ctctgagatt ctgaattgtg agttacttct gggaacacag caaagactga   2060

tgtggtggct ccttaactcg acaaggacac aaagaaacgc aagaggagaa gtgactaatg   2120

ccaccaatgc tccccctaaa aagattttga aaagattagt tttttttttt ttttaaaaga   2180

agctactatt gtgttctgaa tgttttaaat ggcagaggct ttccccgggg cgaatt       2236
```

<210> SEQ ID NO 22
<211> LENGTH: 446
<212> TYPE: PRT
<213> ORGANISM: Rattus norvegicus -continued

<400> SEQUENCE: 22

```
Met Ala Pro Asn Thr Ser Thr Met Asp Glu Ala Gly Leu Pro Ala Glu
1               5                   10                  15

Arg Asp Phe Ser Phe Arg Ile Leu Thr Ala Cys Phe Leu Ser Leu Leu
            20                  25                  30

Ile Leu Ser Thr Leu Leu Gly Asn Thr Leu Val Cys Ala Ala Val Ile
        35                  40                  45

Arg Phe Arg His Leu Arg Ser Lys Val Thr Asn Phe Phe Val Ile Ser
    50                  55                  60

Leu Ala Val Ser Asp Leu Leu Val Ala Val Leu Val Met Pro Trp Lys
65                  70                  75                  80

Ala Val Ala Glu Ile Ala Gly Phe Trp Pro Leu Gly Pro Phe Cys Asn
                85                  90                  95

Ile Trp Val Ala Phe Asp Ile Met Cys Ser Thr Ala Ser Ile Leu Asn
            100                 105                 110

Leu Cys Val Ile Ser Val Asp Arg Tyr Trp Ala Ile Ser Ser Pro Phe
        115                 120                 125

Gln Tyr Glu Arg Lys Met Thr Pro Lys Ala Ala Phe Ile Leu Ile Ser
    130                 135                 140

Val Ala Trp Thr Leu Ser Val Leu Ile Ser Phe Ile Pro Val Gln Leu
145                 150                 155                 160

Ser Trp His Lys Ala Lys Pro Thr Trp Pro Leu Asp Gly Asn Phe Thr
                165                 170                 175

Ser Leu Glu Asp Thr Glu Asp Asp Asn Cys Asp Thr Arg Leu Ser Arg
            180                 185                 190

Thr Tyr Ala Ile Ser Ser Ser Leu Ile Ser Phe Tyr Ile Pro Val Ala
        195                 200                 205

Ile Met Ile Val Thr Tyr Thr Ser Ile Tyr Arg Ile Ala Gln Lys Gln
    210                 215                 220

Ile Arg Arg Ile Ser Ala Leu Glu Arg Ala Ala Val His Ala Lys Asn
225                 230                 235                 240

Cys Gln Thr Thr Ala Gly Asn Gly Asn Pro Val Glu Cys Ala Gln Ser
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285

Phe Ile Ser Asn Cys Met Val Pro Phe Cys Gly Ser Glu Glu Thr Gln
    290                 295                 300

Pro Phe Cys Ile Asp Ser Ile Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Gln Lys Ala Phe Ser Thr Leu Leu Gly Cys Tyr Arg Leu Cys Pro
            340                 345                 350

Thr Thr Asn Asn Ala Ile Glu Thr Val Ser Ile Asn Asn Asn Gly Ala
        355                 360                 365

Val Val Phe Ser Ser His His Glu Pro Arg Gly Ser Ile Ser Lys Asp
    370                 375                 380

Cys Asn Leu Val Tyr Leu Ile Pro His Ala Val Gly Ser Ser Glu Asp
385                 390                 395                 400

Leu Lys Lys Glu Glu Ala Gly Gly Ile Ala Lys Pro Leu Glu Lys Leu
                405                 410                 415
```

-continued

```
Ser Pro Ala Leu Ser Val Ile Leu Asp Tyr Asp Thr Asp Val Ser Leu
            420                 425                 430

Glu Lys Ile Gln Pro Val Thr His Ser Gly Gln His Ser Thr
        435                 440                 445


<210> SEQ ID NO 23
<211> LENGTH: 2308
<212> TYPE: DNA
<213> ORGANISM: Rattus norvegicus
<220> FEATURE:
<221> NAME/KEY: CDS
<222> LOCATION: (694)..(2121)
<223> OTHER INFORMATION:

<400> SEQUENCE: 23

gaattcaagg tcctatgacc cagaataggg gttcgggata cagttgtgac ttcgaaggcc      60

actctcctat cctctaagtc tctggtttgt ctagaggcct ctggatctcc tccacccaga     120

agtgttccag gagagacacc aagagaggtg tttgggagaa gctaattcat gggtttgggg     180

caagggtgtg gcactgggtt cactctcgga cctgtgtgtg gcctctaaag ttggaagaag     240

acatcagaga gtcatgaagc taggaagcag gtgggagggt gcgcgggctg cagaagcgtg     300

gctgataggg gcgggcgcgc gggacgcggc agccaccgcg ccagagagat cgcccggtgc     360

ccgcgactcc ggaccccgcc cccgttggcg gccgctctgc gtttctccga ctcggaacca     420

gacacagtgg cagcctccgg tgtgctgccg acacaggatc tcagacccgg cggcccgcgg     480

gcatcggtcg tttctggtcc catcttgggg accagaggtg cgcaagagtg ttaccattac     540

aggatcctaa gcggtgcacg gtgagcgctc ctcgggtcgg ggacggtcag ctgcagggcc     600

cggacgacct ctggggtgcc cgatggggcc ttccacgggg cgcaggggcg aagttgggac     660

cgcaagcaga gagcccgagc tactcagcgc gac atg ctg cct cct ggg cgc aac      714
                                     Met Leu Pro Pro Gly Arg Asn
                                     1               5

cgc acg gct caa ccg gca agg ctg gga tta cag agg caa ctg gct cag      762
Arg Thr Ala Gln Pro Ala Arg Leu Gly Leu Gln Arg Gln Leu Ala Gln
        10                  15                  20

gtg gac gcc cca gcg ggc tct gca acc cca ctg gga ccc gcg cag gtg      810
Val Asp Ala Pro Ala Gly Ser Ala Thr Pro Leu Gly Pro Ala Gln Val
    25                  30                  35

gtc acc gca ggc ctc ctg act ctc cta atc gtc tgg acc ttg ctc ggg      858
Val Thr Ala Gly Leu Leu Thr Leu Leu Ile Val Trp Thr Leu Leu Gly
40                  45                  50                  55

aac gtg cta gtg tgt gct gcc atc gtc cgc agc cgc cat ctg cgc gcc      906
Asn Val Leu Val Cys Ala Ala Ile Val Arg Ser Arg His Leu Arg Ala
                60                  65                  70

aag atg acc aac atc ttc atc gta tcc cta gct gtc tca gac ctc ttc      954
Lys Met Thr Asn Ile Phe Ile Val Ser Leu Ala Val Ser Asp Leu Phe
            75                  80                  85

gtg gca ttg ctg gtc atg ccc tgg aag gct gtg gct gag gtg gct ggg     1002
Val Ala Leu Leu Val Met Pro Trp Lys Ala Val Ala Glu Val Ala Gly
        90                  95                  100

tac tgg ccc ttt ggg aca ttc tgc gac atc tgg gtg gcc ttt gac atc     1050
Tyr Trp Pro Phe Gly Thr Phe Cys Asp Ile Trp Val Ala Phe Asp Ile
    105                 110                 115

atg tgc tcc act gcc tcc atc ctg aat ctg tgt atc atc agc gtg gac     1098
Met Cys Ser Thr Ala Ser Ile Leu Asn Leu Cys Ile Ile Ser Val Asp
120                 125                 130                 135

cgt tac tgg gct att tcc aga ccc ttc cgc tac gag cgc aag atg acc     1146
Arg Tyr Trp Ala Ile Ser Arg Pro Phe Arg Tyr Glu Arg Lys Met Thr
```

-continued

```
              140                 145                 150

cag cga gta gcc ctg gtc atg gtg ggc ctg gcc tgg acc ttg tcc atc     1194
Gln Arg Val Ala Leu Val Met Val Gly Leu Ala Trp Thr Leu Ser Ile
            155                 160                 165

ctc atc tcc ttc atc ccg gtc caa ctc aat tgg cac aga gac aag gca     1242
Leu Ile Ser Phe Ile Pro Val Gln Leu Asn Trp His Arg Asp Lys Ala
        170                 175                 180

ggc tcc cag ggc caa gag ggc ctg ctg tcc aat ggg aca ccc tgg gag     1290
Gly Ser Gln Gly Gln Glu Gly Leu Leu Ser Asn Gly Thr Pro Trp Glu
    185                 190                 195

gaa ggc tgg gag cta gaa ggg agg acg gag aac tgt gac tcc agc ctg     1338
Glu Gly Trp Glu Leu Glu Gly Arg Thr Glu Asn Cys Asp Ser Ser Leu
200                 205                 210                 215

aac cga acc tat gcc atc tcc tcg tca ctc atc agc ttc tac atc ccg     1386
Asn Arg Thr Tyr Ala Ile Ser Ser Ser Leu Ile Ser Phe Tyr Ile Pro
                220                 225                 230

gtg gcc atc atg atc gtg acc tat acg cgt atc tac cgc att gcg cag     1434
Val Ala Ile Met Ile Val Thr Tyr Thr Arg Ile Tyr Arg Ile Ala Gln
            235                 240                 245

gtg cag atc cgg cgg atc tcc tcc cta gag agg gca gct gag cat gct     1482
Val Gln Ile Arg Arg Ile Ser Ser Leu Glu Arg Ala Ala Glu His Ala
        250                 255                 260

cag agt tgc cgg agt cgt gga gcc tat gaa cct gac ccc agc ctg cga     1530
Gln Ser Cys Arg Ser Arg Gly Ala Tyr Glu Pro Asp Pro Ser Leu Arg
    265                 270                 275

gcg tcc atc aag aag gag acc aag gtc ttc aaa acc ctg tca atg atc     1578
Ala Ser Ile Lys Lys Glu Thr Lys Val Phe Lys Thr Leu Ser Met Ile
280                 285                 290                 295

atg ggg gtc ttc gtg tgt tgc tgg ttg cct ttc ttc atc ctg aac tgt     1626
Met Gly Val Phe Val Cys Cys Trp Leu Pro Phe Phe Ile Leu Asn Cys
                300                 305                 310

atg gtt cct ttc tgc agt agt ggg gat gcc gag ggc cca aag act ggc     1674
Met Val Pro Phe Cys Ser Ser Gly Asp Ala Glu Gly Pro Lys Thr Gly
            315                 320                 325

ttc cct tgt gtc agc gag acc acc ttc gac ata ttc gtc tgg ttt ggc     1722
Phe Pro Cys Val Ser Glu Thr Thr Phe Asp Ile Phe Val Trp Phe Gly
        330                 335                 340

tgg gcc aac tcc tct ctc aat ccc atc atc tat gcc ttt aat gca gac     1770
Trp Ala Asn Ser Ser Leu Asn Pro Ile Ile Tyr Ala Phe Asn Ala Asp
    345                 350                 355

ttc cgg aag gtg ttt gcc cag ctg ctg ggg tgc agc cac ttc tgc ttc     1818
Phe Arg Lys Val Phe Ala Gln Leu Leu Gly Cys Ser His Phe Cys Phe
360                 365                 370                 375

cgg acc cca gtg cag acg gta aac atc agt aat gag ctc atc tcc tac     1866
Arg Thr Pro Val Gln Thr Val Asn Ile Ser Asn Glu Leu Ile Ser Tyr
                380                 385                 390

aac caa gac acg gtc ttc cac aag gag atc gct act gcc tat gtc cac     1914
Asn Gln Asp Thr Val Phe His Lys Glu Ile Ala Thr Ala Tyr Val His
            395                 400                 405

atg ata ccg aat gca gta tcc tcc gga gac agg gag gtg gga gag gag     1962
Met Ile Pro Asn Ala Val Ser Ser Gly Asp Arg Glu Val Gly Glu Glu
        410                 415                 420

gag gag gag ggg cct ttc gat cac atg tct caa atc tct cca acg acg     2010
Glu Glu Glu Gly Pro Phe Asp His Met Ser Gln Ile Ser Pro Thr Thr
    425                 430                 435

cca gac ggt gac ctg gct gct gag tct gtc tgg gag ctt gac tgt gag     2058
Pro Asp Gly Asp Leu Ala Ala Glu Ser Val Trp Glu Leu Asp Cys Glu
440                 445                 450                 455

gaa gag gtt tcc tta ggc aaa atc tca cct ctc acc ccc aat tgt ttc     2106
```

-continued

```
Glu Glu Val Ser Leu Gly Lys Ile Ser Pro Leu Thr Pro Asn Cys Phe
                460                 465                 470

gat aaa act gct tag aaacattctc atgggcatat acaatggtgg ccatatttcc     2161
Asp Lys Thr Ala
            475

aagcatgcac aaatacccac gtgcgtacac acacacacac acacacacac acacacacac   2221

acactccagt gtgcatatgc tttctgtagt ctgctgcata gaaacaaacg attcttagct   2281

gagaaatgac gaggctgttg gataact                                       2308


<210> SEQ ID NO 24
<211> LENGTH: 475
<212> TYPE: PRT
<213> ORGANISM: Rattus norvegicus

<400> SEQUENCE: 24

Met Leu Pro Pro Gly Arg Asn Arg Thr Ala Gln Pro Ala Arg Leu Gly
1               5                   10                  15

Leu Gln Arg Gln Leu Ala Gln Val Asp Ala Pro Ala Gly Ser Ala Thr
            20                  25                  30

Pro Leu Gly Pro Ala Gln Val Val Thr Ala Gly Leu Leu Thr Leu Leu
        35                  40                  45

Ile Val Trp Thr Leu Leu Gly Asn Val Leu Val Cys Ala Ala Ile Val
    50                  55                  60

Arg Ser Arg His Leu Arg Ala Lys Met Thr Asn Ile Phe Ile Val Ser
65                  70                  75                  80

Leu Ala Val Ser Asp Leu Phe Val Ala Leu Leu Val Met Pro Trp Lys
                85                  90                  95

Ala Val Ala Glu Val Ala Gly Tyr Trp Pro Phe Gly Thr Phe Cys Asp
            100                 105                 110

Ile Trp Val Ala Phe Asp Ile Met Cys Ser Thr Ala Ser Ile Leu Asn
        115                 120                 125

Leu Cys Ile Ile Ser Val Asp Arg Tyr Trp Ala Ile Ser Arg Pro Phe
    130                 135                 140

Arg Tyr Glu Arg Lys Met Thr Gln Arg Val Ala Leu Val Met Val Gly
145                 150                 155                 160

Leu Ala Trp Thr Leu Ser Ile Leu Ile Ser Phe Ile Pro Val Gln Leu
                165                 170                 175

Asn Trp His Arg Asp Lys Ala Gly Ser Gln Gly Gln Glu Gly Leu Leu
            180                 185                 190

Ser Asn Gly Thr Pro Trp Glu Glu Gly Trp Glu Leu Glu Gly Arg Thr
        195                 200                 205

Glu Asn Cys Asp Ser Ser Leu Asn Arg Thr Tyr Ala Ile Ser Ser Ser
    210                 215                 220

Leu Ile Ser Phe Tyr Ile Pro Val Ala Ile Met Ile Val Thr Tyr Thr
225                 230                 235                 240

Arg Ile Tyr Arg Ile Ala Gln Val Gln Ile Arg Arg Ile Ser Ser Leu
                245                 250                 255

Glu Arg Ala Ala Glu His Ala Gln Ser Cys Arg Ser Arg Gly Ala Tyr
            260                 265                 270

Glu Pro Asp Pro Ser Leu Arg Ala Ser Ile Lys Lys Glu Thr Lys Val
        275                 280                 285

Phe Lys Thr Leu Ser Met Ile Met Gly Val Phe Val Cys Cys Trp Leu
    290                 295                 300

Pro Phe Phe Ile Leu Asn Cys Met Val Pro Phe Cys Ser Ser Gly Asp
```

-continued

```
305                 310                 315                 320

Ala Glu Gly Pro Lys Thr Gly Phe Pro Cys Val Ser Glu Thr Thr Phe
                325                 330                 335

Asp Ile Phe Val Trp Phe Gly Trp Ala Asn Ser Ser Leu Asn Pro Ile
            340                 345                 350

Ile Tyr Ala Phe Asn Ala Asp Phe Arg Lys Val Phe Ala Gln Leu Leu
        355                 360                 365

Gly Cys Ser His Phe Cys Phe Arg Thr Pro Val Gln Thr Val Asn Ile
    370                 375                 380

Ser Asn Glu Leu Ile Ser Tyr Asn Gln Asp Thr Val Phe His Lys Glu
385                 390                 395                 400

Ile Ala Thr Ala Tyr Val His Met Ile Pro Asn Ala Val Ser Ser Gly
                405                 410                 415

Asp Arg Glu Val Gly Glu Glu Glu Glu Glu Gly Pro Phe Asp His Met
            420                 425                 430

Ser Gln Ile Ser Pro Thr Thr Pro Asp Gly Asp Leu Ala Ala Glu Ser
        435                 440                 445

Val Trp Glu Leu Asp Cys Glu Glu Glu Val Ser Leu Gly Lys Ile Ser
    450                 455                 460

Pro Leu Thr Pro Asn Cys Phe Asp Lys Thr Ala
465                 470                 475


<210> SEQ ID NO 25
<211> LENGTH: 1353
<212> TYPE: DNA
<213> ORGANISM: Gallus domesticus
<220> FEATURE:
<221> NAME/KEY: CDS
<222> LOCATION: (1)..(1353)
<223> OTHER INFORMATION:

<400> SEQUENCE: 25

atg act tgg aac gac acc act atg gat ggg gaa ggg ttg ctt gtg gaa       48
Met Thr Trp Asn Asp Thr Thr Met Asp Gly Glu Gly Leu Leu Val Glu
1               5                   10                  15

agg gac tct tcc ttt cgg atc ctc acg ggc tgc ttc ctc tcg ctg ctg       96
Arg Asp Ser Ser Phe Arg Ile Leu Thr Gly Cys Phe Leu Ser Leu Leu
            20                  25                  30

atc ctc tcc acg ctg ctg gga aac acg ctg gtc tgc gca gct gtc att      144
Ile Leu Ser Thr Leu Leu Gly Asn Thr Leu Val Cys Ala Ala Val Ile
        35                  40                  45

agg ttt cgc cac ctc agg tcc aaa gtg acc aac ttc ttt gtc atc tcc      192
Arg Phe Arg His Leu Arg Ser Lys Val Thr Asn Phe Phe Val Ile Ser
    50                  55                  60

ttg gct gtg tca gac ctc ttg gtg gcg gtt ttg gtc atg cct tgg aaa      240
Leu Ala Val Ser Asp Leu Leu Val Ala Val Leu Val Met Pro Trp Lys
65                  70                  75                  80

gct gtg tct gag atc gct ggt ttc tgg cct ttt ggt tca ttt tgc aac      288
Ala Val Ser Glu Ile Ala Gly Phe Trp Pro Phe Gly Ser Phe Cys Asn
                85                  90                  95

atc tgg gtg gcc ttt gat att atg tgc tca aca gcc tcc atc tta aat      336
Ile Trp Val Ala Phe Asp Ile Met Cys Ser Thr Ala Ser Ile Leu Asn
            100                 105                 110

ctc tgt gtc att agt gtg gac aga tac tgg gcc atc tcc agc cca ttc      384
Leu Cys Val Ile Ser Val Asp Arg Tyr Trp Ala Ile Ser Ser Pro Phe
        115                 120                 125

agg tac gag agg aaa atg acc ccc aag gca gcc ttc atc atg atc agt      432
Arg Tyr Glu Arg Lys Met Thr Pro Lys Ala Ala Phe Ile Met Ile Ser
    130                 135                 140
```

-continued

```
gtg gcg tgg act ttg tct gtg ttg att tcc ttc atc ccc gtg cag ctg      480
Val Ala Trp Thr Leu Ser Val Leu Ile Ser Phe Ile Pro Val Gln Leu
145                 150                 155                 160

aac tgg cac aag gct aca acc acg agc ttt ttg gac ctg aat gcc agt      528
Asn Trp His Lys Ala Thr Thr Thr Ser Phe Leu Asp Leu Asn Ala Ser
                165                 170                 175

tta caa ggt ata agc atg gac aac tgt gat tct agc cta aac agg atg      576
Leu Gln Gly Ile Ser Met Asp Asn Cys Asp Ser Ser Leu Asn Arg Met
            180                 185                 190

tat gcc atc tcc tct tct cta att agc ttc tat ata cct gtg gcc atc      624
Tyr Ala Ile Ser Ser Ser Leu Ile Ser Phe Tyr Ile Pro Val Ala Ile
        195                 200                 205

atg ata gta acc tac aca agg ata tac cgg att gct cag aag caa ata      672
Met Ile Val Thr Tyr Thr Arg Ile Tyr Arg Ile Ala Gln Lys Gln Ile
    210                 215                 220

cga cga att tca gct ttg gag aga gca gca gtg cat gcc aag aac tgc      720
Arg Arg Ile Ser Ala Leu Glu Arg Ala Ala Val His Ala Lys Asn Cys
225                 230                 235                 240

cag aac aca agt ggc aac aga agc agc atg gac tgc cag caa ccc gag      768
Gln Asn Thr Ser Gly Asn Arg Ser Ser Met Asp Cys Gln Gln Pro Glu
                245                 250                 255

agc aac ttc aaa atg tcc ttc aag agg gaa aca aag gtt cta aag act      816
Ser Asn Phe Lys Met Ser Phe Lys Arg Glu Thr Lys Val Leu Lys Thr
            260                 265                 270

ttg tca gtg atc atg ggg gtg ttt gtg tgc tgc tgg ttg cca ttt ttc      864
Leu Ser Val Ile Met Gly Val Phe Val Cys Cys Trp Leu Pro Phe Phe
        275                 280                 285

gtg ttg aac tgc atg att ccc ttc tgc gag ccc acc caa ccg tcc aag      912
Val Leu Asn Cys Met Ile Pro Phe Cys Glu Pro Thr Gln Pro Ser Lys
    290                 295                 300

gga gca gaa gct ttc tgc att aac tcc acc acc ttt gac gtt ttt att      960
Gly Ala Glu Ala Phe Cys Ile Asn Ser Thr Thr Phe Asp Val Phe Ile
305                 310                 315                 320

tgg ttt gga tgg gct aat tct tcc ctg aac ccc atc att tat gcc ttc     1008
Trp Phe Gly Trp Ala Asn Ser Ser Leu Asn Pro Ile Ile Tyr Ala Phe
                325                 330                 335

aac gct gat ttc cgc aag gca ttt tcc acc ctg cta gga tgc tac agg     1056
Asn Ala Asp Phe Arg Lys Ala Phe Ser Thr Leu Leu Gly Cys Tyr Arg
            340                 345                 350

ctc tgc ccg atg tcc ggc aat gct ata gag act gtt agc att aac aac     1104
Leu Cys Pro Met Ser Gly Asn Ala Ile Glu Thr Val Ser Ile Asn Asn
        355                 360                 365

aac gga gca gtt ttt tca agc caa cat gag ccc aaa ggg tcc agc ccc     1152
Asn Gly Ala Val Phe Ser Ser Gln His Glu Pro Lys Gly Ser Ser Pro
    370                 375                 380

aaa gag tcg aat ctg gtt tat ctg atc cca cat gca atc atc tgt ccg     1200
Lys Glu Ser Asn Leu Val Tyr Leu Ile Pro His Ala Ile Ile Cys Pro
385                 390                 395                 400

gaa gaa gaa cct cta aaa aag gaa gaa gag ggt gaa cta tct aag acc     1248
Glu Glu Glu Pro Leu Lys Lys Glu Glu Glu Gly Glu Leu Ser Lys Thr
                405                 410                 415

ttg gag aaa atg tct cca gca ttg tcg ggt atg ttg gat tat gaa gct     1296
Leu Glu Lys Met Ser Pro Ala Leu Ser Gly Met Leu Asp Tyr Glu Ala
            420                 425                 430

gac gtt tct ttg gaa aag atc acc ccc att aca caa aat ggg cag cat     1344
Asp Val Ser Leu Glu Lys Ile Thr Pro Ile Thr Gln Asn Gly Gln His
        435                 440                 445

aaa acc tga                                                         1353
Lys Thr
```

-continued

450

<210> SEQ ID NO 26
<211> LENGTH: 450
<212> TYPE: PRT
<213> ORGANISM: Gallus domesticus

<400> SEQUENCE: 26

```
Met Thr Trp Asn Asp Thr Thr Met Asp Gly Glu Gly Leu Leu Val Glu
1               5                   10                  15

Arg Asp Ser Ser Phe Arg Ile Leu Thr Gly Cys Phe Leu Ser Leu Leu
            20                  25                  30

Ile Leu Ser Thr Leu Leu Gly Asn Thr Leu Val Cys Ala Ala Val Ile
        35                  40                  45

Arg Phe Arg His Leu Arg Ser Lys Val Thr Asn Phe Phe Val Ile Ser
    50                  55                  60

Leu Ala Val Ser Asp Leu Leu Val Ala Val Leu Val Met Pro Trp Lys
65                  70                  75                  80

Ala Val Ser Glu Ile Ala Gly Phe Trp Pro Phe Gly Ser Phe Cys Asn
                85                  90                  95

Ile Trp Val Ala Phe Asp Ile Met Cys Ser Thr Ala Ser Ile Leu Asn
            100                 105                 110

Leu Cys Val Ile Ser Val Asp Arg Tyr Trp Ala Ile Ser Ser Pro Phe
        115                 120                 125

Arg Tyr Glu Arg Lys Met Thr Pro Lys Ala Ala Phe Ile Met Ile Ser
    130                 135                 140

Val Ala Trp Thr Leu Ser Val Leu Ile Ser Phe Ile Pro Val Gln Leu
145                 150                 155                 160

Asn Trp His Lys Ala Thr Thr Thr Ser Phe Leu Asp Leu Asn Ala Ser
                165                 170                 175

Leu Gln Gly Ile Ser Met Asp Asn Cys Asp Ser Ser Leu Asn Arg Met
            180                 185                 190

Tyr Ala Ile Ser Ser Ser Leu Ile Ser Phe Tyr Ile Pro Val Ala Ile
        195                 200                 205

Met Ile Val Thr Tyr Thr Arg Ile Tyr Arg Ile Ala Gln Lys Gln Ile
    210                 215                 220

Arg Arg Ile Ser Ala Leu Glu Arg Ala Ala Val His Ala Lys Asn Cys
225                 230                 235                 240

Gln Asn Thr Ser Gly Asn Arg Ser Ser Met Asp Cys Gln Gln Pro Glu
                245                 250                 255

Ser Asn Phe Lys Met Ser Phe Lys Arg Glu Thr Lys Val Leu Lys Thr
            260                 265                 270

Leu Ser Val Ile Met Gly Val Phe Val Cys Cys Trp Leu Pro Phe Phe
        275                 280                 285

Val Leu Asn Cys Met Ile Pro Phe Cys Glu Pro Thr Gln Pro Ser Lys
    290                 295                 300

Gly Ala Glu Ala Phe Cys Ile Asn Ser Thr Thr Phe Asp Val Phe Ile
305                 310                 315                 320

Trp Phe Gly Trp Ala Asn Ser Ser Leu Asn Pro Ile Ile Tyr Ala Phe
                325                 330                 335

Asn Ala Asp Phe Arg Lys Ala Phe Ser Thr Leu Leu Gly Cys Tyr Arg
            340                 345                 350

Leu Cys Pro Met Ser Gly Asn Ala Ile Glu Thr Val Ser Ile Asn Asn
        355                 360                 365
```

-continued

```
Asn Gly Ala Val Phe Ser Ser Gln His Glu Pro Lys Gly Ser Ser Pro
    370                 375                 380

Lys Glu Ser Asn Leu Val Tyr Leu Ile Pro His Ala Ile Ile Cys Pro
385                 390                 395                 400

Glu Glu Glu Pro Leu Lys Lys Glu Glu Glu Gly Glu Leu Ser Lys Thr
                405                 410                 415

Leu Glu Lys Met Ser Pro Ala Leu Ser Gly Met Leu Asp Tyr Glu Ala
            420                 425                 430

Asp Val Ser Leu Glu Lys Ile Thr Pro Ile Thr Gln Asn Gly Gln His
        435                 440                 445

Lys Thr
    450


<210> SEQ ID NO 27
<211> LENGTH: 1646
<212> TYPE: DNA
<213> ORGANISM: Anguilla anguilla
<220> FEATURE:
<221> NAME/KEY: CDS
<222> LOCATION: (174)..(1511)
<223> OTHER INFORMATION:

<400> SEQUENCE: 27

ggattgatga catacaaact tctggtaagc tggtagcaat ggtaaggagg gcagcaaact     60

acagaccagg cggtccgtag cccccgcgcc gagacgccgc tttccccaaa gctgccgtcg    120

ctccgaccca gtggaattat gaggtgattc ctgccgcccg agagctgcag aag atg       176
                                                           Met
                                                           1

gat ctg aac ttg tcc acg gtc ctc gac ggc gac ctg ccg gag aag gac      224
Asp Leu Asn Leu Ser Thr Val Leu Asp Gly Asp Leu Pro Glu Lys Asp
            5                   10                  15

tcg tcc gcc cgg gtc ctg acc ggc tgc ttc ctg tcc ctg ctc atc ctg      272
Ser Ser Ala Arg Val Leu Thr Gly Cys Phe Leu Ser Leu Leu Ile Leu
        20                  25                  30

acg acg ctc ctg ggg aac acg ctg gtg tgt gcc gcc gtc acc cgc ttc      320
Thr Thr Leu Leu Gly Asn Thr Leu Val Cys Ala Ala Val Thr Arg Phe
    35                  40                  45

cgc cac ctg cgc tcc aag gtc acc aac ttc ttc gtc atc tcg ctg gcc      368
Arg His Leu Arg Ser Lys Val Thr Asn Phe Phe Val Ile Ser Leu Ala
50                  55                  60                  65

atc tcg gac ctg ctg gtg gcc atc ctg gtg atg ccg tgg aag gcc gcc      416
Ile Ser Asp Leu Leu Val Ala Ile Leu Val Met Pro Trp Lys Ala Ala
                70                  75                  80

acc gag atc gtg ggc ttc tgg ccc ttc ggc tcc ttc tgc aac gtc tgg      464
Thr Glu Ile Val Gly Phe Trp Pro Phe Gly Ser Phe Cys Asn Val Trp
            85                  90                  95

gtg gcg ttc gac atc atg tgc tcc acc gcg tcc atc ctc aac ctg tgc      512
Val Ala Phe Asp Ile Met Cys Ser Thr Ala Ser Ile Leu Asn Leu Cys
        100                 105                 110

gtg atc agc gtg gac cgc tac tgg gcc ata tcg agc ccc ttc cgg tac      560
Val Ile Ser Val Asp Arg Tyr Trp Ala Ile Ser Ser Pro Phe Arg Tyr
    115                 120                 125

gag cgg aag atg acg cca aag gtg gcg ttc gtg atg atc agc gtg gcg      608
Glu Arg Lys Met Thr Pro Lys Val Ala Phe Val Met Ile Ser Val Ala
130                 135                 140                 145

tgg acc ctg tcc gtc ctc atc tcc ttc atc ccc gtg cag ctg aac tgg      656
Trp Thr Leu Ser Val Leu Ile Ser Phe Ile Pro Val Gln Leu Asn Trp
                150                 155                 160

cac aag gcg cag gcg gcg ggc ttc ccg gag ctc aac gga acc ttc cgg      704
```

-continued

```
His Lys Ala Gln Ala Ala Gly Phe Pro Glu Leu Asn Gly Thr Phe Arg
            165                 170                 175

gag ccg ccg ccg ccg gac aac tgc gac tcc agc ctc aac cgc acc tac      752
Glu Pro Pro Pro Pro Asp Asn Cys Asp Ser Ser Leu Asn Arg Thr Tyr
        180                 185                 190

gcc atc tcc tcg tcc ctc atc agc ttc tac atc ccc gtg gcc atc atg      800
Ala Ile Ser Ser Ser Leu Ile Ser Phe Tyr Ile Pro Val Ala Ile Met
    195                 200                 205

atc gtc acg tac acg cgg atc tac agg atc gcg cag aag cag atc cgg      848
Ile Val Thr Tyr Thr Arg Ile Tyr Arg Ile Ala Gln Lys Gln Ile Arg
210                 215                 220                 225

cgg atc tct gcc ttg gag agg gcg gcg gag agc gcc aag aac cgc cac      896
Arg Ile Ser Ala Leu Glu Arg Ala Ala Glu Ser Ala Lys Asn Arg His
            230                 235                 240

agc agc atg ggc aac agc att gag tcg gag agc tcc ttc aag atg tcc      944
Ser Ser Met Gly Asn Ser Ile Glu Ser Glu Ser Ser Phe Lys Met Ser
            245                 250                 255

ttc aag cgg gag acc aag gtc ctg aag acc ctc tcg gtc ata atg ggg      992
Phe Lys Arg Glu Thr Lys Val Leu Lys Thr Leu Ser Val Ile Met Gly
        260                 265                 270

gtg ttc gtc tgc tgc tgg ctg ccc ttc ttc atc ctc aac tgc atg gtg     1040
Val Phe Val Cys Cys Trp Leu Pro Phe Phe Ile Leu Asn Cys Met Val
    275                 280                 285

ccc ttc tgc gag cag gca ccc cag ggc gca gcc gac ctc ccc tgc gtc     1088
Pro Phe Cys Glu Gln Ala Pro Gln Gly Ala Ala Asp Leu Pro Cys Val
290                 295                 300                 305

agc tcc acc acc ttc gac gtc ttc gtc tgg ttc ggc tgg gcc aac tcg     1136
Ser Ser Thr Thr Phe Asp Val Phe Val Trp Phe Gly Trp Ala Asn Ser
                310                 315                 320

tcc ctc aac ccc atc atc tac gcc ttc aac gcc gac ttc cgc aag gcc     1184
Ser Leu Asn Pro Ile Ile Tyr Ala Phe Asn Ala Asp Phe Arg Lys Ala
            325                 330                 335

ttc tcc acg ctg ctg ggc tgc cac agg gtg tgc tcg ggc ggc aac gcc     1232
Phe Ser Thr Leu Leu Gly Cys His Arg Val Cys Ser Gly Gly Asn Ala
        340                 345                 350

atc gag atc gtc agc atc aac aac aac aac ggg gcc gcc gcc cac tcc     1280
Ile Glu Ile Val Ser Ile Asn Asn Asn Asn Gly Ala Ala Ala His Ser
    355                 360                 365

tac cac tac gag acc aag ggc cac atc ccc aag gag agc aat gtg gcc     1328
Tyr His Tyr Glu Thr Lys Gly His Ile Pro Lys Glu Ser Asn Val Ala
370                 375                 380                 385

tac atg atc ccc cac tcc atc ctc tgc cag gac gag gag ctg gag aag     1376
Tyr Met Ile Pro His Ser Ile Leu Cys Gln Asp Glu Glu Leu Glu Lys
                390                 395                 400

agg gag gaa gac tcc gcg ggg atg aag gac ctg gag aag ctg tcg ccc     1424
Arg Glu Glu Asp Ser Ala Gly Met Lys Asp Leu Glu Lys Leu Ser Pro
            405                 410                 415

gcc gtg tcg ggg gac ttg gac agc gag gcc gag gtc tcc ctg gat aag     1472
Ala Val Ser Gly Asp Leu Asp Ser Glu Ala Glu Val Ser Leu Asp Lys
        420                 425                 430

atc aac ccc acc acg cag aat gga cag cac aag tta tga agtgctgtaa      1521
Ile Asn Pro Thr Thr Gln Asn Gly Gln His Lys Leu
    435                 440                 445

gggagggaaa tggcgtcatg ttacagaaga acacctcacc acatagagct ttgcgtcgat   1581

ccgtgcttac ataccacagc gtaagaggaa atagatccac aatgcgactc ggacgtgtgg   1641

ggtgg                                                               1646
```

<210> SEQ ID NO 28

-continued

<211> LENGTH: 445
<212> TYPE: PRT
<213> ORGANISM: Anguilla anguilla

<400> SEQUENCE: 28

```
Met Asp Leu Asn Leu Ser Thr Val Leu Asp Gly Asp Leu Pro Glu Lys
1               5                   10                  15

Asp Ser Ser Ala Arg Val Leu Thr Gly Cys Phe Leu Ser Leu Leu Ile
            20                  25                  30

Leu Thr Thr Leu Leu Gly Asn Thr Leu Val Cys Ala Ala Val Thr Arg
        35                  40                  45

Phe Arg His Leu Arg Ser Lys Val Thr Asn Phe Phe Val Ile Ser Leu
    50                  55                  60

Ala Ile Ser Asp Leu Leu Val Ala Ile Leu Val Met Pro Trp Lys Ala
65                  70                  75                  80

Ala Thr Glu Ile Val Gly Phe Trp Pro Phe Gly Ser Phe Cys Asn Val
                85                  90                  95

Trp Val Ala Phe Asp Ile Met Cys Ser Thr Ala Ser Ile Leu Asn Leu
            100                 105                 110

Cys Val Ile Ser Val Asp Arg Tyr Trp Ala Ile Ser Ser Pro Phe Arg
        115                 120                 125

Tyr Glu Arg Lys Met Thr Pro Lys Val Ala Phe Val Met Ile Ser Val
    130                 135                 140

Ala Trp Thr Leu Ser Val Leu Ile Ser Phe Ile Pro Val Gln Leu Asn
145                 150                 155                 160

Trp His Lys Ala Gln Ala Ala Gly Phe Pro Glu Leu Asn Gly Thr Phe
                165                 170                 175

Arg Glu Pro Pro Pro Pro Asp Asn Cys Asp Ser Ser Leu Asn Arg Thr
            180                 185                 190

Tyr Ala Ile Ser Ser Ser Leu Ile Ser Phe Tyr Ile Pro Val Ala Ile
        195                 200                 205

Met Ile Val Thr Tyr Thr Arg Ile Tyr Arg Ile Ala Gln Lys Gln Ile
    210                 215                 220

Arg Arg Ile Ser Ala Leu Glu Arg Ala Ala Glu Ser Ala Lys Asn Arg
225                 230                 235                 240

His Ser Ser Met Gly Asn Ser Ile Glu Ser Glu Ser Ser Phe Lys Met
                245                 250                 255

Ser Phe Lys Arg Glu Thr Lys Val Leu Lys Thr Leu Ser Val Ile Met
            260                 265                 270

Gly Val Phe Val Cys Cys Trp Leu Pro Phe Phe Ile Leu Asn Cys Met
        275                 280                 285

Val Pro Phe Cys Glu Gln Ala Pro Gln Gly Ala Ala Asp Leu Pro Cys
    290                 295                 300

Val Ser Ser Thr Thr Phe Asp Val Phe Val Trp Phe Gly Trp Ala Asn
305                 310                 315                 320

Ser Ser Leu Asn Pro Ile Ile Tyr Ala Phe Asn Ala Asp Phe Arg Lys
                325                 330                 335

Ala Phe Ser Thr Leu Leu Gly Cys His Arg Val Cys Ser Gly Gly Asn
            340                 345                 350

Ala Ile Glu Ile Val Ser Ile Asn Asn Asn Asn Gly Ala Ala Ala His
        355                 360                 365

Ser Tyr His Tyr Glu Thr Lys Gly His Ile Pro Lys Glu Ser Asn Val
    370                 375                 380

Ala Tyr Met Ile Pro His Ser Ile Leu Cys Gln Asp Glu Glu Leu Glu
```

-continued

```
385                 390                 395                 400

Lys Arg Glu Glu Asp Ser Ala Gly Met Lys Asp Leu Glu Lys Leu Ser
                405                 410                 415

Pro Ala Val Ser Gly Asp Leu Asp Ser Glu Ala Glu Val Ser Leu Asp
            420                 425                 430

Lys Ile Asn Pro Thr Thr Gln Asn Gly Gln His Lys Leu
        435                 440                 445


<210> SEQ ID NO 29
<211> LENGTH: 1694
<212> TYPE: DNA
<213> ORGANISM: Didelphis virginiana
<220> FEATURE:
<221> NAME/KEY: CDS
<222> LOCATION: (295)..(1635)
<223> OTHER INFORMATION:

<400> SEQUENCE: 29

gattagaact cttgtgggac ttgggttcaa tttcaaaact attacctgta ggactttgga      60

aagtcacatt ttgaccttga tttcctcatt ttgacaatta gcaggttaaa atagatgacc     120

ttgaaggctt cttgcagtgc aatttcttcg attctctgac ttaggttgca aattataaat     180

acatatctaa aaatttgctg ccagttgtta ttggaataca gacatctata taaaagagaa     240

gacatttcaa cagaagctct agatcaactt ggtgaaatat acaatagaga cata atg       297
                                                             Met
                                                             1

ccc ttg aat gac aca act atg gac aga aga ggg ctg gta gtg gaa agg       345
Pro Leu Asn Asp Thr Thr Met Asp Arg Arg Gly Leu Val Val Glu Arg
            5                   10                  15

gac ttc tcc ttc cgc atc ctt act gcc tgc ttc ctt tca cta ttg atc       393
Asp Phe Ser Phe Arg Ile Leu Thr Ala Cys Phe Leu Ser Leu Leu Ile
        20                  25                  30

ttg tct aca ctt ttg gga aat act ttg gtg tgt gca gct gtc atc agg       441
Leu Ser Thr Leu Leu Gly Asn Thr Leu Val Cys Ala Ala Val Ile Arg
    35                  40                  45

ttc cgc cac cta agg tcc aag gtg act aat ttc ttt gtc atc tcg ttg       489
Phe Arg His Leu Arg Ser Lys Val Thr Asn Phe Phe Val Ile Ser Leu
50                  55                  60                  65

gct gtt tct gac ctc tta gta gct gtc ttg gtc atg ccc tgg aaa gct       537
Ala Val Ser Asp Leu Leu Val Ala Val Leu Val Met Pro Trp Lys Ala
                70                  75                  80

gtt gca gag att gcg ggt ttc tgg ccc ttt ggc tcc ttc tgc aat atc       585
Val Ala Glu Ile Ala Gly Phe Trp Pro Phe Gly Ser Phe Cys Asn Ile
            85                  90                  95

tgg gtg gca ttt gat atc atg tgt tct acg gcc tcc att cta aac tta       633
Trp Val Ala Phe Asp Ile Met Cys Ser Thr Ala Ser Ile Leu Asn Leu
        100                 105                 110

tgt gtc atc agt gtt gat aga tat tgg gct att tcc agt ccc ttt cgc       681
Cys Val Ile Ser Val Asp Arg Tyr Trp Ala Ile Ser Ser Pro Phe Arg
    115                 120                 125

tat gag aga aaa atg acc ccc aag gca gcc ttc att ttg atc agt gtt       729
Tyr Glu Arg Lys Met Thr Pro Lys Ala Ala Phe Ile Leu Ile Ser Val
130                 135                 140                 145

gct tgg act ttg tct gtg ttg att tcc ttc att cca gta cag ttg aat       777
Ala Trp Thr Leu Ser Val Leu Ile Ser Phe Ile Pro Val Gln Leu Asn
                150                 155                 160

tgg cac aag gcc aga ccc ctg agc tca cca gat ggg aat gtt agt tcc       825
Trp His Lys Ala Arg Pro Leu Ser Ser Pro Asp Gly Asn Val Ser Ser
            165                 170                 175
```

-continued

```
caa gat gag aca atg gac aac tgt gac tct agc ctg agc agg aca tat      873
Gln Asp Glu Thr Met Asp Asn Cys Asp Ser Ser Leu Ser Arg Thr Tyr
        180                 185                 190

gcc atc tct tct tct ctt att agc ttt tac att cca gtg gct atc atg      921
Ala Ile Ser Ser Ser Leu Ile Ser Phe Tyr Ile Pro Val Ala Ile Met
    195                 200                 205

ata gtc aca tac acg agg atc tac agg att gca cag aag caa ata aga      969
Ile Val Thr Tyr Thr Arg Ile Tyr Arg Ile Ala Gln Lys Gln Ile Arg
210                 215                 220                 225

cga atc tca gct ttg gag aga gct gcc gtt cat gcc aag aac tgc cag     1017
Arg Ile Ser Ala Leu Glu Arg Ala Ala Val His Ala Lys Asn Cys Gln
                230                 235                 240

aac act act ggg aat ggg gca aat gtg gag tgt tcc cag cca gaa agt     1065
Asn Thr Thr Gly Asn Gly Ala Asn Val Glu Cys Ser Gln Pro Glu Ser
            245                 250                 255

tcc ttc aag atg tcc ttc aag aga gaa acc aaa gtt tta aag act ctg     1113
Ser Phe Lys Met Ser Phe Lys Arg Glu Thr Lys Val Leu Lys Thr Leu
        260                 265                 270

tca gtg atc atg gga gtg ttt gta tgc tgc tgg cta cct ttt ttc ata     1161
Ser Val Ile Met Gly Val Phe Val Cys Cys Trp Leu Pro Phe Phe Ile
    275                 280                 285

ttg aac tgc atg gta ccc ttc tgt gaa tct gat ttg cct tct ggg gaa     1209
Leu Asn Cys Met Val Pro Phe Cys Glu Ser Asp Leu Pro Ser Gly Glu
290                 295                 300                 305

aca aaa ccc ttc tgt att gat tct att acc ttt gat gtt ttc gtg tgg     1257
Thr Lys Pro Phe Cys Ile Asp Ser Ile Thr Phe Asp Val Phe Val Trp
                310                 315                 320

ttt gga tgg gca aat tcc tca ctg aac cct atc att tat gcc ttt aat     1305
Phe Gly Trp Ala Asn Ser Ser Leu Asn Pro Ile Ile Tyr Ala Phe Asn
            325                 330                 335

gct gac ttc cga aag gca ttt tct act ctc tta gga tgc tac agg ctc     1353
Ala Asp Phe Arg Lys Ala Phe Ser Thr Leu Leu Gly Cys Tyr Arg Leu
        340                 345                 350

tgt ccc act gcc aac aat gca ata gag aca gtt agc atc aac aat aat     1401
Cys Pro Thr Ala Asn Asn Ala Ile Glu Thr Val Ser Ile Asn Asn Asn
    355                 360                 365

ggg gct gtg ttt tca agc cat cat gag ccc aga ggg tcc att tct aag     1449
Gly Ala Val Phe Ser Ser His His Glu Pro Arg Gly Ser Ile Ser Lys
370                 375                 380                 385

gac tgt aat ctg gtt tac ctg att cca caa gct gtc acc tcc cga gac     1497
Asp Cys Asn Leu Val Tyr Leu Ile Pro Gln Ala Val Thr Ser Arg Asp
                390                 395                 400

cca aag aag gaa gaa ggt gga gga tcc aag cca ttg gag aaa acc tct     1545
Pro Lys Lys Glu Glu Gly Gly Gly Ser Lys Pro Leu Glu Lys Thr Ser
            405                 410                 415

cca gct tta tct gtc att ttg gat tat gaa gtt gat cta tct ttg gaa     1593
Pro Ala Leu Ser Val Ile Leu Asp Tyr Glu Val Asp Leu Ser Leu Glu
        420                 425                 430

aag att aac ccc atc aca cag aat gga caa cac aag acc tga             1635
Lys Ile Asn Pro Ile Thr Gln Asn Gly Gln His Lys Thr
    435                 440                 445

accgtaagat gaatcctgta aaaatatgct agtgaaaaca aaaaacaaaa accttctga    1694


<210> SEQ ID NO 30
<211> LENGTH: 446
<212> TYPE: PRT
<213> ORGANISM: Didelphis virginiana

<400> SEQUENCE: 30

Met Pro Leu Asn Asp Thr Thr Met Asp Arg Arg Gly Leu Val Val Glu
```

-continued

```
1               5                   10                  15

Arg Asp Phe Ser Phe Arg Ile Leu Thr Ala Cys Phe Leu Ser Leu Leu
            20                  25                  30

Ile Leu Ser Thr Leu Leu Gly Asn Thr Leu Val Cys Ala Ala Val Ile
        35                  40                  45

Arg Phe Arg His Leu Arg Ser Lys Val Thr Asn Phe Phe Val Ile Ser
    50                  55                  60

Leu Ala Val Ser Asp Leu Leu Val Ala Val Leu Val Met Pro Trp Lys
65                  70                  75                  80

Ala Val Ala Glu Ile Ala Gly Phe Trp Pro Phe Gly Ser Phe Cys Asn
                85                  90                  95

Ile Trp Val Ala Phe Asp Ile Met Cys Ser Thr Ala Ser Ile Leu Asn
            100                 105                 110

Leu Cys Val Ile Ser Val Asp Arg Tyr Trp Ala Ile Ser Ser Pro Phe
        115                 120                 125

Arg Tyr Glu Arg Lys Met Thr Pro Lys Ala Ala Phe Ile Leu Ile Ser
    130                 135                 140

Val Ala Trp Thr Leu Ser Val Leu Ile Ser Phe Ile Pro Val Gln Leu
145                 150                 155                 160

Asn Trp His Lys Ala Arg Pro Leu Ser Ser Pro Asp Gly Asn Val Ser
                165                 170                 175

Ser Gln Asp Glu Thr Met Asp Asn Cys Asp Ser Ser Leu Ser Arg Thr
            180                 185                 190

Tyr Ala Ile Ser Ser Ser Leu Ile Ser Phe Tyr Ile Pro Val Ala Ile
        195                 200                 205

Met Ile Val Thr Tyr Thr Arg Ile Tyr Arg Ile Ala Gln Lys Gln Ile
    210                 215                 220

Arg Arg Ile Ser Ala Leu Glu Arg Ala Ala Val His Ala Lys Asn Cys
225                 230                 235                 240

Gln Asn Thr Thr Gly Asn Gly Ala Asn Val Glu Cys Ser Gln Pro Glu
                245                 250                 255

Ser Ser Phe Lys Met Ser Phe Lys Arg Glu Thr Lys Val Leu Lys Thr
            260                 265                 270

Leu Ser Val Ile Met Gly Val Phe Val Cys Cys Trp Leu Pro Phe Phe
        275                 280                 285

Ile Leu Asn Cys Met Val Pro Phe Cys Glu Ser Asp Leu Pro Ser Gly
    290                 295                 300

Glu Thr Lys Pro Phe Cys Ile Asp Ser Ile Thr Phe Asp Val Phe Val
305                 310                 315                 320

Trp Phe Gly Trp Ala Asn Ser Ser Leu Asn Pro Ile Ile Tyr Ala Phe
                325                 330                 335

Asn Ala Asp Phe Arg Lys Ala Phe Ser Thr Leu Leu Gly Cys Tyr Arg
            340                 345                 350

Leu Cys Pro Thr Ala Asn Asn Ala Ile Glu Thr Val Ser Ile Asn Asn
        355                 360                 365

Asn Gly Ala Val Phe Ser Ser His His Glu Pro Arg Gly Ser Ile Ser
    370                 375                 380

Lys Asp Cys Asn Leu Val Tyr Leu Ile Pro Gln Ala Val Thr Ser Arg
385                 390                 395                 400

Asp Pro Lys Lys Glu Glu Gly Gly Gly Ser Lys Pro Leu Glu Lys Thr
                405                 410                 415

Ser Pro Ala Leu Ser Val Ile Leu Asp Tyr Glu Val Asp Leu Ser Leu
            420                 425                 430
```

-continued

```
Glu Lys Ile Asn Pro Ile Thr Gln Asn Gly Gln His Lys Thr
        435                 440                 445


<210> SEQ ID NO 31
<211> LENGTH: 4411
<212> TYPE: DNA
<213> ORGANISM: Sus scrofa
<220> FEATURE:
<221> NAME/KEY: CDS
<222> LOCATION: (1708)..(3048)
<223> OTHER INFORMATION:

<400> SEQUENCE: 31

ccgggcacag gctgcagtcc ggtattgacg caagctggac cgccgctacc ccggcggagg     60

cctaagcgag ccccccttcca gcgcaacgga gcccaccgac caggagcgct cgtgcgcgga    120

gccctctcgg cgagcggtga gtacaggccg cgcggggcac gtctcactct agttgggggg    180

gcacctggag accgctcagg tcggatccgg gcgggccgtt ctggctggta tgcgtgggag    240

ggtgagcagg gtcccagttt ccgtttggtc tttgggaaag gcttgggggg gttgacccca    300

ggaggcgctg catgtggggc ggagctctgc tttctggcaa ctcaggctta gttgagggtc    360

taacatggaa tattttctca gggacccctg tcgcgtgccg tcccagggtc cgggggtctg    420

aggtttaggg ggaggtaacc cagggcgggc gagagctcac ccggacgtcc cccgtccctt    480

tcgcccgcgg caccatccgg gagaaccacg tgcggctgtc ggccacctct ctgcctgtca    540

agagaagccc gcctccaggg caggggaggg gacgcggggg cggggtggct gtgccccgcg    600

ggaaccaggc cggcccgtga gcccgccagt gccagctcgt ctctccgcct cgtgttccca    660

cgggctcttg ggtgatagcg ggcagtttcg cgggcaggcg cagggctgtt cctcgaggga    720

ccagagacca ctcgaggggc gcccgggtgc tcggctcccg gagaaaggaa gcaaagaaac    780

tgcccgagtg actactacag gaggtgtcct cagtcaagga ggcgcctagc gcccgaaagc    840

ccttttcccg ggtctcgtcc attttgaagc atctctaacc ttctgagaca gtggcgcagc    900

gcctgctctc cgtggacttg gcccaggatc ctttttccga acccgcccca gcgaattttg    960

cgcatcgggt ggggagcaga gccccggctg cgcgcgcagg gcaggactca ggcgcgcctc   1020

cctccgttgt gcagctgcgg cgggcgcttg gggaatcctg ttctcggagc tccaggagca   1080

ttgagagaga ccacctcaag gcaaggtagg tggctctccc ggagttggat tgggcttggc   1140

aagtaaagat gcgatctgct caaatcttgg caaacgtcct cagctctctc tttgctttct   1200

agggctttcg gggagctgct gcggagtcag gggcttggag gtgcgaggca tgtattttca   1260

ctggcgcctc agaaagggag aattctctgt caccacccga gagcaacagc ccgtaaatgt   1320

gactacaatt gactagctcg gtcagaggcc tgggagtctc tgaactgaca gcttagaata   1380

tgctaaaaag ccagtgcttt ccatggggca ttgaagggcc atctggtccc cgtaacagtg   1440

acctgaagca aaggagtcag aagacagttg tagagagcaa gagggacctt ccgaggggct   1500

gtcttggacg gcccagggca ggctcctgcc gcccagttgt tgtggccttg tgatggcacg   1560

ctggtgaggt cctccaccca ggggagcaag tggcgctgag ccaggaccg cctggccagc   1620

caggactcct gcagctctga tcgaccccta atccccgcct aggaacttga ggggtgtcag   1680

aacccctctg ggctctccct caggaag atg agg acg ctg aac acc tcc acc atg   1734
                             Met Arg Thr Leu Asn Thr Ser Thr Met
                             1               5

gac ggc acc ggg ctg gtg gtg gag agg gac ttc tcc ttc cgc atc ctc     1782
Asp Gly Thr Gly Leu Val Val Glu Arg Asp Phe Ser Phe Arg Ile Leu
10                  15                  20                  25
```

-continued

```
acc gcc tgt ttc ctg tcg ctg ctc atc ctg tcc aca ctc ctg ggg aat      1830
Thr Ala Cys Phe Leu Ser Leu Leu Ile Leu Ser Thr Leu Leu Gly Asn
                30                  35                  40

acg ctg gtc tgt gcc gcc gtc atc agg ttc cga cac ctg cgt tcc aag      1878
Thr Leu Val Cys Ala Ala Val Ile Arg Phe Arg His Leu Arg Ser Lys
            45                  50                  55

gtg acc aac ttc ttc gtc atc tcc tta gcc gta tcg gat ctc ttg gtg      1926
Val Thr Asn Phe Phe Val Ile Ser Leu Ala Val Ser Asp Leu Leu Val
        60                  65                  70

gct gtc ttg gtc atg ccc tgg aaa gcg gtg gct gag atc gct ggc ttc      1974
Ala Val Leu Val Met Pro Trp Lys Ala Val Ala Glu Ile Ala Gly Phe
    75                  80                  85

tgg ccc ttt ggg tcc ttc tgt aac atc tgg gtg gcc ttt gac atc atg      2022
Trp Pro Phe Gly Ser Phe Cys Asn Ile Trp Val Ala Phe Asp Ile Met
90                  95                  100                 105

tgc tct acc gcg tcc atc ctc aac ctc tgt gtg atc agc gtg gac agg      2070
Cys Ser Thr Ala Ser Ile Leu Asn Leu Cys Val Ile Ser Val Asp Arg
                110                 115                 120

tac tgg gcc atc tct agc ccc ttc cgg tat gag agg aag atg acc ccc      2118
Tyr Trp Ala Ile Ser Ser Pro Phe Arg Tyr Glu Arg Lys Met Thr Pro
            125                 130                 135

aag gca gcc ttc att ctg atc agc gtg gca tgg act ctg tcc gtt ctc      2166
Lys Ala Ala Phe Ile Leu Ile Ser Val Ala Trp Thr Leu Ser Val Leu
        140                 145                 150

atc tcc ttt atc cca gtg cag ctc agc tgg cac aag gca aaa ccc acg      2214
Ile Ser Phe Ile Pro Val Gln Leu Ser Trp His Lys Ala Lys Pro Thr
    155                 160                 165

agc ccc tcc gat ggg aat gtc act tcc ctg ggc aag acc acc cac aac      2262
Ser Pro Ser Asp Gly Asn Val Thr Ser Leu Gly Lys Thr Thr His Asn
170                 175                 180                 185

tgt gac tcc agc ttg agc agg acc tat gcc att tca tcc tcc cta atc      2310
Cys Asp Ser Ser Leu Ser Arg Thr Tyr Ala Ile Ser Ser Ser Leu Ile
                190                 195                 200

agc ttt tac atc ccc gtg gcc atc atg att gtc acc tac acc agg atc      2358
Ser Phe Tyr Ile Pro Val Ala Ile Met Ile Val Thr Tyr Thr Arg Ile
            205                 210                 215

tac agg atc gcc cag aaa caa ata cgg cgc atc tcg gcc ttg gag agg      2406
Tyr Arg Ile Ala Gln Lys Gln Ile Arg Arg Ile Ser Ala Leu Glu Arg
        220                 225                 230

gca gcg gtc cac gcc aag aat tgc cag acc act gca ggt aat ggc aac      2454
Ala Ala Val His Ala Lys Asn Cys Gln Thr Thr Ala Gly Asn Gly Asn
    235                 240                 245

cct gcg gag tgt tct caa cca gaa agc tcc ttt aag atg tcc ttc aaa      2502
Pro Ala Glu Cys Ser Gln Pro Glu Ser Ser Phe Lys Met Ser Phe Lys
250                 255                 260                 265

aga gag act aaa gtc ctg aag acg ctg tcc gtg atc atg ggg gtg ttt      2550
Arg Glu Thr Lys Val Leu Lys Thr Leu Ser Val Ile Met Gly Val Phe
                270                 275                 280

gtg tgc tgc tgg ctc ccc ttc ttc atc ttg aac tgc atg gtg ccc ttc      2598
Val Cys Cys Trp Leu Pro Phe Phe Ile Leu Asn Cys Met Val Pro Phe
            285                 290                 295

tgt ggg tct ggg gag acc aag ccc ttc tgc att gat tcc atc acc ttt      2646
Cys Gly Ser Gly Glu Thr Lys Pro Phe Cys Ile Asp Ser Ile Thr Phe
        300                 305                 310

gac gtg ttt gtg tgg ttt ggg tgg gct aat tcc tcc ttg aac ccc atc      2694
Asp Val Phe Val Trp Phe Gly Trp Ala Asn Ser Ser Leu Asn Pro Ile
    315                 320                 325

atc tat gcc ttt aat gct gat ttt cgg aag gca ttt tcc acc ctc tta      2742
Ile Tyr Ala Phe Asn Ala Asp Phe Arg Lys Ala Phe Ser Thr Leu Leu
```

-continued

```
330                 335                 340                 345

gga tgc tac cga ctc tgc ccg acg tca act aat gcc ata gag acg gtg     2790
Gly Cys Tyr Arg Leu Cys Pro Thr Ser Thr Asn Ala Ile Glu Thr Val
            350                 355                 360

agc atc aat aac aat ggg gcc gtg gtg ttt tcc agc cat cac gag ccg     2838
Ser Ile Asn Asn Asn Gly Ala Val Val Phe Ser Ser His His Glu Pro
            365                 370                 375

cga ggc tcc atc tcc aag gac tgc aat ctg gtg tat ctg atc ccc cat     2886
Arg Gly Ser Ile Ser Lys Asp Cys Asn Leu Val Tyr Leu Ile Pro His
        380                 385                 390

gct gtg ggc tcc tct gag gac ctg aag aag gaa gag gca ggt ggc ata     2934
Ala Val Gly Ser Ser Glu Asp Leu Lys Lys Glu Glu Ala Gly Gly Ile
    395                 400                 405

gca agc ccc ttg gag aag ctg tcc cca gcc ctg tct gtc att ttg gat     2982
Ala Ser Pro Leu Glu Lys Leu Ser Pro Ala Leu Ser Val Ile Leu Asp
410                 415                 420                 425

tat gac act gat gtc tct cta gag aag atc cag ccc atc aca caa aat     3030
Tyr Asp Thr Asp Val Ser Leu Glu Lys Ile Gln Pro Ile Thr Gln Asn
            430                 435                 440

gga cag cac ccg acc tga actccaaggt gaatcttaac agacccactc            3078
Gly Gln His Pro Thr
            445

atcccaaaag ctagaggaga tttctctggg gcttgttgtg aagaaactga ggcgtgatga   3138

gaccctgagc tgtcaggcga gccctcctct gctgctttcc ctccaaccca ccactaacca   3198

cattttaaaa tacgttccaa tgtgttttct gtgttgttca tagtgaatca gagggacaca   3258

tgtgaggcga tcattcataa gggacgtgtc tttggctcca aaattatttt tagaaactga   3318

ttcttatctt aggactttaa aaaatagggc acagaagcaa gaaatgaaga gcttcattta   3378

aaaattagat ttttccggga aggaaatgag aagggttgag tttgctgtgt acaaacaggt   3438

gctaacactg gtccaagcaa agttttcaga ttgtaaaggt aggtgcatgc cttcataaat   3498

tattcctaaa aaagaattga gccttacaat aggaatggga tttttttttc cagtgttgat   3558

gctttgttgg tattggtttt atttatttat tgtattatat ggatatttaa aatttattat   3618

aataaatcta tatttatcat atttaatagg ataaatgaat gagttttctg agatcttaca   3678

atagcatttt ttgtccattg aactagcact ttatcagcca gtgaaacaaa tacacagact   3738

ctctgagttt ctaaatgctc atataaaact tccagaaata cagcaaagac taatagaaac   3798

tgaagttgtg aggattcctt aaaattcatt ggcaagaata aattcgaggt gagaattcac   3858

aaacgctcag attgtttttt ttttttcctc ctgaaaagat ttagaaagat tttttaaaaa   3918

gcatagctcc tcctgtgttc agattttttt aagtgacgaa gacttttgcc tgagaatgag   3978

ttacagttct gtaaatatct gaaataaaaa acagcttaag cgtccagctt gaaatttacg   4038

acctttggtg gtaataaaaa gtatttgcca ctttgtattt atgtaaaata actggccctc   4098

tctgtctttt ttcatttcct gtgtcagata gcttcctgaa ccaaataaat ggctgcctgg   4158

ttagatttgt ggaagacagt gagtttcctt aactcatgtg tcacaacagg ttcaccagtg   4218

gccaaggtca gatctttaca ccaccatctt accaggtcaa accaagcttt tcagtggggc   4278

tacttttcgt agtgctttaa tctgaactga gaattttttt ttttttaagt ctaaatgtat   4338

tctaacagat agtgcctcat tatcttcctc aagtaagaca cttctgttgg tggaaaaaaa   4398

gcagggcgac ccg                                                      4411
```

<210> SEQ ID NO 32
<211> LENGTH: 446

-continued

<212> TYPE: PRT
<213> ORGANISM: Sus scrofa

<400> SEQUENCE: 32

```
Met Arg Thr Leu Asn Thr Ser Thr Met Asp Gly Thr Gly Leu Val Val
1               5                   10                  15

Glu Arg Asp Phe Ser Phe Arg Ile Leu Thr Ala Cys Phe Leu Ser Leu
            20                  25                  30

Leu Ile Leu Ser Thr Leu Leu Gly Asn Thr Leu Val Cys Ala Ala Val
        35                  40                  45

Ile Arg Phe Arg His Leu Arg Ser Lys Val Thr Asn Phe Phe Val Ile
    50                  55                  60

Ser Leu Ala Val Ser Asp Leu Leu Val Ala Val Leu Val Met Pro Trp
65                  70                  75                  80

Lys Ala Val Ala Glu Ile Ala Gly Phe Trp Pro Phe Gly Ser Phe Cys
                85                  90                  95

Asn Ile Trp Val Ala Phe Asp Ile Met Cys Ser Thr Ala Ser Ile Leu
            100                 105                 110

Asn Leu Cys Val Ile Ser Val Asp Arg Tyr Trp Ala Ile Ser Ser Pro
        115                 120                 125

Phe Arg Tyr Glu Arg Lys Met Thr Pro Lys Ala Ala Phe Ile Leu Ile
    130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Val
                165                 170                 175

Thr Ser Leu Gly Lys Thr Thr His Asn Cys Asp Ser Ser Leu Ser Arg
            180                 185                 190

Thr Tyr Ala Ile Ser Ser Ser Leu Ile Ser Phe Tyr Ile Pro Val Ala
        195                 200                 205

Ile Met Ile Val Thr Tyr Thr Arg Ile Tyr Arg Ile Ala Gln Lys Gln
    210                 215                 220

Ile Arg Arg Ile Ser Ala Leu Glu Arg Ala Ala Val His Ala Lys Asn
225                 230                 235                 240

Cys Gln Thr Thr Ala Gly Asn Gly Asn Pro Ala Glu Cys Ser Gln Pro
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285

Phe Ile Leu Asn Cys Met Val Pro Phe Cys Gly Ser Gly Glu Thr Lys
    290                 295                 300

Pro Phe Cys Ile Asp Ser Ile Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Arg Lys Ala Phe Ser Thr Leu Leu Gly Cys Tyr Arg Leu Cys Pro
            340                 345                 350

Thr Ser Thr Asn Ala Ile Glu Thr Val Ser Ile Asn Asn Asn Gly Ala
        355                 360                 365

Val Val Phe Ser Ser His His Glu Pro Arg Gly Ser Ile Ser Lys Asp
    370                 375                 380

Cys Asn Leu Val Tyr Leu Ile Pro His Ala Val Gly Ser Ser Glu Asp
385                 390                 395                 400
```

-continued

```
Leu Lys Lys Glu Glu Ala Gly Gly Ile Ala Ser Pro Leu Glu Lys Leu
                405                 410                 415

Ser Pro Ala Leu Ser Val Ile Leu Asp Tyr Asp Thr Asp Val Ser Leu
            420                 425                 430

Glu Lys Ile Gln Pro Ile Thr Gln Asn Gly Gln His Pro Thr
        435                 440                 445
```

METHODS FOR IDENTIFYING COMPOUNDS FOR REGULATING MUSCLE MASS OR FUNCTION USING DOPAMINE RECEPTORS

CROSS REFERENCE TO RELATED APPLICATIONS

This application claims priority from U.S. Provisional Applications Ser. No. 60/349,620 filed on Jan. 18, 2002, which is herein incorporated by reference in its entirety.

TECHNICAL FIELD

The present invention relates to methods of identifying candidate compounds for regulating skeletal muscle mass or function or regulating the activity or expression of a dopamine receptor (dopamine receptor). The invention also relates to methods for the treatment of skeletal muscle atrophy or methods for inducing skeletal muscle hypertrophy using $D_1$ or $D_5$ dopamine receptors as the target for intervention and to methods of treating muscular dystrophies using $D_1$ or $D_5$ dopamine receptors as targets.

BACKGROUND

Dopamine Receptors

Dopamine has multiple physiological effects including central and peripheral activities. In the brain, dopamine controls a multitude of functions including locomotor activity, cognition, emotion, positive reinforcement, food intake and endocrine regulation. In the periphery, dopamine functions as a modulator of cardiovascular activity (both cardiac and vascular function), catecholamine release, hormone secretion, renal function and gastrointestinal motility (reviewed in Missale et al., 1998).

Dopamine mediates its action via at least 5 known dopamine receptors ($D_1$–$D_5$). These five receptors can be subdivided into two general groups based on their molecular structures, pharmacological activities, and physiological functions as the $D_1/D_5$ group ($D_1$-like) and the $D_{2/3/4}$ group ($D_2$-like) (Civelli et al., 1993; Gingrich et al., 1993; Jackson et al., 1994; Missale et al., 1998; O'Dowd, 1993). The $D_1/D_5$ subclass of receptors signal predominantly by coupling to Gαs, leading to the activation of adenylyl cyclase and the formation of cAMP (Gingrich et al., 1993; Missale et al., 1998). cAMP as a second messenger, has pleotropic effects including the activation of protein kinase A, phospholipase C activation, increase in intracellular calcium and sodium concentrations, changes in intracellular pH, mitogen-activated protein kinase induction, etc (Missale et al., 1998). The $D_{2/3/4}$ subclass of receptors signal mainly by coupling to Gαi, thereby inhibiting the activity of adenylyl cyclase (Gingrich et al., Missale et al., 1998). $D_1/D_5$ receptor subclass has been observed to also couple to Gαo, Gαi, and Gαq indicating that the signal transduction pathways activated by the $G_1/_5$ subclass may be quite complex (Kimura et al., 1995a; Sidhu et al., 1991; Wang et al., 1995). Dopamine receptors have been cloned from many species including human (Missale et al., 1998). Expression analysis of the dopamine receptors has demonstrated that the $D_1$ receptor is expressed widely in the rat brain including the striatum, nucleus accumbens, olfactory tubercle, limbic system, anterior cortex, thalamus, medulla, amygdala, mesencephalon, septum, anterior/posterior basal ganglia, and hypothalamus while the $D_5$ receptor is expressed in the rat hippocampus, lateral mamillary nucleus, parafascicular nucleus of the thalamus, cerebral cortex, lateral thalamus, substantia nigra, medial thalamus, and hippocampus; in the primate brain the $D_1$ and $D_5$ receptors are expressed in pyramidal neurons of prefontal, premotor, cingulate and entorhinal cortex, the hippocampus, the dentate gyrus, olfactory bulb, amygdala, caudate nucleus, and substantia nigra ($D_1$ only); in the periphery, the $D_1/D_5$ subbclass of receptors are expressed in blood vessels, adrenal gland, and kidney (Jackson et al., 1994; Missale et al., 1998).

Pharmacologically, agonists that selectively activate and antagonists that selectively block agonist activity of the $D_1/D_5$ receptor subclass have been described (Missale et al., 1998; Seeman et al., 1994; Sokoloff et al. 1995). These agonist and antagonists are able to differentiate the different dopamine receptors functionally and have been useful in matching biological activity with a specific dopamine receptor class.

Skeletal muscle is a plastic tissue, which readily adapts to changes in either physiological demand for work or metabolic need. Hypertrophy refers to an increase in skeletal muscle mass while skeletal muscle atrophy refers to a decrease in skeletal muscle mass. Acute skeletal muscle atrophy is traceable to a variety of causes including, but not limited to: disuse due to surgery, bed rest, or broken bones; denervation/nerve damage due to spinal cord injury, autoimmune disease, or infectious disease; glucocorticoid use for unrelated conditions; sepsis due to infection or other causes; nutrient limitation due to illness or starvation; and space travel. Skeletal muscle atrophy occurs through normal biological processes, however, in certain medical situations this normal biological process results in a debilitating level of muscle atrophy. For example, acute skeletal muscle atrophy presents a significant limitation in the rehabilitation of patients from immobilizations, including, but not limited to, those accompanying an orthopedic procedure. In such cases, the rehabilitation period required to reverse the skeletal muscle atrophy is often far longer than the period of time required to repair the original injury. Such acute disuse atrophy is a particular problem in the elderly, who may already suffer from substantial age-related deficits in muscle function and mass, because such atrophy can lead to permanent disability and premature mortality.

Skeletal muscle atrophy can also result from chronic conditions such as cancer cachexia, chronic inflammation, AIDS cachexia, chronic obstructive pulmonary disease (COPD), congestive heart failure, genetic disorders, e.g., muscular dystrophies, neurodegenerative diseases and sarcopenia (age associated muscle loss). In these chronic conditions, skeletal muscle atrophy can lead to premature loss of mobility, thereby adding to the disease-related morbidity.

Little is known regarding the molecular processes which control atrophy or hypertrophy of skeletal muscle. While the initiating trigger of the skeletal muscle atrophy is different for the various atrophy initiating events, several common biochemical changes occur in the affected skeletal muscle fiber, including a decrease in protein synthesis and an increase in protein degradation and changes in both contractile and metabolic enzyme protein isozymes characteristic of a slow (highly oxidative metabolism/slow contractile protein isoforms) to fast (highly glycolytic metabolism/fast contractile protein isoforms) fiber switch. Additional changes in skeletal muscle which occur include the loss of vasculature and remodeling of the extracellular matrix. Both fast and slow twitch muscle demonstrate atrophy under the appropriate conditions, with the relative muscle loss depending on the specific atrophy stimuli or condition. Importantly, all these changes are coordinately regulated and are switched on or off depending on changes in physiological and metabolic need.

The processes by which atrophy and hypertrophy occur are conserved across mammalian species. Multiple studies have demonstrated that the same basic molecular, cellular, and physiological processes occur during atrophy in both rodents and humans. Thus, rodent models of skeletal muscle atrophy have been successfully utilized to understand and predict human atrophy responses. For example, atrophy induced by a variety of means in both rodents and humans results in similar changes in muscle anatomy, cross-sectional area, function, fiber type switching, contractile protein expression, and histology. In addition, several agents have been demonstrated to regulate skeletal muscle atrophy in both rodents and in humans. These agents include anabolic steroids, growth hormone, insulin-like growth factor I, and β-adrenergic agonists. Together, these data demonstrate that skeletal muscle atrophy results from common mechanisms in both rodents and humans.

While some agents have been shown to regulate skeletal muscle atrophy and are approved for use in humans for this indication, these agents have undesirable side effects such as hypertrophy of cardiac muscle, neoplasia, hirsutism, androgenization of females, increased morbidity and mortality, liver damage, hypoglycemia, musculoskeletal pain, increased tissue turgor, tachycardia, and edema. Currently, there are no highly effective and selective treatments for either acute or chronic skeletal muscle atrophy. Thus, there is a need to identify other therapeutic agents which regulate skeletal muscle atrophy.

Muscular Dystrophies

Muscular dystrophies encompass a group of inherited, progressive muscle disorders, distinguished clinically by the selective distribution of skeletal muscle weakness. The two most common forms of muscle dystrophy are Duchenne and Becker dystrophies, each resulting from the inheritance of a mutation in the dystrophin gene, which is located at the Xp21 locus. Other dystrophies include, but are not limited to, limb-girdle muscular dystrophy which results from mutation of multiple genetic loci including the p94 calpain, adhalin, γ-sarcoglycan, and β-sarcoglycan loci; fascioscapulohumeral (Landouzy-Dejerine) muscular dystrophy, myotonic dystrophy, and Emery-Dreifuss muscular dystrophy. The symptoms of Duchenne muscular dystrophy, which occurs almost exclusively in males, include a waddling gait, toe walking, lordosis, frequent falls and difficulty in standing up and climbing stairs. Symptoms start at about 3–7 years of age with most patients confined to a wheelchair by 10–12 years and many die at about 20 years of age due to respiratory complications. Current treatment for Duchenne muscular dystrophy includes administration of prednisone (a corticosteroid drug), which while not curative, slows the decline of muscle strength and delays disability. Corticosteroids, such as prednisone, are believed to act by blocking the immune cell activation and infiltration which are precipitated by muscle fiber damage resulting from the disease. Unfortunately, corticosteroid treatment also results in skeletal muscle atrophy which negates some of the potential benefit of blocking the immune response in these patients. Thus, there is a need to identify therapeutic agents which slow the muscle fiber damage and delay the onset of disability in patients with muscular dystrophies, but cause a lesser degree of skeletal muscle atrophy than current therapies.

One problem associated with identification of compounds for use in the treatment of skeletal muscle atrophy or of muscular dystrophies has been the lack of good screening methods for the identification of such compounds. Applicants have now found that $D_1$ and $D_5$ dopamine receptors are involved in the regulation of skeletal muscle mass or function and that agonists of $D_1$ and $D_5$ dopamine receptors are able to block skeletal muscle atrophy and/or induce hypertrophy of skeletal muscle. The present invention solves the problem of identifying compounds for the treatment of muscle atrophy by providing screening methods using $D_1$ or $D_5$ dopamine receptors which can be used to identify candidate compounds useful for the treatment of muscle atrophy. The present invention also solves the problem of finding compounds for treatment of muscle dystrophies by providing a screening method to identify candidate compounds which activate both $D_1$ or $D_5$ dopamine receptors.

All documents cited are, in relevant part, incorporated herein by reference; the citation of any document is not to be construed as an admission that it is prior art with respect to the present invention.

SUMMARY OF THE INVENTION

The present invention relates to the use of $D_1$ or $D_5$ dopamine receptors to identify candidate compounds that are potentially useful in the treatment of skeletal muscle atrophy and or to induce skeletal muscle hypertrophy. The $D_1$ and $D_5$ receptors can be used to identify candidate compounds individually or in combination with each other. In particular, the invention provides in vitro methods for identifying candidate compounds for regulating skeletal muscle mass or function comprising contacting a test compound with a cell expressing $D_1$ or $D_5$ dopamine receptors, or contacting a test compound with isolated $D_1$ or $D_5$ dopamine receptors, and determining whether the test compound either binds to or activates the $D_1$ or $D_5$ dopamine receptors. Another embodiment of the invention relates to a method for identifying candidate therapeutic compounds from a group of one or more candidate compounds which have been determined to bind to or activate $D_1$ or $D_5$ dopamine receptors comprising administering the candidate compound to a non-human animal and determining whether the candidate compound regulates skeletal muscle mass or muscle function in the treated animal.

A further embodiment of the invention relates to a method for identifying candidate compounds for regulating skeletal muscle mass or function comprising, in any order: (i) contacting a test compound with a cell expressing a functional $D_1$ or $D_5$ dopamine receptor, and determining a level of activation of $D_1$ or $D_5$ dopamine receptors resulting from the test compound; (ii) contacting a test compound with a cell expressing a functional $D_1$ or $D_5$ dopamine receptor, and determining the level of activation of $D_1$ or $D_5$ resulting from the test compound; followed by (iii) comparing the level of $D_1$ or $D_5$ dopamine receptor activation and the level of activation; and (iv) identifying those test compounds that show similar activity toward $D_1$ or $D_5$ dopamine receptors and or show selectivity for $D_1$ or $D_5$ dopamine receptors as candidate compounds for regulating skeletal muscle mass or function.

The invention further provides methods for identifying candidate compounds that prolong or augment the agonist-induced activation of $D_1$ or $D_5$ dopamine receptors or of a $D_1$ or $D_5$ dopamine receptor signal transduction pathway. These methods comprise in any order or concurrently: (i) contacting a test compound with a cell which expresses functional $D_1$ or $D_5$ dopamine receptors; (ii) treating the cell with a $D_1$ or $D_5$ dopamine receptors agonist for a sufficient time and at a sufficient concentration to cause desensitization of the $D_1$ or $D_5$ dopamine receptors in control cells; followed by (iii) determining the level of activation of $D_1$ or $D_5$ dopamine receptors and identifying test compounds that prolong or augment the activation of a dopamine receptor or a dopamine receptor signal transduction pathway as candidate compounds for regulating skeletal muscle mass or function. In a particular embodiment, the present invention relates to a method of identifying candidate therapeutic compounds from a group of one or more candidate compounds determined to prolong or augment the activation of $D_1$ or $D_5$ dopamine receptors or activation of $D_1$ or $D_5$ dopamine receptors signal transduction pathway comprising: administering the candidate compound, in conjunction with a $D_1$ or $D_5$ dopamine receptors agonist, to a non-human animal and determining whether the candidate compound regulates skeletal muscle mass or function in the treated animal.

The invention further provides methods for identifying candidate compounds that increase $D_1$ or $D_5$ dopamine receptor expression comprising contacting a test compound with a cell or cell lysate containing a reporter gene operatively associated with a dopamine receptors gene regulatory element and detecting expression of the reporter gene. Test compounds that increase expression of the reporter gene are identified as candidate compounds for increasing $D_1$ or $D_5$ dopamine receptor expression. In a particular embodiment, the present invention relates to a method of determining whether those candidate compounds which increase $D_1$ or $D_5$ dopamine receptors expression can be used to regulate skeletal muscle mass or function in vivo by administering a candidate compound to a non-human animal and determining whether the candidate compound regulates skeletal muscle mass or function in the treated animal.

The present invention also relates to the use of $D_1$ or $D_5$ dopamine receptors agonists, expression vectors encoding a functional $D_1$ or $D_5$ dopamine receptor, expression vectors encoding a constitutively active $D_1$ or $D_5$ dopamine receptors or compounds that increase expression of $D_1$ or $D_5$ dopamine receptors to treat skeletal muscle atrophy. In particular, the invention provides methods of treating skeletal muscle atrophy, in a subject in need of such treatment, comprising administering to the subject a safe and effective amount of a $D_1$ or $D_5$ dopamine receptor agonist, an expression vector encoding a functional $D_1$ or $D_5$ dopamine receptor, an expression vector encoding a constitutively active $D_1$ or $D_5$ dopamine receptor, an expression vector encoding a dopamine receptor or dopamine receptor analog, or a compound that increases expression of $D_1$ or $D_5$ dopamine receptors. In a particular embodiment, the present invention relates to a method for treating skeletal muscle atrophy in a subject in need of such treatment comprising administering to the subject a safe and effective amount of a $D_1$ or $D_5$ dopamine receptor agonist in conjunction with a safe and effective amount of a compound that prolongs or augments the agonist-induced activation of $D_1$ or $D_5$ dopamine receptors, or of a $D_1$ and $D_5$ dopamine receptors signal transduction pathway.

The present invention also relates to the use of a $D_1$ or $D_5$ dopamine receptors agonist to increase skeletal muscle mass or function in a subject. In particular, the invention provides methods of increasing skeletal muscle mass or function in a subject in which such an increase is desirable, comprising identifying a subject in which an increase in muscle mass or function is desirable and administering to the subject a safe and effective amount of a dopamine agonist.

The invention further provides for pharmaceutical compositions comprising a safe and effective amount of $D_1$ or $D_5$ dopamine receptors agonist and a pharmaceutically-acceptable carrier. In a particular embodiment the pharmaceutical composition comprises a chimeric or human antibody specific for $D_1$ and $D_5$ dopamine receptors.

The present invention also provides for antibodies to $D_1$ and $D_5$ dopamine receptors and in particular to chimeric or human antibodies that are agonists of $D_1$ and $D_5$ dopamine receptors.

SEQUENCE LISTING DESCRIPTION

Each of the dopamine receptor nucleotide and protein sequences or dopamine receptor analog protein sequence included in the sequence listing, along with the corresponding Genbank or Derwent accession number(s) and animal species from which it is cloned, is shown in Table I. Also shown are accession numbers for related nucleotide sequences that encode identical, or nearly identical, amino acid sequences as the sequence shown in the sequence listing.

TABLE 1

| Sequence description | SEQ ID NO: nucleotide, amino acid | Species | Genbank (GB) or Derwent (D) Accession No. for nucleotide sequence | Related Genbank (GB) or Derwent (D) Accession Nos. |
|---|---|---|---|---|
| Dopamine $D_1$ Receptor | 1, 2 | *Homo sapiens* | X58987 (GB) | AAQ14954 (D)<br>AAQ43964 (D) |
| Dopamine $D_1$ Receptor variant | 3, 4 | *Homo sapiens* | S58542 (GB) | X55760 (GB) |
| Dopamine $D_1$ Receptor variant | 5, 6 | *Homo sapiens* | X55758 (GB) | |
| Dopamine $D_5$ Receptor | 7, 8 | *Homo sapiens* | X58454 (GB) | |
| Dopamine $D_5$ Receptor variant | 9, 10 | *Homo sapiens* | M67439 (GB) | |
| Dopamine $D_5$ Receptor variant | 11, 12 | *Homo sapiens* | I73473 (GB)<br>I12852 (GB) | |
| Dopamine $D_5$ Receptor | 13, 14 | *Homo sapiens pseudogene* | M67441 | M77186 (GB)<br>M67449 (GB)<br>I12853 (GB)<br>I12854 (GB)<br>M76064 (GB)<br>M75867 (GB)<br>I73474 (GB)<br>M77185 (GB)<br>I73473 (GB)<br>AAT99205 (D)<br>AAT99204 (D) |
| Dopamine $D_1$ Receptor | 15, 16 | *Rhesus macaque* | AF077862 | |
| Dopamine $D_5$ Receptor | 17, 18 | *Gorilla gorilla* | S77846 | |
| Dopamine $D_1$ Receptor | 19, 20 | *Rattus norvegicus* | S46131 | AAQ14955 (D) |
| Dopamine $D_1$ Receptor variant | 21, 22 | *Rattus norvegicus* | M35077 (GB)<br>I58000 (GB) | |
| Dopamine $D_5$ Receptor | 23, 24 | *Rattus norvegicus* | M69118 | |
| Dopamine $D_1$ Receptor | 25, 26 | *Gallus domesticus* | L36877 | |
| Dopamine $D_1$ Receptor | 27, 28 | *Anguilla anguilla* | U62918 | |
| Dopamine $D_1$ Receptor | 29, 30 | *Didelphis virginiana* | S67258 | |

TABLE 1-continued

| Sequence description | SEQ ID NO: nucleotide, amino acid | Species | Genbank (GB) or Derwent (D) Accession No. for nucleotide sequence | Related Genbank (GB) or Derwent (D) Accession Nos. |
|---|---|---|---|---|
| Dopamine $D_1$ Receptor | 31, 32 | *Sus scrofa* | U25681 | |

BRIEF DESCRIPTION OF THE FIGURES

FIGS. 1A and 1B also demonstrate the hypertrophy inducing effect of SKF 81297 on the non-denervated (normal) tibialis anterior (FIG. 1A) and medial gastrocnemius (FIG. 1B) muscles.

DETAILED DESCRIPTION OF THE INVENTION

Figure 1A:
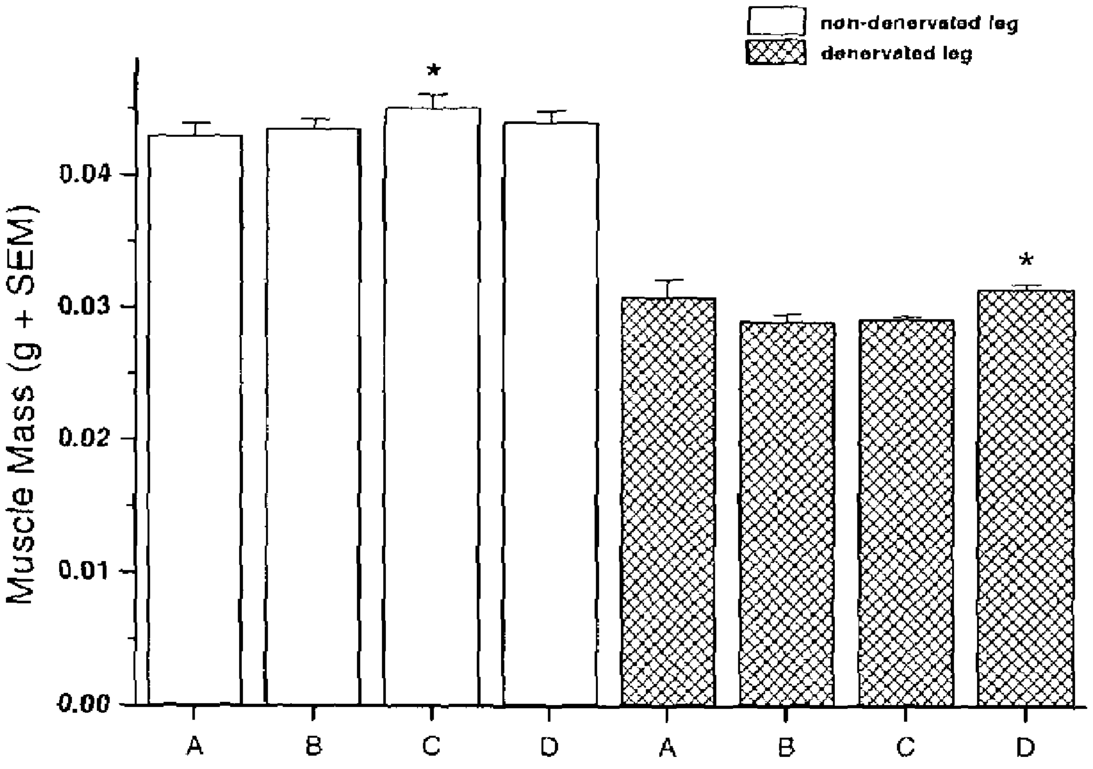
FIGS. 1A and 1B demonstrates the anti-atrophy effect of the $D_1$ and $D_5$ dopamine receptor agonists, SKF 81297 (administered subcutaneously, 2× daily), on the tibialis anterior (FIG. 1A) and medial gastrocnemius (FIG. 1B) muscles in the mouse sciatic nerve denervation atrophy model.

I. Terms and Definitions:

The following is a list of definitions for terms used herein.

"Agonist" means any compound, including, but not limited to, antibodies, that activates a receptor. For example, dopamine receptor agonists include, but are not limited to, dopamine and dopamine analogs; for example SKF81297 and Fenoldopam.

"Allelic variant" means a variant form of a given gene or gene product. One of skill in the art recognizes that a large number of genes are present in two or more allelic forms in a population and some genes have numerous alleles.

"Binding affinity" means the propensity for a ligand to interact with a receptor and is inversely related to the dissociation constant for a specific dopamine receptor ligand-dopamine receptor interaction. The dissociation constant can be measured directly via standard saturation, competition, or kinetics binding techniques or indirectly via pharmacological techniques involving functional assays and endpoints.

"Chimeric antibody" means an antibody that contains structural elements from two or more different antibody molecules, i.e., from different animal species. Chimeric antibodies include, but are not limited to, antibodies known as "humanized antibodies" which include, but are not limited to, chimeric antibodies generated by the technique known as complementarity determining region grafting.

"Dopamine receptor agonist" means a compound or molecule which has the ability to activate $D_1$ or $D_5$ dopamine receptors, or both. Activation of dopamine receptors can be measured as described hereinafter; using selective agonist such as, SKF 81297 and Fenoldopam $D_1/D_5$ selective receptor agonists.

"Dopamine receptor" means $D_1$ or $D_5$ dopamine receptor from any biological species.

The term "dopamine receptor" also includes truncated and/or mutated proteins wherein regions of the receptor molecule not required for ligand binding or signaling have been deleted or modified. For example, one of skill in the art will recognize that a dopamine receptor with one or more conservative changes in the primary amino acid sequence would be useful in the present invention. It is known in the art that substitution of certain amino acids with different amino acids with similar structure or properties (conservative substitutions) can result in a silent change, i.e., a change that does not significantly alter function. Conservative substitutes are well known in the art. For example, it is known that GPCRs can tolerate substitutions of amino acid residues in the transmembrane alpha-helices, which are oriented toward lipid, with other hydrophobic amino acids, and remain functional. $D_1$ and $D_5$ dopamine receptors differing from a naturally occurring sequence by truncations and/or mutations such as conservative amino acid substitutions are also included in the definition of dopamine receptors.

One of skill in the art would also recognize that dopamine receptors from a species other than those listed above, particularly mammalian species, would be useful in the present invention. One of skill in the art would further recognize that by using probes from the known dopamine receptor species' sequences, cDNA or genomic sequences homologous to the known sequence could be obtained from the same or alternate species by known cloning methods. Such are also included in the definition of and such $D_1$ and $D_5$ dopamine receptors are also included in the definition of $D_1$ and $D_5$ dopamine receptors.

In addition, one of skill in the art would recognize that functional allelic variants or functional splice variants of dopamine receptors might be present in a particular species and that these variants would have utility in the present invention. Such variants are also included in the definition of and such $D_1$ and $D_5$ dopamine receptors variants are also included in the definition of $D_1$ and $D_5$ dopamine receptors.

Fusions of $D_1$ and $D_5$ dopamine receptors polypeptide, or $D_1$ and $D_5$ dopamine receptors polypeptide fragment to a non-dopamine receptor polypeptide are referred to as dopamine receptor fusion proteins. Using known methods, one of skill in the art would be able to make fusion proteins of a $D_1$ and $D_5$ dopamine receptors that, while different from native and $D_1$ and $D_5$ dopamine receptors, would remain useful in the present invention. For example the non-dopamine receptor polypeptide may be a signal (or leader) polypeptide sequence which co-translationally or post-translationally directs transfer of the protein from its site of synthesis to another site (e.g., the yeast (x-factor leader). Or the non-dopamine receptor polypeptide may be added to facilitate purification or identification of the dopamine receptor (e.g., poly-His, or Flag peptide). $D_1$ and $D_5$ dopamine receptors fusion proteins are also included within the definition of $D_1$ and $D_5$ dopamine receptors.

"$D_1$ and $D_5$ dopamine receptors signal transduction pathway" means any signaling pathway (e.g., cAMP, MAP kinase) or combination of signaling pathways that are modulated by the binding of endogenous or exogenous ligands to $D_1$ and $D_5$ dopamine receptors.

"Fenoldopam" is 6-chloro-2,3,4,5-tetrahydro-1-(4-hydroxyphenyl)-[1H]-3-benzazepine-7,8-diol, also known as Corlopam®

"Functional dopamine receptors" refers to dopamine receptors, which bind dopamine receptor agonists in vivo or in vitro and are activated as a result of ligand binding.

"Fusion gene" means two or more DNA coding sequences operably associated so as to encode one hybrid protein. A "fusion protein" is the protein product of a fusion gene.

"Inhibit" means to partially or completely block a particular process or activity. For example, a compound inhibits skeletal muscle atrophy if it either completely or partially prevents muscle atrophy.

"Operably associated" refers two DNA sequences where the nature of the linkage between the two DNA sequences does not (1) result in the introduction of a frame-shift mutation, (2) interfere with the ability of a promoter region to direct the transcription of the coding sequences, or (3) interfere with the ability of the corresponding RNA transcript to be translated into a protein. For example, a coding sequence and regulatory sequences are operably associated when they are covalently linked in such a way as to place the transcription of the coding sequence under the influence or control of the regulatory sequences. Thus, a promoter region is operably associated with a coding sequence when the promoter region is capable of effecting transcription of that DNA sequence such that the resulting transcript is capable of being translated into the desired protein or polypeptide.

"Percent identity" means the percentage of nucleotides or amino acids that two sequences have in common, calculated as follows. To calculate the percent identity for a specific sequence (the query), the relevant part of the query sequence is compared to a reference sequence using the BestFit comparison computer program, Wisconsin Package, Version 10.1, available from the Genetics Computer Group, Inc. This program uses the algorithm of Smith and Waterman, *Advances in Applied Mathematics*, Issue 2: 482–489 (1981). Percent identity is calculated with the following default parameters for the BestFit program: the scoring matrix is blosum62.cmp, the gap creation penalty is 8 and the gap extension penalty is 2. When comparing a sequence to the reference sequence, the relevant part of the query sequence is that which is derived from a dopamine receptor sequence. For example, where the query is a dopamine receptor/purification tag fusion protein, only the dopamine receptor polypeptide portion of the sequence is aligned to calculate the percent identity score.

"Polypeptide" means any chain of amino acids, regardless of length or post-translational modification (e.g., phosphorylation or glycosylation).

"Promoter" means a DNA sequence which controls the initiation of transcription and the rate of transcription from a gene or coding region.

"Prophylactic treatment" means preventive treatment of a subject, not currently exhibiting signs of skeletal muscle atrophy, in order to completely or partially block the occurrence of skeletal muscle atrophy. One of skill in the art would recognize that certain individuals are at risk for skeletal muscle atrophy as discussed in the background section herein. Furthermore, one of skill in the art would recognize that if the biochemical changes leading to skeletal muscle atrophy are appropriately regulated, that the occurrence of atrophy would be prevented or reduced in at-risk individuals. For example, muscular dystrophy patients beginning treatment with corticosteroids are at risk for developing skeletal muscle atrophy indicating that prophylactic treatment of such patients would be appropriate.

"Regulate" in all its grammatical forms, means to increase, decrease or maintain, e.g., to regulate skeletal muscle mass or function means to increase, decrease or maintain the level of skeletal muscle mass or function.

"Regulation of skeletal muscle mass or function" includes regulation of skeletal muscle mass, skeletal muscle function or both.

"Regulatory element" means a DNA sequence that is capable of controlling the level of transcription from an operably associated DNA sequence. Included within this definition of regulatory element are promoters and enhancers. E.g., a dopamine receptor gene regulatory element is a DNA sequence capable of controlling the level of transcription from the dopamine receptor gene.

"Reporter gene" means a coding sequence whose product can be detected, preferably quantitatively, wherein the reporter gene is operably associated with a heterologous promoter or enhancer element which is responsive to a signal which is to be measured. The promoter or enhancer element in this context is referred to herein as a "responsive element".

"SKF 81297" is 6-chloro-7,8-dihydroxyl-1-phenyl-2,3,4,5-tetrahydro-1H-3-benzazepine purchased from RBI/Sigma, Natick, Mass.

"Selective agonist" means that the agonist has significantly greater activity toward a certain receptor(s) compared with other receptors, not that it is completely inactive with regard to other receptors. For example, $D_1$ and $D_5$ dopamine receptor selective agonists are not limited to SKF 81297 and Fenoldopam.

"SKF" means SmithKline French

"Skeletal muscle hypertrophy" means an increase in skeletal muscle mass or skeletal muscle function or both.

"Skeletal muscle atrophy" means the same as "muscle wasting" and means a decrease in skeletal muscle mass or skeletal muscle function or both.

"Splice variant" means a mRNA or protein which results from alternative exon usage. One of skill in the art recognizes that, depending on cell type, or even within a single cell type, a mRNA may be expressed in a different form, as a splice variant, and thus the translated protein will be different depending upon the mRNA that is expressed.

A "therapeutically effective amount" of a substance is an amount capable of producing a medically desirable result in a treated patient, e.g., decreases skeletal muscle atrophy, increases skeletal muscle mass or increases skeletal muscle function, with an acceptable benefit: risk ratio; in a human or non-human mammal.

"Therapeutic treatment" means treatment of a subject in which an increase in muscle mass or muscle function is desirable. For example, treatment of a subject currently exhibiting signs of skeletal muscle atrophy in order to partially or completely reverse the skeletal muscle atrophy that has occurred or to completely or partially block the occurrence of further skeletal muscle atrophy would be therapeutic treatment of that subject. The term "therapeutic treatment" also includes, for example, treatment of a subject not exhibiting signs of skeletal muscle atrophy to induce skeletal muscle hypertrophy, e.g., treatment of a livestock animal to increase muscle mass.

The term "treatment" means prophylactic or therapeutic treatment.

Unless otherwise defined, all technical and scientific terms used herein have the same meaning as commonly understood by one of ordinary skill in the arts of protein chemistry, pharmacology, or molecular biology. The methods, materials and examples described herein are not intended to be limiting. Other methods and materials similar or equivalent to those described herein can be used in the practice or testing of the present invention.

II. The Role of Dopamine Receptors in Regulation of Skeletal Muscle Mass

One of skill in the art would recognize the utility of the present invention given the information in the prior art and the teachings below. The results described herein demonstrate that administration of a dopamine receptor agonist which activates both $D_1$ and $D_5$ dopamine receptors (selective dopamine receptor agonist) but not the $D_{2/3/4}$ dopamine receptors blocks and/or inhibits the skeletal muscle atrophy inducing effect of denervation and disuse treatment in models of skeletal muscle atrophy. Furthermore, results demonstrate that administration of selective dopamine receptor agonist show a hypertrophy inducing effect. Together, these data demonstrate the modulatory role of the $D_1$ and $D_5$ dopamine receptors in the process of skeletal muscle atrophy. The specific role of dopamine receptors in vivo was investigated using the pharmacological agents, SKF81297 (RBI/Sigma, Natick, Mass.) and Fenoldopam (Corlopam®), which are selective agonists for $D_1$ and $D_5$ dopamine receptors in various models of skeletal muscle atrophy, described hereinafter. These agents have been well characterized and are described in the scientific literature.

Figure 2:
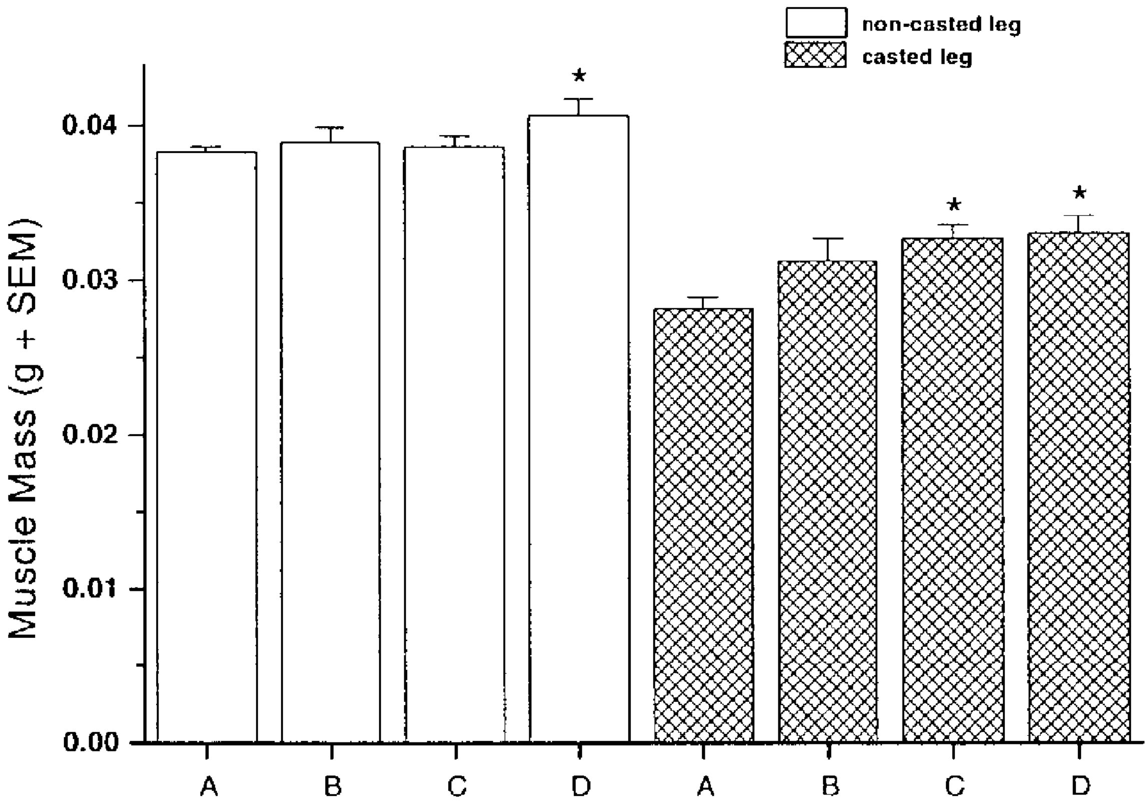
FIG. 2 demonstrates the anti-atrophy effect of the $D_1$ and $D_5$ dopamine receptor agonists, SKF 81297 (administered subcutaneously, 2× daily), on casting-induced atrophy of the tibialis anterior muscle and the hypertrophy inducing effect of SKF 81297 on the non-casted (normal) tibialis anterior muscle.

FIG. 2 demonstrates the anti-atrophy effect of the $D_1$ and $D_5$ dopamine receptor agonists, SKF 81297 (administered subcutaneously, 2× daily), on casting-induced atrophy of the tibialis anterior muscle and the hypertrophy inducing effect of SKF 81297 on the non-casted (normal) tibialis anterior muscle.

Figure 3:
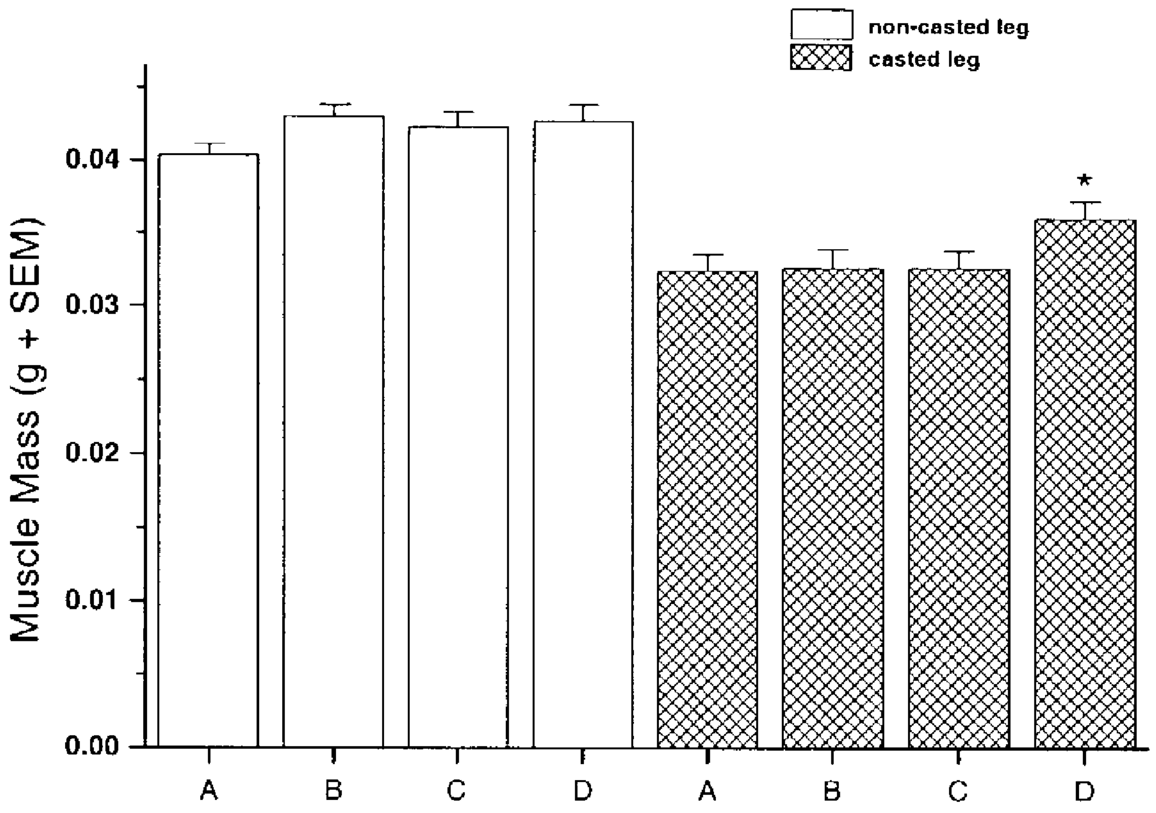
FIG. 3 demonstrates the anti-atrophy effect of the $D_1$ and $D_5$ dopamine receptor agonists, fenoldopam (administered subcutaneously, 2× daily), on casting-induced atrophy of the medial gastrocnemius muscle.

FIG. 3 demonstrates the anti-atrophy effect of the $D_1$ and $D_5$ dopamine receptor agonists, fenoldopam (administered subcutaneously, 2× daily), on casting-induced atrophy of the medial gastrocnemius muscle.

Figure 1B:
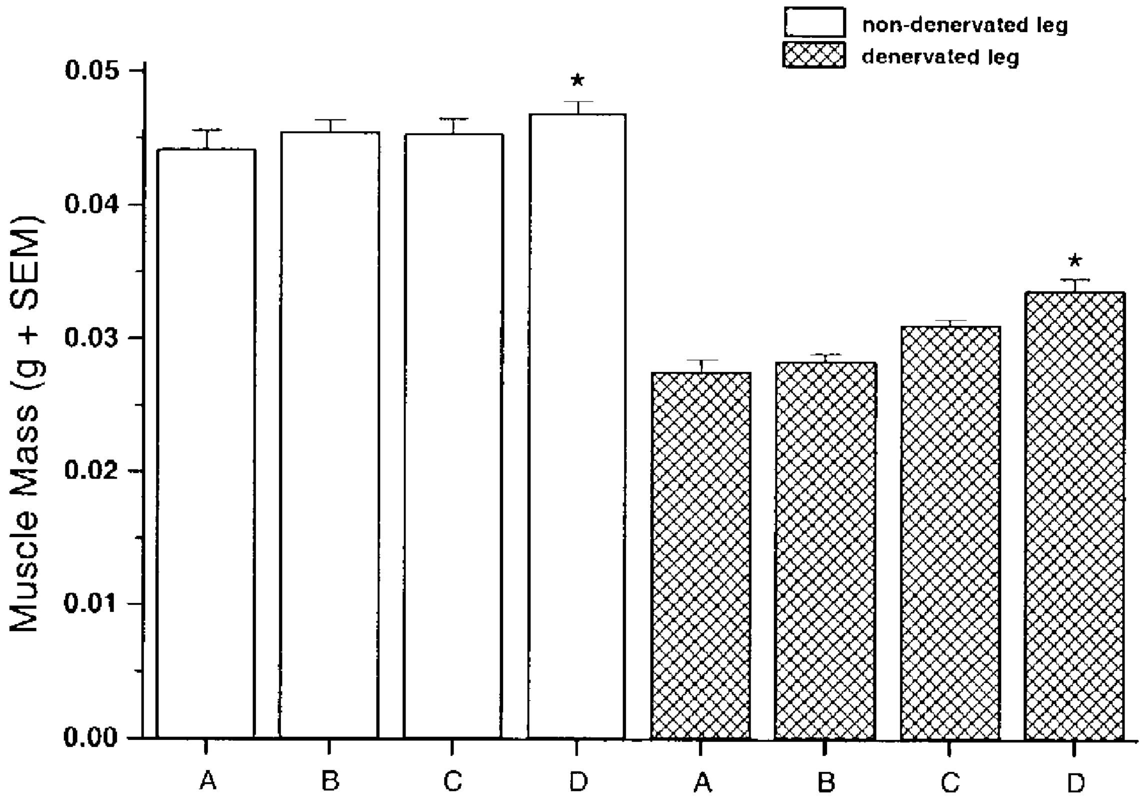

Specifically, FIG. 1 (FIG. 1.) shows that SKF 81297 inhibits denervation-induced atrophy of the tibialis anterior (FIG. 1A) medial gastrocnemius (FIG. 1B) muscles in a mouse sciatic nerve denervation atrophy model. In addition, FIG. 1 demonstrates that SKF 81297 induces hypertrophy in the normal (non-denervated) tibialis anterior (FIG. 1A) and medial gastrocnemius (FIG. 1B) muscles. Legend: A—physiological saline (control); B—SKF 81297 (0.3 mg/kg)+theophylline; C—SKF 81297 (1.0 mg/kg)+theophylline; D—SKF 81297 (3.0 mg/kg)+theophylline. *–$p \leqq 0.05$ compared to saline. Following denervation of the right sciatic nerve, male mice were injected subcutaneously in the midscapular region twice daily with SKF 81297, at the doses indicated above or vehicle control (physiological saline) for nine days. SKF 81297 was co-administered with twice daily intra-peritoneal dosing of the phosphodiesterase inhibitor theophylline (30 mg/kg). On day nine, the tibialis anterior and medial gastrocnemius muscles were removed and weighed to determine the degree of atrophy.

FIG. 2 (FIG. 2.) demonstrates that SKF 81297 inhibits disuse-induced atrophy of the tibialis anterior muscle. In addition, statistically significant hypertrophy of the tibialis anterior muscles of the non-casted leg was also observed with SKF 81297 treatment. Legend: A—physiological saline (control); B—SKF 81297 (0.3 mg/kg)+theophylline; C—SKF 81297 (1.0 mg/kg)+theophylline; D—SKF 81297 (3.0 mg/kg)+theophylline; *–$p \leqq 0.05$ compared to saline. Following casting of the right hind leg, male mice were injected subcutaneously in the midscapular region twice daily, with SKF 81297 or vehicle control (physiological saline) for ten days at the daily delivered dose indicated. SKF 81297 was co-administered with twice daily intra-peritoneal dosing of the phosphodiesterase inhibitor theophylline (30 mg/kg). On day ten, the tibialis anterior muscle was removed and weighed to determine the degree of atrophy.

FIG. 3 (FIG. 3.) demonstrates that fenoldopam inhibits disuse-induced atrophy of the medial gastrocnemius muscle. Legend: A—physiological saline (control); B—fenoldopam (0.3 mg/kg); C—fenoldopam (1.0 mg/kg); D—fenoldopam (3.0 mg/kg); *–$p \leqq 0.05$ compared to saline. Following casting of the right hind leg, male mice were injected subcutaneously in the midscapular region twice daily, with fenoldopam or vehicle control (physiological saline) for ten days at the daily delivered dose indicated. On day ten, the medial gastrocnemius muscle was removed and weighed to determine the degree of atrophy.

III. Preparation of Dopamine Receptors, Ropamine Receptor or Dopamine Receptor Analogs, or Cell Lines Expressing Dopamine Receptors $D_1$ and $D_5$ dopamine receptors can be prepared for a variety of uses, including, but not limited to, the generation of antibodies, use as reagents in the screening assays of the present invention, and use as pharmaceutical reagents for the treatment of skeletal muscle atrophy. It will be clear to one of skill in the art that, for certain embodiments of the invention, purified polypeptides will be most useful, while for other embodiments cell lines expressing the polypeptides will be most useful. For example, in situations where it is important to retain the structural and functional characteristics of the dopamine receptor, e.g., in a screening method to identify candidate compounds which activate dopamine receptors, it is desirable to use cells which express functional dopamine receptors.

Where the source of dopamine receptors is a cell line expressing the polypeptide, the cells may, for example, endogenously express dopamine receptor, have been stimulated to increase endogenous dopamine receptor expression or have been genetically engineered to express a dopamine receptor. Methods for determining whether a cell line expresses a polypeptide of interest are known in the art, for example, detection of the polypeptide with an appropriate antibody, use of a DNA probe to detect mRNA encoding the protein (e.g., northern blot or PCR techniques), or measuring binding of an agent selective for the polypeptide of interest (e.g., a radiolabeled selective agonist).

The use of recombinant DNA technology in the preparation of $D_1$ and $D_5$ dopamine receptors, or of cell lines expressing these polypeptides is particularly contemplated. Such recombinant methods are well known in the art. To express recombinant $D_1$ and $D_5$ dopamine receptors, an expression vector that comprises a nucleic acid which encodes the polypeptide of interest under the control of one or more regulatory elements, is prepared. Genomic or cDNA sequences encoding and $D_1$ and $D_5$ dopamine receptors from several species have been described and are readily available from the GenBank database (available at <http://www.ncbi.nlm.nih.gov/>) or Derwent database (available at <http://www.derwent.co.uk/geneseq/index.html>) as well as in the sequence listing for this application. The accession numbers for and $D_1$ and $D_5$ dopamine receptors sequences and corresponding SEQ ID NOS. are shown in Table I. Using this publicly available sequence information, one means of isolating a nucleic acid molecule encoding a $D_1$ and $D_5$ dopamine receptor is to screen a genomic DNA or cDNA library with a natural or artificially synthesized DNA probe, using methods well known in the art, e.g., by PCR amplification of the sequence from an appropriate library.

Another method is to use oligonucleotide primers specific for the receptor of interest to PCR amplify the cDNA directly from mRNA isolated from a particular tissue (such as skeletal muscle). Such isolated mRNA is commercially available. One of skill in the art would also recognize that by using nucleic acid probes corresponding to portions of the known dopamine receptor sequences the homologous cDNAs or genomic sequences from other species can be obtained using known methods. Particularly useful in the methods of the present invention are dopamine receptors from the species including, but not limited to, human, mouse, rat, pig, monkey, chimpanzee, marmoset, dog, cow, sheep, cat, chicken and turkey. By methods well known in the art, the isolated nucleic acid molecule encoding the dopamine receptor of interest is then ligated into a suitable expression vector. The expression vector, thus prepared, is expressed in a host cell and the host cells expressing the receptor are used directly in a screening assay or the receptor is isolated from the host cells expressing the receptor and the isolated receptor is used in a screening assay.

The host-expression vector systems that may be used for purposes of the invention include, but are not limited to: microorganisms such as bacteria (e.g., *E. coli, B. subtilis*) transformed with recombinant bacteriophage DNA, plasmid DNA, or cosmid DNA expression vectors containing dopamine receptor nucleotide sequences; yeast (e.g., *Saccharomyces, Pichia*) transformed with recombinant yeast expression vectors containing dopamine receptor nucleotide sequences; insect cell systems infected with recombinant virus expression vectors (e.g., baculovirus) containing dopamine receptor nucleotide sequences; plant cell systems infected with recombinant virus expression vectors (e.g., cauliflower mosaic virus, tobacco mosaic virus) or transformed with recombinant plasmid expression vectors (e.g., Ti plasmid) containing dopamine receptor nucleotide sequences; or mammalian cell systems (e.g., COS, CHO, HEK293, NIH3T3) harboring recombinant expression constructs containing promoters derived from the genome of mammalian cells (e.g., metallothionein promoter) or from mammalian viruses (e.g., retrovirus LTR) and also containing dopamine receptor nucleotide sequences.

The host cell is used to produce the polypeptide of interest. Because the dopamine receptor is a membrane bound molecule, it is purified from the host cell membranes or the dopamine receptor is utilized while anchored in the cell membrane, i.e., whole cells or membrane fractions of cells are used. Purification or enrichment of the dopamine receptors from such expression systems is accomplished using appropriate detergents and lipid micelles by methods well known to those skilled in the art.

In bacterial systems, a number of expression vectors may be advantageously selected depending upon the use intended for the gene product being expressed. For example, when a large quantity of such protein is produced for the generation of antibodies to dopamine receptors, vectors which direct the expression of high levels of protein products are desirable. One skilled in the art is able to generate such vector constructs and purify the proteins by a variety of methodologies including selective purification technologies such as fusion protein selective columns and antibody columns, and non-selective purification technologies.

In an insect protein expression system, the baculovirus *A. californica* nuclear polyhedrosis virus (AcNPV), is used as a vector to express foreign genes in *S. frugiperda* cells. In this case, dopamine receptor nucleotide sequences are cloned into non-essential regions of the virus and placed under the control of an AcNPV promoter. The recombinant viruses are then used to infect cells in which the inserted gene is expressed and the protein is purified by one of many techniques known to one skilled in the art.

In mammalian host cells, a number of viral-based expression systems may be utilized. Utilization of these expression systems often requires the creation of specific initiation signals in the vectors for efficient translation of the inserted nucleotide sequences. This is particularly important if a portion of the dopamine receptor gene is used which does not contain the endogenous initiation signal. The placement of this initiation signal, in frame with the coding region of the inserted nucleotide sequence, as well as the addition of transcription and translation enhancing elements and the purification of the recombinant protein, are achieved by one of many methodologies known to one skilled in the art. Also important in mammalian host cells is the selection of an appropriate cell type which is capable of the necessary post translational modifications of the recombinant protein. Such modifications, for example, cleavage, phosphorylation, glycosylation, etc., require the selection of the appropriate host cell which contains the modifying enzymes. Such host cells include, but are not limited to, CHO, HEK293, NIH3T3, COS, etc. and are known by those skilled in the art.

For long term, high expression of recombinant proteins, stable expression is preferred. For example, cell lines that stably express dopamine receptors may be engineered. One of skill in the art, following known methods such as electroporation, calcium phosphate transfection, or liposome-mediated transfection, can generate a cell line that stably expresses dopamine receptors. This is usually accomplished by transfecting cells using expression vectors which contain appropriate expression control elements (e.g., promoter sequences, enhancer sequences, transcriptional termination sequences, polyadenylation sites, translational start sites, etc.), a selectable marker, and the gene of interest. The selectable marker may either be contained within the same vector, as the gene of interest, or on a separate vector, which is co-transfected with the dopamine receptor sequence containing vector. The selectable marker in the expression vector may confer resistance to the selection and allows cells to stably integrate the vector into their chromosomes and to grow to form foci which in turn can be cloned and expanded into cell lines. Alternatively, the expression vector may allow selection of the cell expressing the selectable marker utilizing a physical attribute of the marker, i.e., expression of Green Fluorescent Protein (GFP) allows for selection of cells expressing the marker using fluorescence activated cell sorting (FACS) analysis.

One of skill in the art is able to select an appropriate cell type for transfection in order to allow for selection of cells into which the gene of interest has been successfully integrated. For example, where the selectable marker is herpes simplex virus thyrmidine kinase, hypoxanthine-guanine phosphoribosyltransferase or adenine phosphoribosyltransferase, the appropriate cell type would be tk-, hgprt- or aprt-cells, respectively. Or, normal cells can be used where the selectable marker is dhfr, gpt, neo or hygro which confer resistance to methotrexate, mycophenolic acid, G-418 or hygromycin, respectively. Such recombinant cell lines are useful for identification of candidate compounds that affect the dopamine receptor activity.

IV. Preparation of Dopamine Receptor Antibodies

Antibodies that selectively recognize one or more epitopes of a dopamine receptor are also encompassed by the invention. Such antibodies include, e.g., polyclonal antibodies, monoclonal antibodies, chimeric antibodies, human antibodies, single chain antibodies, Fab fragments, $F(ab')_2$ fragments, molecules produced using a Fab expression library, human antibodies (polyclonal or monoclonal) produced in transgenic mice and epitope binding fragments of any of the above. For therapeutic uses, chimeric or human antibodies are preferred; human antibodies are most preferred.

The antibodies can be utilized in conjunction with the compound screening schemes described herein for the evaluation of test compounds, e.g., for immobilization of dopamine receptor polypeptides or such antibodies can be used in conjunction with gene therapy techniques to evaluate, for example, the expression of dopamine receptors either in cells or directly in patient tissues in which these genes have been introduced. In addition, antibodies of the present invention are useful in the treatment of skeletal muscle atrophy. Antibodies selective for the dopamine receptor can be screened by the methods of the present invention to identify a subset of the antibodies that are dopamine receptor agonists. In addition, anti-idiotype antibodies generated against antibodies specific for dopamine receptor may be useful as dopamine receptor agonists and like anti-dopamine receptor antibodies may be screened for their ability to activate the dopamine receptor by methods of the present invention.

For the production of antibodies, a variety of host animals may be immunized by injection with dopamine receptors, anti-dopamine receptor antibody, or immunogenic fragments thereof by methods well known in the art. For preparation of an anti-idiotype antibody the immunogen is an anti-dopamine receptor antibody. Production of anti-idiotype antibodies is described, for example, in U.S. Pat. No. 4,699,880, incorporated herein by reference. Suitable host animals include, but are not limited to, rabbits, mice, goats, sheep and horses. Immunization techniques are well known in the art. Polyclonal antibodies can be purified from the serum of the immunized animals, or monoclonal antibodies can be generated by methods that are well known in the art. These techniques include, but are not limited to, the well-known hybridoma techniques of Kohler and Milstein, human B-cell hybridoma techniques, and the EBV hybridoma technology. Monoclonal antibodies may be of any immunoglobulin class, including IgG, IgE, IgM, IgA, and IgD containing either kappa or lambda light chains.

Because of the immunogenicity of non-human antibodies in humans, chimeric antibodies are preferred to non-human antibodies when used for therapeutic treatment of human patients. Techniques of producing and using chimeric antibodies are known in the art, and are described in, for example, U.S. Pat. Nos. 5,807,715; 4,816,397; 4,816,567; 5,530,101; 5,585,089; 5,693,761; 5,693,762; 6,180,370; and 5,824,307, all incorporated herein by reference.

Completely human antibodies are particularly desirable for therapeutic treatment of human patients because they are less immunogenic than non-human antibodies or chimeric antibodies. Such antibodies can be produced using transgenic mice which are substantially incapable of expressing endogenous immunoglobulin heavy and light chain genes, but which can express human heavy and light chain genes. The transgenic mice are immunized in the normal fashion with a selected antigen, e.g., all or a portion of $D_1$ and $D_5$ dopamine receptors. Monoclonal antibodies directed against the antigen are obtained using conventional hybridoma technology from these immunized transgenic mice. This technology is described in detail in U.S. Pat. Nos. 5,874,299; 5,877,397; 5,569,825; 5,661,016; 5,770,429; and 6,075,181, all incorporated herein by reference. As an alternative to obtaining human immunoglobulins directly from the culture of the hybridoma cells, the hybridoma cells can be used as a source of rearranged heavy chain and light chain loci for subsequent expression or genetic manipulation. Isolation of genes from such antibody-producing cells is straightforward since high levels of the appropriate mRNAs are available. The recovered rearranged loci can be manipulated as desired. For example, the constant region can be eliminated or exchanged for that of a different isotype or the variable regions can be linked to encode single chain Fv regions. Such techniques are described in WO 96/33735 and WO 96/34096, all incorporated herein by reference.

V. Selection of Test Compounds

Compounds that can be screened in accordance with the assays of the invention include but are not limited to, libraries of known compounds, including natural products, such as plant or animal extracts, synthetic chemicals, biologically active materials including proteins, peptides such as soluble peptides, including but not limited to members of random peptide libraries and combinatorial chemistry derived molecular library made of D- or L-configuration amino acids, phosphopeptides (including, but not limited to, members of random or partially degenerate, directed phosphopeptide libraries), antibodies (including, but not limited to, polyclonal, monoclonal, chimeric, human, anti-idiotypic or single chain antibodies, and Fab, $F(ab')_2$ and Fab expression library fragments, and epitope-binding fragments thereof), organic and inorganic molecules.

In addition to the more traditional sources of test compounds, computer modeling and searching technologies permit the rational selection of test compounds by utilizing structural information from the ligand binding site of dopamine receptor or from already identified agonists of dopamine receptors. Such rational selection of test compounds can decrease the number of test compounds that must be screened in order to identify a candidate therapeutic compound. Dopamine receptors are GPCRs, and thus knowledge of the dopamine receptor protein sequence allows for the generation of a model of its binding site that can be used to screen for potential ligands. This process can be accomplished in several manners well known in the art. Briefly, the most robust approach involves generating a sequence alignment of the dopamine receptor sequence to a template (derived from the bacterio-rhodopsin or rhodopsin crystal structures or other GPCR model), conversion of the amino acid structures and refining the model by molecular mechanics and visual examination. If a strong sequence alignment cannot be obtained, then a model may also be generated by building models of the hydrophobic helices. These are then fitted together by rotating and translating each helix relative to the others starting from the general layout of the known rhodopsin structures. Mutational data that point towards residue-residue contacts may also be used to position the helices relative to each other so that these contacts are achieved. During this process, docking of the known ligands into the binding site cavity within the helices may also be used to help position the helices by developing interactions that would stabilize the binding of the ligand. The model may be completed by refinement using molecular mechanics and loop building of the intracellular and extracellular loops using standard homology modeling techniques. General information regarding GPCR structure and modeling can be found in Schoneberg, T. et. al., *Molecular and Cellular Endocrinology,* 151:181–193 (1999), Flower, D., *Biochimica et Biophysica Acta,* 1422:207–234 (1999), and Sexton, P. M., *Current Opinion in Drug Discovery and Development,* 2(5):440–448 (1999).

Once the model is completed, it can be used in conjunction with one of several existing computer programs to narrow the number of compounds to be screened by the screening methods of the present invention. The most general of these is the DOCK program (UCSF Molecular Design Institute, 533 Parnassus Ave, U-64, Box 0446, San Francisco, Calif. 94143-0446). In several of its variants it can screen databases of commercial and/or proprietary compounds for steric fit and rough electrostatic complementarity to the binding site. It has frequently been found that molecules that score well within DOCK have a better chance of being ligands. Another program that can be used is FLEXX (Tripos Inc., 1699 South Hanley Rd., St. Louis, Mo., 63144-2913 (www.tripos.com)). This program, being significantly slower, is usually restricted to searches through smaller databases of compounds. The scoring scheme within FLEXX is more detailed and usually gives a better estimate of binding ability than does DOCK. FLEXX is best used to confirm DOCK suggestions, or to examine libraries of compounds that are generated combinatorially from known ligands or templates.

VI. Screening Assays to Identify Candidate Compounds for the Regulation of Skeletal Muscle Mass or Function The finding that $D_1$ and $D_5$ dopamine receptors play a role in regulating skeletal muscle atrophy hypertrophy enables various methods of screening one or more test compounds to identify candidate compounds that ultimately may be used for prophylactic or therapeutic treatment of skeletal muscle atrophy. This invention provides methods for screening test compounds for their ability to bind to $D_1$ and $D_5$ dopamine receptors, activate $D_1$ and $D_5$ dopamine receptors, prolong or augment the agonist-induced activation of $D_1$ and $D_5$ dopamine receptors or of a $D_1$ and $D_5$ dopamine receptor signal transduction pathway or increase expression of $D_1$ and $D_5$ dopamine receptor genes.

For screening for compounds which ultimately will be used to regulate skeletal muscle mass or function through $D_1$ or $D_5$ dopamine receptors in humans, it is preferred that the initial in vitro screen be carried out using a $D_1$ dopamine receptor with an amino acid sequence that is greater than 70% identical to SEQ ID NO:2 and more preferably greater than 80% identical to SEQ ID NO:2 and most preferably greater than 90% identical to SEQ ID NO:2. It is preferred that the initial in vitro screen be carried out using a $D_5$ dopamine receptor with an amino acid sequence that is greater than 70% identical to SEQ ID NO:8 and more preferably greater than 80% identical to SEQ ID NO:8 and most preferably greater than 90% identical to SEQ ID NO:8. More preferably, the test compounds will be screened against human, mouse or rat dopamine receptors, with the most preferable being human. For screening for compounds which ultimately will be used to regulate skeletal muscle mass or function through $D_1$ and $D_5$ dopamine receptors in a non-human species it is preferable to use the $D_1$ and $D_5$ dopamine receptors from the species in which treatment is contemplated.

For screening, to determine the level of activity that a test or candidate compound has towards determining what, if any, selectivity a candidate compound exhibits for $D_1$ and $D_5$ dopamine receptors, it is preferred that the initial screen be carried out using a $D_1$ dopamine receptor with an amino acid sequence that is greater than 70% identical to SEQ ID NO:2 and more preferably greater than 80% identical to SEQ ID NO:2 and most preferably greater than 90% identical to SEQ ID NO:2. It is also preferred that the next initial screen be carried out using a $D_5$ dopamine receptor with an amino acid sequence that is greater than 70% identical to SEQ ID NO:8 and more preferably greater than 80% identical to SEQ ID NO:8 and most preferably greater than 90% identical to SEQ ID NO:8. More preferably the test compounds will be screened against a human, mouse or rat, with the most preferable being human. For screening for compounds which ultimately will be used to regulate skeletal muscle mass or function in a non-human species, it is preferable to use receptors from the species in which treatment is contemplated such as those listed in Table I as SEQ ID NO: 16 through SEQ ID NO:30.

The methods of the present invention are amenable to high throughput applications; however, the use of as few as one test compound in the method is encompassed by the term "screening". Test compounds which bind to $D_1$ or $D_5$ dopamine receptors, activate $D_1$ or $D_5$ dopamine receptors, prolong or augment the agonist-induced activation of $D_1$ or $D_5$ dopamine receptors or of a $D_1$ or $D_5$ dopamine receptor signal transduction pathway, or increase expression of $D_1$ or $D_5$ dopamine receptors as determined by a method of the present invention, are referred to herein as "candidate compounds." Such candidate compounds can be used to regulate skeletal muscle mass or function. However, more typically, this first level of in vitro screen provides a means by which to select a narrower range of compounds, i.e., the candidate compounds, which merit further investigation in additional levels of screening. The skilled artisan will recognize that a utility of the present invention is to identify, from a group of one or more test compounds, a subset of compounds which merit further investigation. One of skill in the art will also recognize that the assays of the present invention are useful in ranking the probable usefulness of a particular candidate compound relative to other candidate compounds. For instance, a candidate compound which activates $D_1$ or $D_5$ dopamine receptors at 1000 nM (but not at 10 nM) is of less interest than one which activates $D_1$ or $D_5$ dopamine receptors at 10 nM. Using such information the skilled artisan may select a subset of the candidate compounds, identified in the first level of screening, for further investigation. The skilled artisan will also recognize that, depending on how the group of test compounds is selected, and how the positives are selected, only a certain proportion of test compounds will be identified as candidate compounds, and that this proportion may be very small.

The assay systems described below may be formulated into kits comprising $D_1$ or $D_5$ dopamine receptors or cells expressing the $D_1$ or $D_5$ dopamine receptors which can be packaged in a variety of containers, e.g., vials, tubes microtitre well plates, bottles and the like. Other reagents can be included in separate containers and provided with the kit, e.g., positive control samples, negative control samples, buffers and cell culture media.

In one embodiment, the invention provides a method for screening one or more test compounds to identify candidate compounds that bind to either $D_1$ or $D_5$ dopamine receptors or both. Methods of determining binding of a compound to a receptor are well known in the art. Typically, the assays include the steps of incubating a source of the $D_1$ and $D_5$ dopamine receptors with a labeled compound, known to bind to the receptor, in the presence or absence of a test compound and determining the amount of bound labeled compound. The source of $D_1$ and $D_5$ dopamine receptors may either be cells expressing $D_1$ and $D_5$ dopamine receptors or some form of isolated $D_1$ and $D_5$ doparnine receptors, as described herein. The labeled compound can be dopamine or any dopamine analog (preferably a $D_1$ and $D_5$ dopamine receptor ligand including but not limited to SCH 23390) labeled such that it can be measured, preferably quantitatively (e.g., $^{125}$I-labeled, 3H-labeled, 14C-labeled, europium labeled, fluorescein labeled). Such methods of labeling are well known in the art. Test compounds that bind to the dopamine receptor cause a reduction in the amount of labeled ligand bound to the receptor, thereby reducing the signal level compared to that from control samples (absence of test compound). Variations of this technique have been described in which receptor binding in the presence and absence of G-protein uncoupling agents can discriminate agonists from antagonists (e.g., binding in the absence and presence of a guanine nucleotide analog i.e., GpppNHp). See Keen, M., *Radioligand Binding Methods for Membrane Preparations and Intact cells* in *Receptor Signal Transduction Protocols*, R. A. J. Challis, (ed), Humana Press Inc., Totoway N.J. (1997).

Because it is desirable to discriminate between compounds which bind specifically to $D_1$ and $D_5$ dopamine receptors, as compared with, the assays described above should be conducted using a cell, or membrane from a cell, which expresses only $D_1$ and $D_5$ dopamine receptors or the assays can be conducted with a recombinant source of $D_1$ and $D_5$ dopamine receptors. Cells expressing both forms of dopamine receptor may be modified using homologous recombination to inactivate or otherwise disable one of the dopamine receptor genes. Alternatively, if the source of dopamine receptor contains more than one dopamine receptor type, the background signal produced by the receptor, which is not of interest, must be subtracted from the signal obtained in the assay. The background response can be determined by a number of methods, including elimination of the signal from the dopamine receptor, which is not of interest, by use of antisense, antibodies or selective antagonists. Known antagonists of dopamine receptors include SCH23390 ($D_1$ and $D_5$ dopamine receptors selective), and Spiperone ($D_{2/3/4}$ dopamine receptors selective).

In another embodiment, the invention provides methods for screening test compounds to identify candidate compounds which activate $D_1$ and $D_5$ dopamine receptors. This could be used in conjunction with the binding assays described herein above. Typically, the assays are cell-based; however, cell-free assays are known which are able to differentiate agonist and antagonist binding as described above. Cell-based assays include the steps of contacting cells which express $D_1$ and $D_5$ dopamine receptors with a test compound or control and measuring activation of the dopamine receptor by measuring the expression or activity of components of the dopamine receptor signal transduction pathways.

As described in the background section above, dopamine receptors appear to couple through several different pathways including $G_{\alpha q}$ or $G_{\alpha i}$, depending upon the cell type. It is thought that agonist activation of dopamine receptor allows the receptor to signal via any of these pathways, provided that the necessary pathway components are present in the particular cell type. Thus, to screen for dopamine receptor activation, an assay can use any of the signal transduction pathways as the readout even if the relevant cell type for treatment, in vivo, couples dopamine receptor to skeletal muscle atrophy via a different pathway. One of ordinary skill in the art would recognize that a screening assay would be effective for identifying useful dopamine receptor agonists independent of the pathway by which receptor activation was measured. Assays for measuring activation of these signaling pathways are known in the art.

For example, after contact with the test compound, lysates of the cells can be prepared and assayed for induction of cAMP. cAMP is induced in response to $G_{\alpha s}$ activation. Because $G_{\alpha s}$ is activated by receptors other than dopamine receptor and because a test compound may be exerting its effect through dopamine receptors or by another mechanism, two control comparisons are relevant for determining whether a text compound increases levels of cAMP via activation of a dopamine receptor. One control compares the cAMP level of cells contacted with a test compound and the cAMP level of cells contacted with a control compound (i.e., the vehicle in which the test compound is dissolved). If the test compound increases cAMP levels relative to the control compound this indicates that the test compound is increasing cAMP by some mechanism. The other control compares the cAMP levels of a dopamine receptor expressing cell line and a cell line that is essentially the same except that it does not express the dopamine receptor, where both of the cell lines have been treated with test compound. If the test compound elevates cAMP levels in the dopamine receptor expressing cell line relative to the cell line that does not express dopamine receptors, this is an indication that the test compound elevates cAMP via activation of the dopamine receptors.

In a specific embodiment of the invention, cAMP induction is measured with the use of DNA constructs containing the cAMP responsive element linked to any of a variety of reporter genes can be introduced into cells expressing dopamine receptors. Such reporter genes include, but are not limited to, chloramphenicol acetyltransferase (CAT), luciferase, glucuronide synthetase, growth hormone, fluorescent proteins (e.g., Green Fluorescent Protein), or alkaline phosphatase. Following exposure of the cells to the test compound, the level of reporter gene expression can be quantitated to determine the test compound's ability to increase cAMP levels and thus determine a test compounds ability to activate the dopamine receptor.

The cells useful in this assay are the same as for the dopamine receptor binding assay described above, except that cells utilized in the activation assays preferably express a functional receptor which gives a statistically significant response to dopamine or one or more dopamine analogs. In addition to using cells expressing full length dopamine receptors, cells can be engineered which express dopamine receptors containing the ligand binding domain of the receptor coupled to, or physically modified to contain, reporter elements or to interact with signaling proteins. For example, a wild-type dopamine receptor or dopamine receptor fragment can be fused to a G-protein resulting in activation of the fused G-protein upon agonist binding to the dopamine receptor portion of the fusion protein. (Siefert, R. et al., *Trends Pharmacol. Sci.* 20: 383–389 (1999)). The cells should also preferably possess a number of characteristics, depending on the readout, to maximize the inductive response by dopamine receptor or the dopamine receptor analog, for example, for detecting a strong induction of a CRE reporter gene; (a) a low natural level of cAMP; (b) G proteins capable of interacting with dopamine receptors; (c) a high level of adenylyl cyclase; (d) a high level of protein kinase A; (e) a low level of phosphodiesterases; and (f) a high level of cAMP response element binding protein would be advantageous. To increase the response to dopamine or a dopamine analog, host cells could be engineered to express a greater amount of favorable factors or a lesser amount of unfavorable factors. In addition, alternative pathways for induction of the CRE reporter could be eliminated to reduce basal levels.

In some instances, G protein-coupled receptor responses subside, or become desensitized, after prolonged exposure to an agonist. Another embodiment of the invention provides methods for identifying compounds that prolong or augment the agonist-induced activation of $D_1$ and $D_5$ dopamine receptors, or the $D_1$ and $D_5$ dopamine receptors signal transduction pathway, in response to a $D_1$ or $D_5$ dopamine receptors agonist. Such compounds may be used, for example, in conjunction with a $D_1$ or $D_5$ dopamine receptor agonist for the treatment of skeletal muscle atrophy. Typically the method uses a cell based assay comprising in any order or concurrently (i) contacting the cells with a test compound; (ii) treating cells expressing functional $D_1$ and $D_5$ dopamine receptors with $D_1$ and $D_5$ dopamine receptor agonists at a concentration of agonist and for a period of agonist-receptor exposure sufficient to allow desensitization of the receptor; followed by (iii) determining the level of activation of the $D_1$ and $D_5$ dopamine receptors. One of skill in the art will recognize that several mechanisms contribute to receptor desensitization including, but not limited to, receptor phosphorylation, receptor internalization or degradation and dopamine receptor signal transduction pathway down-modulation. One of skill in the art can determine the appropriate time (i.e., before, during or after agonist treatment) for contacting the cells with the test compounds depending upon which mechanism of desensitization is targeted. For example, contacting the cells with test compounds following agonist treatment, can detect test compounds which block receptor desensitization which occurs as a result of phosphorylation of the receptor.

In another embodiment, the invention provides a method of screening one or more test compound to identify candidate compounds which regulate transcription from the $D_1$ and $D_5$ dopamine receptor gene or regulate $D_1$ and $D_5$ dopamine receptor expression. Candidate compounds which regulate transcriptional activity of dopamine receptor genes may be identified using a reporter gene operably associated with $D_1$ and $D_5$ dopamine receptor regulatory region (reporter gene construct). Such methods are known in the art. In one such method, the reporter gene construct is contacted with a test compound in the presence of a source of cellular factors and the level of reporter gene expression is determined. A test compound which causes an increase in the level of expression, compared to a control sample, is indicative of a candidate compound which increases transcription of the $D_1$ and $D_5$ dopamine receptor genes. To provide the cellular factors required for in vitro or in vivo transcription, appropriate cells or cell extracts are prepared from any cell type that normally expresses $D_1$ and $D_5$ dopamine receptors.

Candidate compounds which regulate $D_1$ and $D_5$ dopamine receptor expression can also be identified in a method wherein a cell is contacted with a test compound and the expression of dopamine receptor is determined. The level of expression of $D_1$ and $D_5$ dopamine receptors in the presence of the test compound is compared with the level of expression in the absence of the test compound. Test compounds which increase the expression of $D_1$ and $D_5$ dopamine receptors are identified as candidate compounds for increasing muscle mass or muscle function. Such a method detects candidate compounds which increase the transcription or translation of the $D_1$ and $D_5$ dopamine receptors or which increase the stability of the mRNA or $D_1$ and $D_5$ dopamine receptor protein.

VII. Screening of Candidate Compounds Using Models of Skeletal Muscle Atrophy Candidate compounds selected from one or more test compounds by an in vitro assay, as described above, can be further tested for their ability to regulate skeletal muscle mass or function in model systems of skeletal muscle atrophy and/or hypertrophy. Such models of skeletal muscle atrophy or hypertrophy include both in vitro cell culture models and in vivo animal models of skeletal muscle atrophy. Such additional levels of screening are useful to further narrow the range of candidate compounds that merit additional investigation, e.g., clinical trials.

Cell Culture Models of Muscle Atrophy

In vitro models of skeletal muscle atrophy are known in the art. Such models are described, for example, in Vandenburgh, H. H., *In Vitro* 24:609–619 (1988), Vandenburgh, H. H. et al., *J of Biomechanics,* 24 Suppl 1:91–99 (1991), Vandenburgh, H. H et al., *In Vitro Cell. Dev. Biol.,* 24(3): 166–174 (1988), Chromiak, J. A., et al., *In Vitro Cell. Dev. Biol. Anim.,* 34(9):694–703 (1998), Shansky, J., et al., *In Vitro Cell. Dev. Biol. Anim.,* 33(9):659–661 (1997), Perrone, C. E. et al., *J. Biol. Chem.* 270(5):2099–2106 (1995), Chromiac, J. A. and Vandenburgh, H. H., *J. Cell. Physiol.* 159(3):407–414 (1994), and Vandenburgh, H. H. and Karlisch, P., *In Vitro Cell. Dev. Biol.* 25(7):607–616 (1989). Such models are useful, but not required; following the in vitro screening described above in order to further narrow the range of candidate compounds that merit testing in an animal model. Cell culture models are treated with candidate compounds and the response of the model to the treatment is measured by assessing changes in muscle markers such as: muscle protein synthesis or degradation, changes in skeletal muscle mass or contractile function. Those compounds which induce significant changes in the muscle markers are typically screened further in an animal model of skeletal muscle atrophy.

Animal Models of Skeletal Muscle Atrophy

The candidate compounds are administered to non-human animals and the response of the animals is monitored, for example, by assessing changes in markers of atrophy or hypertrophy such as: skeletal muscle mass, skeletal muscle function, muscle or myofiber cross-sectional area, contractile protein content, non-contractile protein content or a biochemical or genetic marker that correlates with skeletal muscle mass or function changes. Candidate compounds which induce skeletal muscle hypertrophy or prevent any aspect of skeletal muscle atrophy should be considered as prospective therapeutic candidates for treatment of human skeletal muscle atrophy, and are referred to herein as candidate therapeutic compounds. In addition to assessing the ability of a candidate compound to regulate skeletal muscle atrophy, undesirable side effects such as toxicity may also be detected in such a screen. The absence of unacceptably high levels of side effects may be used as a further criterion for the selection of candidate therapeutic compounds.

A variety of animal models for skeletal muscle atrophy are known in the art, such as those described in the following references: Herbison, G. J., et al. *Arch. Phys. Med. Rehabil.* 60:401–404 (1979), Appell, H-J. *Sports Medicine* 10:42–58 (1990), Hasselgren, P-O. and Fischer, J. E. *World J. Surg.* 22:203–208 (1998), Agbenyega, E. T. and Wareham, A. C. *Comp. Biochem. Physiol.* 102A:141–145 (1992), Thomason, D. B. and Booth, F. W. *J. Appl. Physiol.* 68:1–12 (1990), Fitts, R. H., et al. *J. Appl. Physiol.* 60:1946–1953 (1986), Bramanti, P., et al. *Int. J. Anat. Embryol.* 103:45–64 (1998), Cartee, G. D. *J. Gerontol. A Biol. Sci. Med. Sci.* 50:137–141 (1995), Cork, L. C., et al. *Prog. Clin. Biol. Res.* 229:241–269 (1987), Booth, F. W. and Gollnick, P. D. *Med. Sci. Sports Exerc.* 15:415–420 (1983), Bloomfield, S. A. *Med. Sci. Sports Exerc.* 29:197–206 (1997). Preferred animals for these models are mice and rats. These models include, for example, models of disuse-induced atrophy such as casting or otherwise immobilizing limbs, hind limb suspension, complete animal immobilization, and reduced gravity situations. Models of nerve damage induced atrophy include, for example, nerve crush, removal of sections of nerves which innervate specific muscles, toxin application to nerves and infection of nerves with viral, bacterial or eukaryotic infectious agents. Models of glucocorticoid-induced atrophy include application of atrophy-inducing doses of exogenous glucocorticoid to animals, and stimulation of endogenous corticosteroid production, for example, by application of hormones that activate the hypothalamus-pituitary-adrenal (HPA) axis. Models of sepsis-induced atrophy include, for example, inoculation with sepsis-inducing organisms such as bacteria, treatment of the animal with immune-activating compounds such as bacterial cell wall extract or endotoxin, and puncture of intestinal walls. Models of cachexia-induced atrophy include, for example, inoculation of an animal with tumorigenic cells with cachexia forming potential, infection of an animal with infectious agents (such as viruses which cause AIDS) which result in cachexia and treatment of an animal with hormones or cytokines such as CNTF, TNF, IL-6, IL-1, etc. which induce cachexia. Models of heart failure-induced atrophy include the manipulation of an animal so that heart failure occurs with concomitant skeletal muscle atrophy. Neurodegenerative disease-induced atrophy models include autoimmune animal models such as those resulting from immunization of an animal with neuronal components. Muscular dystrophy-induced models of atrophy include natural or man-made genetically-induced models of muscular dystrophy such as the mutation of the dystrophin gene which occurs in the Mdx mouse.

Animal models of skeletal muscle hypertrophy include, for example, models of increased limb muscle use due to inactivation of the opposing limb, reweighting following a disuse atrophy inducing event, reutilization of a muscle which atrophied because of transient nerve damage, increased use of selective muscles due to inactivation of a synergistic muscle (e.g., compensatory hypertrophy), increased muscle utilization due to increased load placed on the muscle and hypertrophy resulting from removal of the glucocorticoid after glucocorticoid-induced atrophy. Preferred animal atrophy models include the sciatic nerve denervation atrophy model, glucocorticoid-induced atrophy model, and the leg casting disuse atrophy model that are described in further detail below.

The sciatic nerve denervation atrophy model involves anesthetizing the animal followed by the surgical removal of a short segment of either the right or left sciatic nerve, e.g., in mice the sciatic nerve is isolated approximately at the midpoint along the femur and a 3–5 mm segment is removed. This denervates the lower hind limb musculature resulting in atrophy of these muscles. Typically, innervation to the biceps femoris is left intact to provide satisfactory motion of the knee for virtually normal ambulation. Typically, in untreated animals, muscle mass of the denervated muscles is reduced 30–50% ten days following denervation. Following denervation, test compounds are administered e.g., by injection or by continuous infusion, e.g., via implantation of an osmotic minipump (e.g., Alzet, Palo Alto, Calif.), to determine their effect on denervation induced skeletal muscle atrophy. At various times following denervation, the animals are euthanized and lower leg muscles are dissected rapidly from both the denervated and nondenervated legs, the muscles, cleaned of tendons and connective tissue, are weighed. The extent of atrophy in the affected muscles is analyzed, for example, by measuring muscle mass, muscle cross-sectional area, myofiber cross-sectional area or contractile protein content.

The glucocorticoid-induced atrophy model involves the administration of a glucocorticoid to the test animal, e.g., 1.2 mg/kg/day of dexamethasone in the drinking water. Typically, in untreated animals, skeletal muscle mass is reduced 30–50% following ten days of dexamethasone administration. Concomitantly with, or following glucocorticoid administration, test compounds are administered e.g., by injection or by continuous infusion to determine their effect on glucocorticoid-induced skeletal muscle atrophy. At various times following glucocorticoid administration, the extent of atrophy in the affected muscles is analyzed as described above for the denervation model.

The leg casting disuse atrophy model involves casting one hind leg of an animal from the knee down through the foot. Typically, muscle mass is reduced 20–40% after ten days of casting. Following casting, test compounds are administered by injection or by continuous infusion via implantation of an osmotic minipump (e.g., Alzet, Palo Alto, Calif.) to determine their effect on leg casting induced skeletal muscle atrophy. At various times following leg casting, the extent of atrophy in the affected muscles is analyzed as described above for the denervation model.

One of skill in the art would recognize that in screening for compounds for human use, because there are differences between the human $D_1$ and $D_5$ dopamine receptors and the $D_1$ and $D_5$ dopamine receptors from other animal species, there may be some false positive or negative results which arise when the screen is carried out using non-human $D_1$ and $D_5$ dopamine receptors. Thus, it is preferable to do the initial in vitro screen using human $D_1$ and $D_5$ dopamine receptors. In certain circumstances, identified candidate compounds may be active toward only the human receptor and not toward a non-human receptor. In such circumstances, it may still be desirable to determine whether these candidate compounds are able to regulate skeletal muscle mass or function in a second level of screening. Because these candidates do not activate non-human $D_1$ and $D_5$ dopamine receptors, a standard in vivo screen with non-human animal is not advised. In such circumstances the second level of screening for these candidates may be performed in transgenic animals that express human dopamine receptors.

Animals of any species, especially mammals, including, but not limited to, mice, rats, rabbits, guinea pigs, pigs, goats, dogs and non-human primates may be used to generate dopamine receptor transgenic animals. Mice and rats are preferred, mice are most preferred. A variety of techniques are known in the art and may be used to introduce the human dopamine receptor transgenes into animals to produce the founder lines of transgenic animals. Such techniques include, but are not limited to, pronuclear microinjection, retrovirus-mediated gene transfer into germ lines, gene targeting in embryonic stem cells, electroporation of embryos and sperm-mediated gene transfer.

VIII. Gene Therapy Methods for the Treatment of Skeletal Muscle Atrophy

The overall activity of $D_1$ and $D_5$ dopamine receptors can be increased by overexpressing a gene for $D_1$ and $D_5$ dopamine receptors (to increase expression of $D_1$ and $D_5$ dopamine receptors) or a constitutively active $D_1$ and $D_5$ dopamine receptors in the appropriate tissue. Dopamine receptor levels can be increased, in vivo, by likewise overexpressing a dopamine receptor gene. Overexpression of these genes will increase the total cellular $D_1$ and $D_5$ dopamine receptor activity, thus, regulating skeletal muscle atrophy. The gene or genes of interest are inserted into a vector suitable for expression in the subject. These vectors include, but are not limited to, adenovirus, adenovirus associated virus, retrovirus and herpes virus vectors in addition to other particles that introduced DNA into cells (e.g., liposome, gold particles, etc.) or by direct injection of the DNA expression vector, containing the gene of interest, into human tissue (e.g., muscle).

IX. Pharmaceutical Formulations and Methods for Use

Candidate compounds or candidate therapeutic compounds identified by screening methods described herein can be administered to individuals to treat skeletal muscle atrophy, or to induce skeletal muscle hypertrophy. To this end, the present invention encompasses methods and compositions for modulating skeletal muscle atrophy, including, but not limited to, skeletal muscle atrophy induced by disuse due to surgery, bed rest, broken bones; denervation/nerve damage due to spinal cord injury; autoimmune disease; infectious disease; glucocorticoid use for unrelated conditions; sepsis due to infection or other causes; nutrient limitation due to illness or starvation; cancer cachexia; chronic inflammation; AIDS cachexia; COPD; congestive heart failure; sarcopenia and genetic disorders; e.g., muscular dystrophies, neurodegenerative diseases. Agonists of $D_1$ and $D_5$ dopamine receptors can be used to inhibit skeletal muscle atrophy. It is not necessary that effective compounds demonstrate absolute specificity for dopamine receptor. It is contemplated that specific antagonist of other affected receptors can be co-administered with an effective, but nonspecific, agonist. Alternately, this lack of specificity may be addressed by modulation of dose alone, or the dosing regimen.

The candidate compounds or candidate therapeutic compounds identified by the screening methods of the present invention may be administered in conjunction with compounds which prolong or augment the activation of a $D_1$ and $D_5$ dopamine receptors or of a $D_1$ and $D_5$ dopamine receptors signal transduction pathway. These may be known compounds, for example, theophylline, or these compounds may be identified by the screening methods of this invention to prolong or augment the activation of a $D_1$ and $D_5$ dopamine receptor or of a $D_1$ and $D_5$ dopamine receptor signal transduction pathway.

Dose Determinations

Safety and therapeutic efficacy of compounds which agonize dopamine receptor can be determined by standard procedures using either in vitro or in vivo technologies. Compounds which exhibit large therapeutic indices are preferred, although compounds with lower therapeutic indices are useful if the level of side effects is acceptable. The data obtained from the in vitro and in vivo toxicological and pharmacological techniques can be used to formulate the human range of doses which may be useful. The preferred dose lies in the range in which the circulating concentration of the compound is therapeutically maximal with acceptable safety. The circulating concentration of the compound may vary depending on the dose form, time after dosing, route of administration, etc. Doses outside this range are also useful provided the side effects are acceptable. Such matters as age and weight of the patient, and the like, can be used to determine such matters in the conventional manner. Pharmacogenetic approaches may be useful in optimizing compound selection, doses and dosing regimen in clinical populations.

Formulation and Use

Pharmaceutical compositions for use in the modulation of skeletal muscle atrophy in accordance with the present invention may be formulated using conventional methodologies using pharmaceutically acceptable carriers and excipients. The compositions of this invention are preferably provided in unit dosage form. As used herein, a "unit dosage form" is a composition of this invention containing an amount of a $D_1$ and $D_5$ dopamine receptor agonist that is suitable for administration to an animal, preferably a mammal, more preferably a human subject, in a single dose, according to good medical practice. Pharmaceutical compositions may be formulated for delivery by, for example, intranasal, transdermal, inhalation, parenteral, cutaneous, oral or rectal administration. For oral administration, the pharmaceutical composition may take the form of tablets or capsules containing the pharmacologically active compound and additives including, but not limited to, binding agents, fillers, lubricants, disintegrants, or wetting agents. The tablets may be coated. Liquid preparations for oral administration include, but are not limited to, syrups, suspensions or dry products which are reconstituted with liquid vehicle before use, containing the pharmacologically active compound and additives including, but not limited to, suspending agents, emulsifying agents, non-aqueous vehicles, preservatives, buffer salts, flavoring, coloring, sweetening agents, etc. Pharmaceutical compositions for oral administration may be formulated for controlled release of the pharmacologically active compounds either in the mouth, stomach or intestinal tract.

For inhalation administration, the compounds for use according to the present invention may be delivered by, but not limited to, the following forms: liquid, powder, gel or in the form of an aerosol spray utilizing either pressurized or non-pressurized propellants in either premeasured or non-premeasured doses. The pharmacologically active compound may be formulated with appropriate fillers, vehicles, preservatives, buffers, etc. For parenteral administration, the pharmacologically active compound may be formulated with acceptable physiological carriers, preservatives, etc. and be prepared as suspensions, solutions, emulsion, powders ready for constitution, etc. for either bolus injection or infusion. Doses of these compounds may be administered by a variety of technologies including hypodermic needles, high-pressure devices, etc. For rectal administration, the pharmacologically active compound may be formulated with acceptable physiological carriers, preservatives, etc. for delivery as suppositories, enemas, etc. For cutaneous administration, the pharmacologically active compound may be formulated with acceptable physiological carriers including lotions, emollients, etc. or incorporated into a patch type device. For long-term administration, the pharmacologically active compound and appropriate additives such as, but limited to, polymers, hydrophobic materials, resins, etc. may be formulated as a depot preparation for either injection or implantation at multiple sites including but not limited to intramuscular and subcutaneous locations. In addition, the pharmacologically active compound may be administered by a dispensing device.

Monitoring of Effects During Clinical Trials

Monitoring the influence of compounds (e.g., drugs) on the expression or activity of $D_1$ and $D_5$ dopamine receptors can be employed not only in basic drug screening, but also in clinical trials. For example, the effectiveness of a compound determined by a screening assay to increase $D_1$ and $D_5$ dopamine receptor activity or $D_1$ and $D_5$ dopamine receptor expression can be assessed in clinical trials of patients with, or at risk for, skeletal muscle atrophy. At various times following administration of the test compound or placebo, the effect of the compound on the patient can be determined, for example, by observing the change in skeletal muscle mass, skeletal muscle function, biochemical markers of muscle breakdown or quality of life measures. Methods of measuring skeletal muscle mass in human subjects are known in the art and include, for example: measuring the girth of a limb; measuring muscle thickness with for instance, computer tomography, MRI or supersonics; or muscle biopsy to examine morphological and biochemical parameters (e.g., cross-section fiber area, fiber diameter or enzyme activities). Furthermore, because skeletal muscle mass is correlated with skeletal muscle function, muscle function can be used as a surrogate marker of mass and muscle mass changes can be assessed using functional measurements, e.g., strength, the force of a group of synergist muscles, or contraction characteristics found in electromyographic recordings. In addition, muscle protein loss as a result of muscle atrophy can be measured by quantitating levels of amino acids or amino acids derivatives, i.e., 3-methyl histidine, in the urine or blood of a subject. For a review of such methods see Appell, *Sports Med.* 10:42–58 (1990). Quality of life measures include, but are not limited to, the ease of getting out of a chair, number of steps taken before tiring or ability to climb stairs.

EXAMPLES

Example 1

Construction of Vectors for Human $D_1$ and $D_5$ Dopamine Receptors Expression The human $D_1$ and $D_5$ dopamine receptors ($hD_1$ and $hD_5$ dopamine receptors) DNA sequences, Accession No. X58987 and X58454, are retrieved and two oligonucleotides including one containing the 5' end of the gene beginning at the initiation codon (5' oligonucleotide) and one containing the 3' end of the gene containing the stop codon (3' oligonucleotide) are synthesized. These oligonucleotides are designed to contain restriction endonuclease sites which are not present in the $D_1$ or $D_5$ dopamine receptor gene with one unique site in the 5' oligonucleotide and a different unique restriction endonuclease site in the 3' oligonucleotide. In addition, the 3' oligonucleotide contains a polyadenylation addition signal sequence. Double stranded cDNA from human skeletal muscle is purchased from the Universal QUICK-Clone cDNA collection (Clonetech Inc., Palo Alto, Calif., USA). Using the above 5' and 3' oligonucleotides, the $D_1$ and $D_5$ dopamine receptors cDNA is amplified by PCR of the human skeletal muscle cDNA using the AdvanTaq PCR kit (Clonetech Inc., Palo Alto, Calif., USA). The $D_1$ and $D_5$ dopamine receptor gene PCR product is purified from PCR artifacts by agarose gel electrophoresis and the $D_1$ and $D_5$ dopamine receptor gene DNA fragment is purified from the agarose gel using a purification product such as NucleoTrap (Clonetech Inc., Palo Alto, Calif., USA).

Cloning of the $D_1$ and $D_5$ dopamine receptor PCR products into the pIRESneo vector (Clonetech Inc., Palo Alto, Calif., USA) is accomplished by first cutting the $D_1$ and $D_5$ dopamine receptor PCR product and the pIRESneo vector with the appropriate restriction endonucleases so that the 5' and 3' restriction endonuclease sites are ready for ligation. The pIRESneo vector DNA is ligated to the $D_1$ and $D_5$ dopamine receptor PCR products DNA using DNA ligase, from the AdvantAge™PCR Cloning Kit (Clonetech Inc., Palo Alto, Calif., USA), according to the manufacturer's recommendations. The ligated vector and insert construct (pIRESneo/$D_1$ and $D_5$ dopamine receptors)is then used to transform TOP10F' competent *E. coli* cells (Clonetech Inc., Palo Alto, Calif., USA). Transformed cells are plated on LB/X-gal/IPTG plus ampicillin containing agar. White colonies (positive clones) are selected and individually cultured in LB medium. Plasmid DNA is isolated using NucleoBond DNA Purification System (Clonetech Inc., Palo Alto, Calif., USA). The insert from at least one clone is sequenced to ensure that the $D_1$ and $D_5$ dopamine receptor sequence is correct. HEK293 cells containing a stably integrated Mercury CRE-LUC plasmid (Clonetech Inc., Palo Alto, Calif., USA) are transfected with purified pIRESneo/$D_1$ and $D_5$ dopamine receptors DNA, having the correct sequence insert, utilizing the CalPhos™ Mammalian Transfection Kit (Clonetech Inc., Palo Alto, Calif., USA. Cells stably transfected with pIRESneo/$D_1$ and $D_5$ dopamine receptors DNA are selected by culturing the cells in G418. The stably transfected cells (HEK293/CRE-LUC/pIRESneo/$D_1$ and $D_5$ dopamine receptors cells) are propagated in DMEM (Life Technologies, Rockville, Md.) containing 10% fetal bovine serum (Clonetech Inc., Palo Alto, Calif., USA), penicillin/streptomycin solution (Life Technologies, Rockville, Md.), L-glutamine (Life Technologies, Rockville, Md.), and non-essential amino acid (Life Technologies, Rockville, Md.) at 37° C. in a 5% carbon dioxide/95% air atmosphere. The clones are characterized for both dopamine receptor binding and CRE-LUC activation following exposure to dopamine receptor as described in Example 2 and Example 3. Cells expressing the $D_1$ and $D_5$ dopamine receptor at an appropriate level and which are appropriately coupled to the CRE-LUC reporter system are then utilized for further analysis.

Example 2

Receptor Binding Assays

Receptor binding analysis of compounds is performed in whole cells by plating the HEK293/CRE-LUC/pIRESneo/$D_1$ or $D_5$ dopamine receptors cells from Example 1 in a 96 well polylysine coated plate. Cells are seeded in DMEM medium containing 10% fetal bovine serum, penicillin/streptomycin solution, L-glutamine, and non-essential amino acid at 37° C. in a 5% carbon dioxide/95% air atmosphere and incubated overnight. The culture medium is removed and the appropriate amount of 3H-SCH23390 in MEM (Life Technologies, Rockville, Md.) +10% Seablock (Clonetech Inc., Palo Alto, Calif., USA) is added. The cells are incubated with the 3H-SCH23390 for 90 minutes at room temperature then washed 4 times with phosphate buffered saline lacking magnesium and calcium (Life Technologies, Rockville, Md.). Following the final wash, cytoscint es scintillation fluid is added (ICN Biomedical, Inc., Costa Mesa, Calif.) and the plate is read on a TopCount NXT Microplate Scintillation Counter (Packard Instrument Company, Meriden, Conn.). For saturation binding analysis, log doses of ranging from 10(−12) to 10(−3) M are added to the cells and binding analyzed both in the absence and the presence of a saturating concentration of SCH23390 for evaluation of non-specific binding. For competitive binding, a concentration of SCH23390 is added which is half maximal, in terms of binding, in addition to varying concentrations of the compound of interest.

Example 3

Receptor Activation Assay

Receptor activation analysis is performed by seeding the HEK293/CRE-LUC/pIRESneo/$D_1$ or $D_5$ dopamine receptors cells of Example 1 into Packard View Plate-96 (Packard Inc., CA). Cells are seeded in DMEM medium containing 10% fetal bovine serum, penicillin/streptomycin solution, L-glutamine, and non-essential amino acid at 37° C. in a 5% carbon dioxide/95% air atmosphere and incubated overnight. The medium is then removed and replaced with DMEM (Life Technologies, Rockville, Md.) containing 0.01% bovine albumin fraction V (SIGMA, St. Louis, Mo.) containing the compound of interest. The cells are then incubated for four hours at 37° C. in a 5% carbon dioxide/95% air atmosphere after which the medium is removed and the cells are washed twice with Hanks Balanced Salt Solution (Life Technologies, Rockville, Md.). Lysis Reagent (Promega Inc., Madison, Wis.) is then added to the washed cells and the cells are incubated for 20 minutes at 37° C. in a 5% carbon dioxide/95% air atmosphere. The cells are then placed at −80° C. for 20 minutes followed by a 20 minute incubation at 37° C. in a 5% carbon dioxide/95% air atmosphere. After this incubation, Luciferase Assay Buffer and Luciferase Assay Substrate (Promega Inc., Madison, Wis.) are added to the cell lysates and luciferase activity quantitated using a luminometer. Relative activity of a compound is evaluated by comparing the increase following exposure to compound to the level of luciferase in HEK cells which contain the CRE-LUC construct without the $D_1$ and $D_5$ dopamine receptors following exposure to compound. Specificity of response is also checked by evaluating luciferase response of $D_1$ and $D_5$ dopamine receptors/CRE-LUC HEK cells to compound in the presence and absence of a 10-fold excess of $D_1$ and $D_5$ dopamine receptors antagonist.

Example 4

Screen to Identify Candidate Compounds that Prolong or Augment the Activation of $D_1$ or $D_5$ Dopamine Receptors and/or a $D_1$ and $D_5$ Dopamine Receptor Signal Transduction Pathway Identification of compounds that prolong or augment the agonist-induced activation of the $D_1$ or $D_5$ dopamine receptors or of a $D_1$ and $D_5$ dopamine receptors signal transduction pathway, involves a variation of the Receptor Activation Assay described in Example 3. Specifically, this assay is performed by seeding the HEK293/CRE-LUC/pIRESneo/$D_1$ and $D_5$ dopamine receptor cells into Packard View Plate-96 (Packard Inc., CA). Cells are seeded in DMEM medium containing 10% fetal bovine serum, penicillin/streptomycin solution, L-glutamine, non-essential amino acid, and saturating amounts of dopamine receptor at 37° C. in a 5% carbon dioxide/95% air atmosphere and incubated for 48 hours. The medium is then removed and replaced with DMEM (Life Technologies, Rockville, Md.) containing 0.01% bovine albumin fraction V (SIGMA, St. Louis, Mo.) and SKF81297 in addition to the compound of interest. The cells are then incubated for four hours at 37° C. in a 5% carbon dioxide/95% air atmosphere after which the medium is removed and the cells are washed twice with Hanks Balanced Salt Solution (Life Technologies, Rockville, Md.). Lysis Reagent (Promega Inc., Madison, Wis.) is then added to the washed cells and the cells are incubated for 20 minutes at 37° C. in a 5% carbon dioxide/95% air atmosphere. The cells are then placed at −80° C. for 20 minutes followed by a 20 minute incubation at 37° C. in a 5% carbon dioxide/95% air atmosphere. After this incubation, Luciferase Assay Buffer and Luciferase Assay Substrate (Promega Inc., Madison, Wis.) are added to the cell lysates and luciferase activity is quantitated using a luminometer. Test compounds which stimulate fluorescence significantly above the levels of control untreated cells, after correction for variations in cell density, are considered candidate compounds for regulating skeletal muscle mass or function. The compounds of most interest are those that induce relatively higher levels of fluorescence.

Example 5

Screens to Identify Candidate Compounds that Increase $D_1$ or $D_5$ Dopamine Receptor Expression The sequence containing the promoter region of the $D_1$ or $D_5$ dopamine receptor genes, beginning far enough upstream of the transcriptional initiation site to contain all the regulatory elements necessary for physiological expression of the $D_1$ or $D_5$ dopamine receptor genes in the appropriate tissue is retrieved from the human genome database. Two oligonucleotides, one containing the 5' end of the promoter region (5' oligonucleotide) and one containing the 3' end of the promoter region including the transcriptional start site (3' oligonucleotide) are synthesized. These oligonucleotides also contain restriction endonuclease sites which are not present in the $D_1$ or $D_5$ dopamine receptor genes regulatory region with one unique site in the 5' oligonucleotide and a different unique restriction endonuclease site in the 3' oligonucleotide. The 5' and 3' oligonucleotides are used for PCR amplification of the $D_1$ or $D_5$ dopamine receptor genes regulatory region from human DNA (Clonetech Inc., Palo Alto, Calif., USA) using the PCR kit, Advantage®Genomic PCR kit (Clonetech Inc., Palo Alto, Calif., USA). The $D_1$ and $D_5$ dopamine receptor genes regulatory region PCR products are purified from PCR artifacts by agarose gel electrophoresis and the $D_1$ and $D_5$ dopamine receptor genes regulatory region DNA fragment is purified from the agarose gel using a purification product such as NucleoTrap (Clonetech Inc., Palo Alto, Calif., USA). Cloning of the $D_1$ and $D_5$ dopamine receptor genes regulatory region PCR products into the pECFP-1 vector (Clonetech Inc., Palo Alto, Calif., USA) is accomplished by first cutting the $D_1$ and $D_5$ dopamine receptor genes regulatory region PCR products and the pECFP-1 vector with the appropriate restriction endonucleases so that the 5' and 3' restriction endonuclease sites are ready for ligation. Ligation of the pECFP-1 vector DNA to the $D_1$ and $D_5$ dopamine receptor genes regulatory region PCR products DNA are accomplished using DNA ligase from the AdvantAge™PCR Cloning Kit (Clonetech Inc., Palo Alto, Calif., USA) according to the manufacturer's recommendations. The ligated vector and insert construct is then used to transform TOP10F' competent *E. coli* cells (Clonetech Inc., Palo Alto, Calif., USA). The cells are plated on LB plus kanamycin containing agar and kanamycin resistant colonies are selected for further analysis. Kanamycin resistant clones are cultured in LB containing kanamycin medium and plasmid DNA is isolated using NucleoBond DNA Purification System (Clonetech Inc., Palo Alto, Calif., USA) and the construct containing the $D_1$ and $D_5$ dopamine receptor genes regulatory region is analyzed by DNA sequencing to ensure construct correctness and integrity. Purified construct plasmid DNA containing the $D_1$ and $D_5$ dopamine receptor genes regulatory region is then transfected into the BEK293 cells utilizing calcium phosphate-mediated transfection utilizing the CalPhos™ Mammalian Transfection Kit (Clonetech Inc., Palo Alto, Calif., USA). Transfected cell clones are selected using G418, isolated and propagated in DMEM (Life Technologies, Rockville, Md.) containing 10% fetal bovine serum (Clonetech Inc., Palo Alto, Calif., USA), penicillin/streptomycin solution (Life Technologies, Rockville, Md.), L-glutamine (Life Technologies, Rockville, Md.), non-essential amino acid (Life Technologies, Rockville, Md.) and G418 (Life Technologies, Rockville, Md.) at 37° C. in a 5% carbon dioxide/95% air atmosphere. G418 resistant clones are characterized by Southern blotting to ensure that they contain the $D_1$ and $D_5$ dopamine receptor genes promoter sequence; in addition activation of the $D_1$ and $D_5$ dopamine receptor genes regulatory region is analyzed using an appropriate stimulating agent. Cells expressing the $D_1$ and $D_5$ dopamine receptor genes regulatory region-ECFP at an appropriate level are then used in assays designed to evaluate compounds which can modulate the activity of the $D_1$ and $D_5$ dopamine receptor genes regulatory region as follows. The regulatory region activation analysis is performed by seeding the $D_1$ and $D_5$ dopamine receptor genes regulatory region-ECFP containing HEK293 cells at an appropriate density into black with clear bottom 96 well microtiter plates and allowed to grow overnight. The following day, the medium is removed and the test compound added in fresh growth medium. The cells are incubated for 16 hours at 37° C. in a 5% carbon dioxide/95% air atmosphere followed by measurement of fluorescence (excitation at 433 (453) nm by detecting emission at 475(501) nm using a fluorometer (biolumin™ 960, Molecular Dynamics/Amersham Pharmacia Biotech, Piscataway, N.J.). Test compounds which stimulate fluorescence significantly above the levels of control untreated cells, after correction for variations in cell density, are considered candidate compounds for regulating skeletal muscle mass or function. The compounds of most interest are those which induce relatively higher levels of fluorescence.

Example 6

Method of Making Human Antibodies which Activate the $D_1$ and $D_5$ Dopamine Receptors Fully human monoclonal antibodies which activate the $D_1$ and $D_5$ dopamine receptors are produced by first generating recombinant $D_1$ and $D_5$ dopamine receptor proteins as follows. The procedure from Example 1 is followed to obtain the $D_1$ and $D_5$ dopamine receptors PCR product. This $D_1$ and $D_5$ dopamine receptors PCR product is then cloned into the pHAT20 vector (Clonetech Inc., Palo Alto, Calif., USA) by first cutting the $D_1$ and $D_5$ dopamine receptor gene PCR product and the pHAT20 vector with the appropriate restriction endonucleases so that the 5' and 3' restriction endonuclease sites are ready for ligation. Ligation of the pHAT20 vector DNA to the $D_1$ and $D_5$ dopamine receptor genes PCR product DNA is accomplished using DNA ligase from the AdvantAge™PCR Cloning Kit (Clonetech Inc., Palo Alto, Calif., USA) according to the manufacturer's recommendations. The ligated vector/insert construct is then used to transform TOP10F' competent *E. coli* cells (Clonetech Inc., Palo Alto, Calif., USA). Transformed cells are plated on LB plus ampicillin containing agar and ampicillin resistant colonies are selected for further analysis. Positive clones are cultured in LB medium containing ampicillin and plasmid DNA is isolated using NucleoBond DNA Purification System (Clonetech Inc., Palo Alto, Calif., USA) and the construct containing the $D_1$ and $D_5$ dopamine receptor genes is analyzed by DNA sequencing the ensure construct correctness and integrity. The $D_1$ and $D_5$ dopamine receptors-pHAT20 vector DNA is then used for additional PCR cloning by utilizing a 5' oligonucleotide containing the beginning of the HAT sequence and a unique restriction endonuclease site not present in the $D_1$ and $D_5$ dopamine receptors-pHAT20 construct and the 3' $D_1$ and $D_5$ dopamine receptors oligonucleotide utilized previously. The oligonucleotide primers are used to PCR amplify the HAT-$D_1$ and $D_5$ dopamine receptors fusion gene from the $D_1$ and $D_5$ dopamine receptors-pHAT20 construct and the PCR product is purified as described above. The HAT-$D_1$ and $D_5$ dopamine receptors fusion gene PCR product is then utilized for cloning into the pBacPAK8 vector using the BacPAK Baculovirus Expression System from Clonetech (Clonetech Inc., Palo Alto, Calif., USA). The ligation of the HAT-$D_1$ and $D_5$ dopamine receptors fusion gene into the pBacPAK8 vector is essentially as described above. The $D_1$ and $D_5$ dopamine receptors/HAT-pBacPAK8 construct is then transfected into TOP10'F competent *E. coli* cells, ampicillin resistant cells are selected and plasmid DNA is isolated and checked for construct integrity as described above. This construct is then cotransfected with linearized BacPAK6 DNA into Sf21 insect host cells utilizing the CalPhos™ Mammalian Transfection Kit (Clonetech Inc., Palo Alto, Calif., USA). The insect cells are then incubated for 2–3 days followed by harvest of virus from individual clear plaques. The virus is then amplified in Sf21 cells, the harvested virus titered, and the titered virus used for large scale infection of Sf21 cells utilizing BacPAK Insect Cell Media—all according to the manufacturers recommendations (Clonetech Inc., Palo Alto, Calif., USA). Recombinant HAT-$D_1$ and $D_5$ dopamine receptor fusion proteins are then purified using the TALON® CellThru Purification Kit from Clonetech (Clonetech Inc., Palo Alto, Calif., USA) using conditions recommended by the manufacturer. Briefly, infected Sf21 cells are harvested 48 hours after infection and sonicated in extraction/loading buffer. The cell lysate is then put through a TALON® CellThru column. The column is washed twice with extraction/loading buffer and the bound HAT-$D_1$ and $D_5$ dopamine receptor proteins are eluted with elution buffer. The eluted protein is analyzed by SDS-PAGE for integrity and protein concentration is quantitated using the Bio-Rad SDS-PAGE system and protein quantitation systems according to the manufacturer's recommendations (Bio-Rad Laboratories, Hercules, Calif.). Purified HAT-$D_1$ and $D_5$ dopamine receptor fusion proteins are then used for immunizing XenoMouse animals (Abgenix Inc., Fremont, Calif.) for human monoclonal antibody production as follows. 10 μg of purified recombinant HAT-$D_1$ and $D_5$ dopamine receptor fusion proteins in combination with 25 μg of adjuvant monophosphoryl lipid A (Sigma, St. Louis, Mo.) is used to vaccinate 10 XenoMouse animals multiple times over an eight week period. Serum is obtained from vaccinated animals and utilized in an antigen capture ELISA utilizing purified HAT-$D_1$ and $D_5$ dopamine receptor fusion proteins to detect antibodies to the HAT-$D_1$ and $D_5$ dopamine receptor proteins by coating polystyrene ELISA plates (Corning Glass Works, Corning, N.Y.) with HAT-$D_1$ and $D_5$ dopamine receptor fusion proteins, blocked with PBS-1% BSA, washed and incubated at 37° C. for 1 hour with a 1:50 dilution of the serum samples. After washing 5 times with PBS, the plates are incubated at 37° C. for 1 hour with alkaline phosphatase-conjugated goat antibodies to human immunoglobulin G. The plates are then washed 5× with PBS and antibodies detected with p-nitrophenyl phosphate substrate (Sigma, St. Louis, Mo.) in buffer. Optical densities at 405 nm were measured using a plate reader and signal quantitated. Mice with demonstrated high antibody production are used for hybridoma formation. Hybridomas are generated by fusion of splenic cells from the XenoMouse animals with nonsecreting myeloma cell line NSA-bcd 2 using a 4:1 ratio of spleen cells to NSA-bcl2 cells in the presence of 30% polyethylene glycol PEG1450. Fused cells are individually cloned by limiting dilution into 96 well plates and cultured in RPMI-1640 medium containing 10% fetal bovine serum, nonessential amino acids, sodium pyruvate, L-glutamine, 100 μ/ml penicillin-streptomycin and hypoxanthine-aminopterin-thymidine (all from Life Technologies, Rockville, Md.). Supernatants from the hypoxanthine-aminopterin-thymidine selected hybridomas were screened for human antibody production by ELISA as described previously. Hybridomas which produce human antibodies to the HAT-$D_1$ and $D_5$ dopamine receptors fusion protein are selected for large scale antibody production. Monoclonal antibodies are purified by Protein G-Sepharose chromatography. Briefly, the supernatant from cultured hybridoma clones is loaded onto a Protein G-Sepharose column (SIGMA, St. Louis, Mo.) in loading buffer, washed 3 times and the IgG is eluted with elution buffer. These antibodies are then used for screening to evaluate $D_1$ and $D_5$ dopamine receptors activation (agonism) potential. This is accomplished using the methodology as outlined in Example 3. Those human monoclonal antibodies which demonstrate agonist activity toward the $D_1$ and $D_5$ dopamine receptors are designated candidate compounds.

Example 7

Determination of Absolute Force Measurement of a Muscle

The extensor digitorum longus (EDL) and soleus muscles are removed, tendon-to-tendon from the casted mouse leg. A silk suture is tied to each tendon of the isolated muscles and the muscles are placed into a plexiglass chamber filled with Ringer solution (137 mM sodium chloride, 24 mM sodium bicarbonate, 11 mM glucose, 5 mM potassium chloride, 1 mM magnesium sulfate, 1 mM sodium phosphate, 0.025 mM tubocurarine, all at pH 7.4 and oxygenated with 95% oxygen/5% carbon dioxide) constantly bubbled with 95% oxygen/5% carbon dioxide maintained at 25° C. Muscles are aligned horizontally between a servomotor lever arm (Model 305B-LR Cambridge Technology Inc., Watertown Mass., USA) and the stainless steel hook of a force transducer (Model BG-50; Kulite Semiconductor Products Inc., Leonia, N.J., USA) and field stimulated by pulses transmitted between two platinum electrodes placed longitudinally on either side of the muscle. Square wave pulses (0.2 ms duration) generated by a personal computer with a Labview board (Model PCI-MIO 16E-4), Labview Inc., Austin, Tex., USA) are amplified (Acurus power amplifier model A25, Dobbs Ferry, N.Y., USA) to increase titanic contraction. Stimulation voltage and muscle length (Lo) are adjusted to obtain maximum isometric twitch force. Maximum titanic force production (Po) is determined from the plateau of the frequency-force relationship.

Example 8

Therapeutic Treatment of Skeletal Muscle Atrophy Using a Human Antibody that is an Agonist of the $D_1$ and $D_5$ Dopamine Receptor A human male subject weighing 50 kg and having significant muscular atrophy of the arms and legs due to prolonged bed rest is treated to reverse the skeletal muscle atrophy. Once each week for a period of 3 months, 15 ml of an aqueous solution of pH 6 comprising an activating antibody of the $D_1$ and $D_5$ dopamine receptors are administered to the subject via intravenous injection. The solution comprises the following:

| Component | Concentration (mg/ml) |
|---|---|
| dopamine receptors activating antibody | 20 |
| L-histidine HCl | 0.47 |
| L-histidine | 0.3 |
| α, α-trehalose dihydrate | 20 |
| Polysorbate 20 | 0.1 |
| Bacteriostatic Sterile water | qs to 1 ml |

At the end of the treatment period, the subject exhibits measurable increases of muscle mass, strength and mobility of the arms and legs.

Example 9

Prophylactic Treatment of Skeletal Muscle Atrophy Using a Human Antibody that is an Agonist of the $D_1$ and $D_5$ Dopamine Receptors A human female subject weighing 55 kg is scheduled for hip joint replacement surgery in one month. The subject is treated to enhance skeletal muscle mass prior to and following surgery to ultimately reduce the level of skeletal muscle atrophy due to muscle disuse during post-surgery recovery. Specifically, once each week for a period of 1 month prior to surgery and for 2 months post-surgery, 18 ml of an aqueous solution of pH 6.0 comprising an activating antibody of the $D_1$ and $D_5$ dopamine receptors, are administered to the subject via intravenous injection. The solution comprises the following:

| Component | Concentration (mg/ml) |
|---|---|
| dopamine receptors activating antibody | 20 |
| L-histidine HCl | 0.47 |
| L-histidine | 0.3 |
| α, α-trehalose dihydrate | 20 |
| Polysorbate 20 | 0.1 |
| Bacteriostatic Sterile water | qs to 1 ml |

At the end of the treatment period, the subject exhibits measurable preservation of muscle mass, strength and mobility of the arms and legs as compared to the subject's expected status without antibody therapy.

Example 10

Prophylactic Treatment of Skeletal Muscle Atrophy Using a Human Antibody that is an Agonist of the $D_1$ and $D_5$ Dopamine Receptors A human female subject weighing 45 kg undergoes a casting procedure to treat a simple fracture of the humerus after a fall. The subject is treated to prevent atrophy of the skeletal muscle of the affected arm and shoulder due to disuse and limited use during fracture healing. Specifically, once each week starting on the day of casting, 13 ml of pH 6.0 comprising the anti-$D_1$ and $D_5$ dopamine receptors activating antibody is administered to the subject via intravenous injection. The solution comprises the following:

| Component | Concentration (mg/ml) |
|---|---|
| dopamine receptor activating antibody | 20 |
| L-histidine HCl | 0.47 |
| L-histidine | 0.3 |
| α, α-trehalose dihydrate | 20 |
| Polysorbate 20 | 0.1 |
| Bacteriostatic Sterile water | qs to 1 ml |

At the end of the treatment period, the subject exhibits measurable preservation of muscle mass, strength and mobility of the affected arm and shoulder and a reduced course of physical therapy as compared to the subject's expected status and follow-up treatment without antibody therapy.

Example 11

Prophylactic Treatment of Skeletal Muscle Atrophy Using Fenoldopam

A human female subject weighing 60 kg is admitted to the hospital in a comatose state. The subject is treated by this method to prevent atrophy of the skeletal muscle of the entire body due to disuse in the comatose state. Specifically, once each day while in the coma, the subject is administered, via slow intravenous infusion, approximately 500 ml of an aqueous solution that is prepared by addition of 5 ml of the following stock solution to 500 ml of sterile saline:

| Component | Concentration (mg/ml) |
|---|---|
| Fenoldopam | 12 |
| Sodium phosphate buffer, pH 7.4 | 140 |

As a result of treatment, the subject exhibits measurable preservation of skeletal muscle mass and function, and reduced physical therapy needs during the coma and after regaining consciousness, as compared to the subject's status without drug therapy.

Example 12

Therapeutic Treatment of a Patient with Duchenne Muscular Dystrophy Using Fenoldopam A male subject weighing 40 kg with an existing diagnosis of Duchenne's Muscular Dystrophy is treated with a sustained-release, depot formulation of Fenoldopam in order to improve or retain muscle strength and function over the progression of the disease. Specifically, once each month the subject is administered, via intramuscular injection, 3 ml of an aqueous solution of pH 6.0 comprising the following:

| Component | Concentration (mg/ml) |
|---|---|
| Fenoldopam | 4 |
| D,L lactic and glycolic acid copolymer | 5 |

As a result of the treatment, the subject experiences either an improvement or an attenuation of the decline of muscle strength or muscle function in timed-function evaluations as compared to that exhibited during the natural progression of the disease.

The present invention is not to be limited in scope by the specific embodiments described which are intended solely as illustrations of individual aspects of the invention, and functionally equivalent methods and components are within the scope of the invention. These include, but are not limited to, species of test animal, nature and type of dopamine receptor agonists, sex of the animal, model of atrophy, method of activating dopamine receptor including genetic methodologies, etc. Various modifications of the invention, in addition to those shown and described herein will be apparent to those skilled in the art upon reading foregoing description and accompanying figures. Such modifications are intended to fall within the scope of the appended claims.

What is claimed:

1. A method for identifying candidate compounds for regulating skeletal muscle mass or function, comprising:

a. contacting a test compound with a cell expressing a functional $D_5$ dopamine receptor;

b. determining whether the test compound activates the $D_5$ dopamine receptor;

c. selecting those compounds that activate the D5 dopamine receptor and further determining whether the test compound regulates muscle mass or function in a skeletal muscle atrophy model system;

d. identifying those test compounds which regulate muscle mass or function in the skeletal muscle atrophy model system as candidate compounds for regulating skeletal muscle mass or function.

2. The method for identifying candidate compounds according to claim 1, wherein the $D_5$ dopamine receptor has an amino acid sequence that is greater than 90% identical to the sequence of SEQ ID NO: 8.

3. The method for identifying candidate compounds according to claim 1, wherein the $D_5$ dopamine receptor has the amino acid sequence corresponding to the amino acid sequence of SEQ ID NO: 8, SEQ ID NO: 10, SEQ ID NO: 12, SEQ ID NO: 18, or SEQ ID NO: 24.

* * * * *

UNITED STATES PATENT AND TRADEMARK OFFICE

CERTIFICATE OF CORRECTION

PATENT NO. : 7,067,113 B2 
APPLICATION NO. : 10/299642
DATED : June 27, 2006
INVENTOR(S) : Robert Joseph Isfort et al.

It is certified that error appears in the above-identified patent and that said Letters Patent is hereby corrected as shown below:

Column 8
Line 54, please delete “(x-factor” and insert -- (a-factor --.

Column 10
Line 20, please delete “-7,8-dihydroxyl” and insert -- -7, 8-dihydroxyl --.

Column 12
Line 17, please delete “Receptors, Ropamine” and insert -- Receptors, Dopamine --.

Column 31
Line 15, please delete “BEK293” and insert -- HEK293 --.

Column 33
Line 21, please delete “NSA-bcd 2” and insert -- NSA-bcl 3 --.

Signed and Sealed this

First Day of September, 2009

David J. Kappos
*Director of the United States Patent and Trademark Office*